United States Patent
Miyazaki et al.

(10) Patent No.: US 9,920,068 B2
(45) Date of Patent: Mar. 20, 2018

(54) PYRIDINE COMPOUNDS

(71) Applicants: Daiichi Sankyo Company, Limited, Chuo-ku, Tokyo (JP); Sanford Burnham Prebys Medical Discovery Institute, La Jolla, CA (US)

(72) Inventors: Shojiro Miyazaki, Shinagawa-ku (JP); Yuko Yamamoto, Shinagawa-ku (JP); Keisuke Suzuki, Shinagawa-ku (JP); Masaharu Inui, Shinagawa-ku (JP); Masanori Izumi, Shinagawa-ku (JP); Kaori Soma, Shinagawa-ku (JP); Anthony Pinkerton, La Jolla, CA (US); Taeko Shinozaki, Shinagawa-ku (JP)

(73) Assignees: Daiichi Sankyo Company, Limited, Chuo-ku (JP); Sanford Burnham Prebys Medical Discovery Institute, La Jolla, CA (US)

( * ) Notice: Subject to any disclaimer, the term of this patent is extended or adjusted under 35 U.S.C. 154(b) by 0 days.

(21) Appl. No.: 15/314,887

(22) PCT Filed: Jul. 7, 2016

(86) PCT No.: PCT/US2016/041345
§ 371 (c)(1),
(2) Date: Nov. 29, 2016

(87) PCT Pub. No.: WO2017/007943
PCT Pub. Date: Jan. 12, 2017

(65) Prior Publication Data
US 2017/0240562 A1    Aug. 24, 2017

Related U.S. Application Data

(60) Provisional application No. 62/190,145, filed on Jul. 8, 2015.

(51) Int. Cl.
| | |
|---|---|
| *C07D 498/04* | (2006.01) |
| *C07D 498/10* | (2006.01) |
| *A61K 9/20* | (2006.01) |
| *A61K 9/48* | (2006.01) |
| *A61K 31/553* | (2006.01) |

(52) U.S. Cl.
CPC .............. *C07D 498/10* (2013.01); *A61K 9/20* (2013.01); *A61K 9/48* (2013.01); *A61K 31/553* (2013.01); *C07D 498/04* (2013.01)

(58) Field of Classification Search
CPC .................................................. C07D 498/04
See application file for complete search history.

(56) References Cited

U.S. PATENT DOCUMENTS

| 4,810,795 A | 3/1989 | Cale, Jr. |
| 2011/0053910 A1 | 3/2011 | McKerrecher et al. |
| 2015/0011551 A1 | 1/2015 | Pinkerton et al. |

FOREIGN PATENT DOCUMENTS

| EP | 1 145 714 A1 | 10/2001 |
| WO | 2009/017863 A2 | 2/2009 |
| WO | 2013/126608 A1 | 8/2013 |

OTHER PUBLICATIONS

Dahl, R., et al., "Discovery and Validation of a Series of Aryl Sulfonamides as Selective Inhibitors of Tissue-Nonspecific Alkaline Phosphatase (TNAP)," Journal of Medicinal Chemistry 52(21):6919-6925, Nov. 2009.
Debray, J., et al., "Inhibitors of Tissue-Nonspecific Alkaline Phosphatase: Design, Synthesis, Kinetics, Biomineralization and Cellular Tests," Bioorganic and Medicinal Chemistry 21(24):7981-7987, Dec. 2013.
Jono, S., et al., "Vascular Calcification in Chronic Kidney Disease," Journal of Bone and Mineral Metabolism 24(2):176-181, Mar. 2006.
Lanzer, P., et al., "Medial Vascular Calcification Revisited: Review and Perspectives," European Heart Journal 35(23):1515-1525, Jun. 2014.
Lomashvili, K.A., et al., "Phosphate-Induced Vascular Calcification: Role of Pyrophosphate and Osteopontin," Journal of the American Society of Nephrology 15(6):1392-1401, Jun. 2004.
Miao, D., and S. Scutt, "Histochemical Localization of Alkaline Phosphatase Activity in Decalcified Bone and Cartilage," Journal of Histochemistry and Cytochemistry 50(3):333-340, Mar. 2002.

(Continued)

*Primary Examiner* — Bruck Kifle
(74) *Attorney, Agent, or Firm* — Christensen O'Connor Johnson Kindness PLLC

(57) ABSTRACT

The present invention relates to a compound or a pharmacologically acceptable salt thereof having excellent tissue non-specific alkaline phosphatase inhibitory activity. The present invention provides a compound represented by the formula (I): wherein $R^1$ represents a hydrogen atom, an optionally substituted C1-6 alkyl group, or the like, $R^2$ and $R^3$ are the same or different and each represent a hydrogen atom, an optionally substituted C1-6 alkyl group, or the like, R4 and R5 are the same or different and each represent a hydrogen atom, an optionally substituted C1-6 alkyl group, or the like, $R^6$ represents a hydrogen atom or the like, each $R^7$ may be the same or different and may each represent an optionally substituted C1-6 alkoxy group or the like, X represents —CH=, —C(—$R^7$)=, or —N=, and m represents 1 to 4, or a pharmacologically acceptable salt thereof.

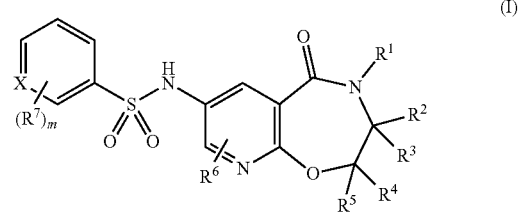

11 Claims, No Drawings

(56) References Cited

OTHER PUBLICATIONS

Narisawa, S., et al., "In Vivo Overexpression of Tissue-Nonspecific Alkaline Phosphatase Increases Skeletal Mineralization and Affects the Phosphorylation Status of Osteopontin," Journal of Bone and Mineral Research 28(7):1587-1598, Jul. 2013.

Narisawa, S., et al., "Novel Inhibitors of Alkaline Phosphatase Suppress Vascular Smooth Muscle Cell Calcification," Journal of Bone and Mineral Research 22(11):1700-1710, Nov. 2007.

Ossareh, S., "Clinical and Economic Aspects of Sevelamer Therapy in End-Stage Renal Disease Patients," International Journal of Nephrology and Renovascular Disease 7:161-168, May 2014.

Sheen, C.R., et al., "Pathophysiological Role of Vascular Smooth Muscle Alkaline Phosphatase in Medial Artery Calcification," Journal of Bone and Mineral Research 30(5):824-836, May 2015. (Author Manuscript provided, PMCID:PMC4406354, available in PMC May 1, 2015, 26 pages.)

Sidique, S., "Design and Synthesis of Pyrazole Derivatives as Potent and Selective Inhibitors of Tissue-Nonspecific Alkaline Phosphatase (TNAP)," Bioorganic and Medicinal Chemistry Letters 19(1):222-225, Jan. 2009.

Van Sickle, M.D., et al., "Cannabinoids Inhibit Emesis Through CB1 Receptors in the Brainstem of the Ferret," Gastroenterology 121(4):767-774, Oct. 2001.

Weber, C.I.K., et al., "Cardiovascular Risk Markers Associated With Arterial Calcification in Patients With Chronic Kidney Disease Stages 3 and 4," Clinical Kidney Journal 7(2):167-173, Apr. 2014.

International Search Report and Written Opinion dated Nov. 16, 2016, by the European Patent Office as the International Searching Authority, issued in International Application No. PCT/US2016/041345, filed Jul. 7, 2016, 9 pages.

International Search Report and Written Opinion dated Sep. 30, 2016, by the United States Patent Office as the International Searching Authority, issued in International Application No. PCT/US2016/041345, filed Jul. 7, 2016, 18 pages.

PYRIDINE COMPOUNDS

CROSS-REFERENCE TO RELATED APPLICATION

This application claims the benefit of U.S. Provisional Application No. 62/190,145, filed Jul. 8, 2015, expressly incorporated herein by reference in its entirety.

FIELD OF THE INVENTION

The present invention relates to a novel pyridine compound or a pharmacologically acceptable salt thereof which has excellent tissue non-specific alkaline phosphatase (hereinafter, referred to as TNAP) inhibitory activity.

The present invention also relates to a therapeutic agent and/or prophylactic agent (preferably a therapeutic agent) for pseudoxanthoma elasticum (PXE), generalized arterial calcification of infancy (GACI), craniometaphyseal dysplasia (CMD), ossification of the yellow ligament (OYL), ossification of ligamentum flavum, arterial calcification due to deficiency of CD73 (ACDC), calcification of joints and arteries (CALJA), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, idiopathic basal ganglia calcification (IBGC), heterotopic ossification (HO), calcific aortic valve disease (aortic valve stenosis), calcific tendinitis, ossification of the posterior longitudinal ligament (OPLL) ossification of the anterior longitudinal ligament (OALL), diffuse idiopathic skeletal hyperostosis (DISH), meniscal calcification, or peritoneal calcification, comprising the compound or the pharmacologically acceptable salt thereof as an active ingredient.

The present invention further relates to a composition for the treatment or prophylaxis of the aforementioned diseases, comprising the compound or the pharmacologically acceptable salt thereof as an active ingredient, use of the compound or the pharmacologically acceptable salt thereof for manufacturing a pharmaceutical for the treatment or prophylaxis of the disease, and a method for the treatment or prophylaxis of the disease, comprising administering a pharmacologically effective amount of the compound or the pharmacologically acceptable salt thereof to a mammal (preferably a human).

DESCRIPTION OF THE RELATED ART

In vivo calcification is strictly regulated by the balance of activation between osteoblasts and osteoclasts, phosphorus and calcium concentrations in plasma, and parathyroid hormone or vitamin D secreted in order to maintain the homeostasis of these concentrations (Non Patent Literature 1). Ectopic calcification is found in diseases, for example, pseudoxanthoma elasticum (PXE), generalized arterial calcification of infancy (GACI), craniometaphyseal dysplasia (CMD), ossification of the yellow ligament (OYL), ossification of ligamentum flavum, arterial calcification due to deficiency of CD73 (ACDC), calcification of joints and arteries (CALJA), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, idiopathic basal ganglia calcification (IBGC), heterotopic ossification (HO), calcific aortic valve disease (aortic valve stenosis), calcific tendinitis, ossification of the posterior longitudinal ligament (OPLL) ossification of the anterior longitudinal ligament (OALL), diffuse idiopathic skeletal hyperostosis (DISH), meniscal calcification, and peritoneal calcification. In these pathological conditions, calcification in tissues (blood vessels, soft tissues, etc.) that are usually not calcified is caused by the failure of the regulatory mechanism mentioned above, and is known to bring about significantly reduced quality of life (QOL) due to the limitation of activity and an increased cardiovascular risk (Non Patent Literatures 2 and 3). No existing therapeutic agent is effective for ectopic calcification. Thus, there are very high unmet medical needs for this disease (Non Patent Literature 4).

TNAP, one of alkaline phosphatases, includes membrane-bound and secretory forms. TNAP is expressed in the bone, the liver, and the kidney and highly expressed particularly in the matrix vesicles of chondrocytes and osteoblasts. This enzyme is known to play an important role in in vivo calcification via the degradation of pyrophosphate, which is an endogenous anti-calcification factor (Non Patent Literature 5). A large number of reports show the increased expression level or elevated activity of TNAP at lesion sites of ectopic calcification, and ectopic calcification also occurs in mice which overexpress human TNAP, suggesting the importance of TNAP for ectopic calcification (Non Patent Literatures 6 and 7). Thus, the inhibition of TNAP is considered to elevate pyrophosphate concentrations in blood and in tissues and suppress ectopic calcification (Non Patent Literature 8).

Some compounds are known to have TNAP inhibitory activity (see e.g., Patent Literatures 1 and 2 and, Non Patent Literatures 9 to 12). Among them, compounds partially having a common skeleton are disclosed. Nonetheless, a compound having a 7-membered ring condensed with a pyridine ring has not yet been disclosed.

PATENT LITERATURE

[Patent Literature 1] International Publication No. WO 2009/017863 (PCT/US2008/063106)

[Patent Literature 2] International Publication No. WO 2013/126608 (U.S. Patent Publication No. 2015-0011551)

Non Patent Literature

[Non Patent Literature 1] J. Bone Miner Res, 2006, vol. 24, p. 176-181
[Non Patent Literature 2] Clin. Kidery. J., 2014, vol. 7, p. 167-173
[Non Patent Literature 3] Eur. Heart. J., 2014, vol. 35, p. 1515-1525.
[Non Patent Literature 4] Int. J. Nephrol. Renovasc. Dis., 2014, vol. 7, p. 161-168
[Non Patent Literature 5] J. Histochem. Cytochem., 2002, vol. 50, p. 333-340
[Non Patent Literature 6] J. Am. Soc. Nephrol., 2004, vol. 15, p. 1392-1401
[Non Patent Literature 7] J. Bone Miner Res, 2013, vol. 7, p. 1587-1598
[Non Patent Literature 8] J. Bone Miner Res, 2007, vol. 22, p. 1700-1710
[Non Patent Literature 9] Bioorg. Med. Chem. Lett., 2009, vol. 19, p. 222-225
[Non Patent Literature 10] J. Med. Chem., 2009, vol. 52, p. 6919-6925
[Non Patent Literature 11] Bioorg. Med. Chem., 2013, vol. 21, p. 7981-7897
[Non Patent Literature 12] J. Bone Miner Res, 2015, vol. 30, p. 824-836

SUMMARY OF THE INVENTION

The present inventors have conducted diligent studies and consequently found that a compound represented by the formula (I) mentioned later has excellent TNAP inhibitory activity based on its specific chemical structure, further has excellent properties in terms of the physicochemical properties (e.g., stability) of a pharmaceutical, and serves as a safe and useful pharmaceutical as a prophylactic or therapeutic agent for a pathological condition or a disease associated with ectopic calcification. On the basis of these findings, the present invention has been completed.

Specifically, the compound of the present invention has excellent properties in terms of TNAP inhibitory activity, solubility, cell membrane permeability, oral absorbability, concentration in blood, metabolic stability, tissue penetration, bioavailability (hereinafter, also referred to as BA), in vitro activity, in vivo activity, ex vivo activity, quick onset of drug efficacy, persistence of drug efficacy, physical stability, drug interaction, safety (e.g., cardiotoxicity or hepatotoxicity), etc., and is useful as a pharmaceutical [particularly, a pharmaceutical for the treatment or prophylaxis (preferably treatment) of pseudoxanthoma elasticum (PXE), generalized arterial calcification of infancy (GACI), craniometaphyseal dysplasia (CMD), ossification of the yellow ligament (OYL), ossification of ligamentum flavum, arterial calcification due to deficiency of CD73 (ACDC), calcification of joints and arteries (CALJA), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, idiopathic basal ganglia calcification (IBGC), heterotopic ossification (HO), calcific aortic valve disease (aortic valve stenosis), calcific tendinitis, ossification of the posterior longitudinal ligament (OPLL) ossification of the anterior longitudinal ligament (OALL), diffuse idiopathic skeletal hyperostosis (DISH), meniscal calcification, or peritoneal calcification].

The present invention provides:
(1) a compound represented by the following general formula (I):

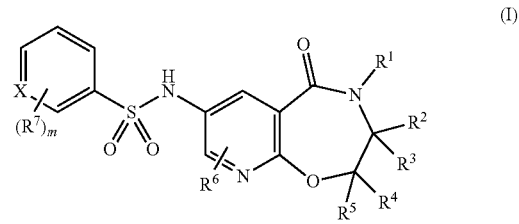

(I)

wherein
$R^1$ represents
a hydrogen atom,
a C1-6 alkyl group (wherein the alkyl group is optionally substituted by one to three groups, which may be the same or different, selected from the following substituents:
a hydroxy group, a C1-6 alkoxy group optionally substituted by one to three groups, which may be the same or different halogeno groups, an amino group optionally substituted by one or two groups, which may be the same or different C1-6 alkyl groups, a C6-10 aryl group optionally substituted by one or two groups selected from substituent group $A^B$, a 3- to 10-membered heterocyclyl group containing one to four heteroatoms, which may be the same or different, selected from nitrogen, oxygen, and sulfur and optionally substituted by one or two groups selected from substituent group $A^B$, a carboxyl group, a C1-6 alkylcarbonyl group, a C1-6 alkoxycarbonyl group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur),
a C3-8 cycloalkyl group (wherein the cycloalkyl group is optionally substituted by one to three groups, which may be the same or different, selected from the following substituents:
a hydroxy group, a C1-6 alkoxy group optionally substituted by one to three groups, which may be the same or different halogeno groups, a C3-8 cycloalkyl group optionally substituted by one to three groups, which may be the same or different halogeno groups, a C6-10 aryl group optionally substituted by one or two groups, which may be the same or different halogeno groups, a 3- to 10-membered heterocyclyl group containing one to four heteroatoms, which may be the same or different, selected from nitrogen, oxygen, and sulfur and optionally substituted by one or two groups, which may be the same or different halogeno groups, a carboxyl group, a C1-6 alkylcarbonyl group, a C1-6 alkoxycarbonyl group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, a halogeno group, and a cyano group), a C6-10 aryl group (wherein the aryl group is optionally substituted by one or two groups, which may be the same or different, selected from the following substituents:

a hydroxy group, a C1-6 alkyl group optionally substituted by one to three groups, which may be the same or different halogeno groups, a C3-8 cycloalkyl group optionally substituted by one to three groups, which may be the same or different halogeno groups, a C1-6 alkoxy group optionally substituted by one to three groups, which may be the same or different halogeno groups, a C6-10 aryl group optionally substituted by one group selected from substituent group $A^B$, a 3- to 10-membered heterocyclyl group containing one to four heteroatoms, which may be the same or different, selected from nitrogen, oxygen, and sulfur and optionally substituted by one group selected from substituent group $A^B$, a carboxyl group, an amino group optionally substituted by one or two groups, which may be the same or different C1-6 alkyl groups, a C1-6 alkoxycarbonyl group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, a halogeno group, and a cyano group), or a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from the following substituents:

a hydroxy group, a C1-6 alkyl group optionally substituted by one to three groups, which may be the same or different halogeno groups, a C3-8 cycloalkyl group optionally substituted by one to three groups, which may be the same or different halogeno groups, a C1-6 alkoxy group optionally substituted by one to three groups, which may be the same or different halogeno groups, a C6-10 aryl group, a 3- to 10-membered heterocyclyl group containing one to four heteroatoms, which may be the same or different, selected from nitrogen, oxygen, and sulfur, a carboxyl group, an amino group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, a halogeno group, and a cyano group), $R^2$ and $R^3$ are the same or different and each represent a hydrogen atom, a C1-6 alkyl group (wherein the alkyl group is optionally substituted by one to three groups, which may be the same or different, selected from the following substituents:

a hydroxy group, a C1-6 alkoxy group optionally substituted by one group selected from substituent group $A^C$, a C3-8 cycloalkyl group optionally substituted by one group selected from substituent group $A^B$, a C6-10 aryl group optionally substituted by one or two groups selected from substituent group $A^B$, a 3- to 10-membered heterocyclyl group containing one to four heteroatoms, which may be the same or different, selected from nitrogen, oxygen, and sulfur and optionally substituted by one or two groups selected from substituent group $A^B$, a carboxyl group, a C1-6 alkylcarbonyl group, a C1-6 alkoxycarbonyl group, an amino group optionally substituted by one or two groups, which may be the same or different C1-6 alkyl groups, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, a halogeno group, and a cyano group), a C6-10 aryl group (wherein the aryl group is optionally substituted by one or two groups, which may be the same or different, selected from the following substituents:

a hydroxy group, a C1-6 alkoxy group optionally substituted by one to three groups, which may be the same or different halogeno groups, a C1-6 alkyl group optionally substituted by one group selected from substituent group $A^D$, a C3-8 cycloalkyl group optionally substituted by one group selected from substituent group $A^D$, a C6-10 aryl group optionally substituted by one group selected from substituent group $A^D$, a 3- to 10-membered heterocyclyl group containing one to four heteroatoms, which may be the same or different, selected from nitrogen, oxygen, and sulfur and optionally substituted by one group selected from substituent group $A^D$, an amino group optionally substituted by one or two groups, which may be the same or different C1-6 alkyl groups, a carboxyl group, a C1-6 alkylcarbonyl group, a C1-6 alkoxycarbonyl group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur,
a halogeno group, and a cyano group),
a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from the following substituents:
a hydroxy group, a C1-6 alkoxy group optionally substituted by one to three groups, which may be the same or different halogeno groups,
a C1-6 alkyl group optionally substituted by one group selected from substituent group $A^D$, a C3-8 cycloalkyl group optionally substituted by one group selected from substituent group $A^D$, a C6-10 aryl group optionally substituted by one group selected from substituent group $A^D$, a 3- to 10-membered heterocyclyl group containing one to four heteroatoms, which may be the same or different, selected from nitrogen, oxygen, and sulfur and optionally substituted by one group selected from substituent group $A^D$,
an amino group optionally substituted by one or two groups, which may be the same or different C1-6 alkyl groups,
a carboxyl group, a C1-6 alkylcarbonyl group, a C1-6 alkoxycarbonyl group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur,
a halogeno group, and a cyano group),
a C1-6 alkylcarbonyl group (wherein the alkylcarbonyl group is optionally substituted by one to three groups, which may be the same or different, selected from substituent group $A^E$),
a C6-10 arylcarbonyl group (wherein the arylcarbonyl group is optionally substituted by one or two groups, which may be the same or different, selected from substituent group $A^E$ and a C1-6 halogenoalkyl group),
a 3- to 10-membered heterocyclylcarbonyl group containing one to four heteroatoms, which may be the same or different, selected from nitrogen, oxygen, and sulfur (wherein the heterocyclylcarbonyl group is optionally substituted by one or two groups, which may be the same or different, selected from substituent group $A^E$ and a C1-6 halogenoalkyl group),
a carboxyl group,
a C1-6 alkoxycarbonyl group (wherein the alkoxycarbonyl group is optionally substituted by one to three groups, which may be the same or different, selected from substituent group $A^F$),
an aminocarbonyl group (wherein the aminocarbonyl group is optionally substituted by one or two groups, which may be the same or different C1-6 alkyl groups each optionally substituted by one to three groups, which may be the same or different, selected from substituent group $A^F$),
a C6-10 arylaminocarbonyl group (wherein the arylaminocarbonyl group is optionally substituted by one or two groups, which may be the same or different, selected from substituent group $A^E$ and a C1-6 halogenoalkyl group),
a 4- to 7-membered saturated heterocyclylcarbonyl group containing one or two heteroatoms, which may be the same or different, selected from nitrogen, oxygen, and sulfur (wherein the heterocyclylcarbonyl group is optionally substituted by one to three groups, which may be the same or different, selected from substituent group $A^F$), or
a 3- to 10-membered heterocyclylaminocarbonyl group containing one to four heteroatoms, which may be the same or different, selected from nitrogen, oxygen, and sulfur (wherein the heterocyclylaminocarbonyl group is optionally substituted by one or two groups, which may be the same or different, selected from substituent group $A^E$ and a C1-6 halogenoalkyl group),
or
the C1-6 alkyl groups of $R^2$ and $R^3$ are optionally bonded to each other to form a 3- to 6-membered saturated carbocyclic ring or to form a 4- to 6-membered saturated heterocyclic ring via one nitrogen or oxygen atom (wherein one nitrogen atom in the 4- to 6-membered saturated heterocyclic ring is optionally replaced with a hydrogen atom, a C1-6 alkyl group, a C1-6 alkylcarbonyl group, a C1-6 alkoxycarbonyl group),
$R^4$ and $R^5$ are the same or different and each represent a hydrogen atom,
a C1-6 alkyl group (wherein the alkyl group is optionally substituted by one to three groups, which may be the same or different, selected from substituent group $A^G$),
a C6-10 aryl group (wherein the aryl group is optionally substituted by one or two groups, which may be the same or different, selected from substituent group $A^G$), or
a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group $A^G$),
$R^6$ represents a hydrogen atom, hydroxyl group or a C1-6 alkyl group ($R^6$ is a carbon substituent of the pyridinyl ring, not a nitrogen substituent),
each substituent $R^7$ may be the same or different and may each represent
a C1-6 alkyl group (wherein the alkyl group is optionally substituted by one to three groups, which may be the same or different, selected from substituent group $A^H$),
a C1-6 alkoxy group (wherein the alkoxy group is optionally substituted by one to three groups, which may be the same or different, selected from substituent group $A^H$),
a halogeno group,
a C6-10 aryl group (wherein the aryl group is optionally substituted by one or two groups, which may be the same or different, selected from substituent group $A^G$),
a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group $A^G$),
a hydroxy group,
an amino group (wherein the amino group is optionally substituted by one or two groups, which may be the same or different C1-6 alkyl groups each optionally substituted by one to three groups, which may be the same or different, selected from substituent group $A^J$),
a carboxyl group,
a C1-6 alkoxycarbonyl group (wherein the alkoxycarbonyl group is optionally substituted by one to three groups, which may be the same or different, selected from substituent group $A^J$),
an aminocarbonyl group (wherein the aminocarbonyl group is optionally substituted by one or two groups, which may be the same or different C1-6 alkyl groups each optionally substituted by one to three groups, which may be the same or different, selected from substituent group $A^J$), or a cyano group, X represents —CH═, —C(—$R^7$)═, or —N═, m represents an integer selected from 1 to 4, and the substituent groups represent $A^B$: a hydroxy group, a C1-6 alkyl group (wherein the alkyl group is optionally substituted by one to three halogeno groups), a C1-6 alkoxy group (wherein the alkoxy group is optionally substituted by one to three halogeno groups), a halogeno group, an amino group, and a cyano group;

$A^C$: a C6-10 aryl group, a 3- to 10-membered heterocyclyl group containing one to four heteroatoms, which may be the same or different, selected from nitrogen, oxygen, and sulfur, and a halogeno group;

$A^D$: a hydroxy group, a C1-6 alkoxy group, an amino group, a halogeno group, and a cyano group;

$A^E$: a hydroxy group, a C1-6 alkoxy group, a C3-8 cycloalkyl group, a C6-10 aryl group, a 3- to 10-membered heterocyclyl group containing one to four heteroatoms, which may be the same or different, selected from nitrogen, oxygen, and sulfur, an amino group (wherein the amino group is optionally substituted by one or two groups, which may be the same or different C1-6 alkyl groups), a halogeno group, and a cyano group;

$A^F$: a C1-6 alkoxy group, a C3-8 cycloalkyl group, a C6-10 aryl group, a 3- to 10-membered heterocyclyl group containing one to four heteroatoms, which may be the same or different, selected from nitrogen, oxygen, and sulfur, a halogeno group, and a cyano group;

$A^G$: a hydroxy group, a C1-6 alkoxy group, an amino group (wherein the amino group is optionally substituted by one or two groups, which may be the same or different C1-6 alkyl groups), a halogeno group, and a cyano group;

$A^H$: a hydroxy group, a C1-6 alkoxy group, a C3-8 cycloalkyl group, a C6-10 aryl group, a 3- to 10-membered heterocyclyl group containing one to four heteroatoms, which may be the same or different, selected from nitrogen, oxygen, and sulfur, a carboxyl group, a C1-6 alkoxycarbonyl group, an aminocarbonyl group (wherein the aminocarbonyl group is optionally substituted by one or two groups, which may be the same or different C1-6 alkyl groups), an amino group (wherein the amino group is optionally substituted by one or two groups, which may be the same or different C1-6 alkyl groups), a halogeno group, and a cyano group; and $A^J$: a C1-6 alkoxy group, a C3-8 cycloalkyl group, a C6-10 aryl group, a 3- to 10-membered heterocyclyl group containing one to four heteroatoms, which may be the same or different, selected from nitrogen, oxygen, and sulfur, a carboxyl group, a C1-6 alkoxycarbonyl group, an aminocarbonyl group (wherein the aminocarbonyl group is optionally substituted by one or two groups, which may be the same or different C1-6 alkyl groups), a halogeno group, and a cyano group, or a pharmacologically acceptable salt thereof;

(2) a compound represented by the following general formula (Ia):

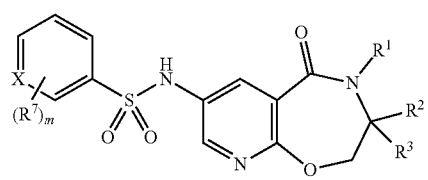

(Ia)

wherein $R^1$ represents a hydrogen atom, a C1-6 alkyl group (wherein the alkyl group is optionally substituted by one hydroxy group or C1-6 alkoxy group), a C6-10 aryl group, or a 3- to 10-membered heterocyclyl group containing one to four heteroatoms, which may be the same or different, selected from nitrogen, oxygen, and sulfur, $R^2$ and $R^3$ are the same or different and each represent a hydrogen atom or a C1-6 alkyl group (wherein the alkyl group is optionally substituted by one hydroxy group), or the C1-6 alkyl groups of $R^2$ and $R^3$ are optionally bonded to each other to form a 3- to 6-membered saturated carbocyclic ring, each substituent $R^7$ may be the same or different and may represent a C1-6 alkoxy group (wherein the alkoxy group is optionally substituted by one to three halogeno groups) or a halogeno group, X represents —CH═, —C(—$R^7$)═, or —N═, and m represents an integer of 1 or 2, or a pharmacologically acceptable salt thereof;

(3) a compound according to the above (2), wherein $R^1$ is hydrogen atom;

(4) a compound according to the above (2), wherein $R^2$ and $R^3$ are the same or different and each represent a hydrogen atom or the C1-6 alkyl groups of $R^2$ and $R^3$ are optionally bonded to each other to form a 3- to 6-membered saturated carbocyclic ring;

(5) a compound according to the above (2), wherein each substituent $R^7$ may be the same or different and may represent a methoxy group, ethoxy group, trifluoromethoxy group, fluoro or chloro;

(6) a compound according to the above (1) selected from the group consisting of:

5-chloro-2-methoxy-N-(4-methyl-5-oxo-2,3,4,5-tetrahydropyrido[3,2-f][1,4]oxazepin-7-yl)benzenesulfonamide;

5-fluoro-2-methoxy-N-(4-methyl-5-oxo-2,3,4,5-tetrahydropyrido[3,2-f][1,4]oxazepin-7-yl)benzenesulfonamide;

5-chloro-N-[4-(2-hydroxyethyl)-5-oxo-2,3,4,5-tetrahydropyrido[3,2-f][1,4]oxazepin-7-yl]-2-methoxybenzenesulfonamide;

5-fluoro-2-methoxy-N-[(3S)-3-methyl-5-oxo-2,3,4,5-tetrahydropyrido[3,2-f][1,4]oxazepin-7-yl]benzenesulfonamide;

5-chloro-N-[(3S)-3-(hydroxymethyl)-5-oxo-2,3,4,5-tetrahydropyrido[3,2-f][1,4]oxazepin-7-yl]-2-methoxybenzenesulfonamide;

5-fluoro-N-[(3S)-3-(hydroxymethyl)-5-oxo-2,3,4,5-tetrahydropyrido[3,2-f][1,4]oxazepin-7-yl]-2-methoxybenzenesulfonamide;

5-bromo-N-[(3S)-3-(hydroxymethyl)-5-oxo-2,3,4,5-tetrahydropyrido[3,2-f][1,4]oxazepin-7-yl]-2-methoxybenzenesulfonamide;

5-chloro-N-[(3S)-3-(2-hydroxyethyl)-5-oxo-2,3,4,5-tetrahydropyrido[3,2-f][1,4]oxazepin-7-yl]-2-methoxybenzenesulfonamide; and pharmacologically acceptable salts thereof;

(7) a compound according to the above (1) selected from the group consisting of:

5-chloro-2-methoxy-N-(5-oxo-2,3,4,5-tetrahydropyrido[3,2-f][1,4]oxazepin-7-yl)benzenesulfonamide;

5-chloro-N-(5-oxo-2,3,4,5-tetrahydropyrido[3,2-f][1,4]oxazepin-7-yl)-2-(trifluoromethoxy)benzenesulfonamide;

5-chloro-N-[(3S)-3-(hydroxymethyl)-5-oxo-2,3,4,5-tetrahydropyrido[3,2-f][1,4]oxazepin-7-yl]-2-(trifluoromethoxy)benzenesulfonamide;

5-fluoro-2-methoxy-N-(5'-oxo-4',5'-dihydrospiro[cyclopropane-1,3'-pyrido[3,2-f][1,4]oxazepin]-7'-yl)benzenesulfonamide;
5-chloro-N-(5'-oxo-4',5'-dihydrospiro[cyclopropane-1,3'-pyrido[3,2-f][1,4]oxazepin]-7'-yl)-2-(trifluoromethoxy)benzenesulfonamide;
5-fluoro-N-(5'-oxo-4',5'-dihydrospiro[cyclopropane-1,3'-pyrido[3,2-f][1,4]oxazepin]-7'-yl)-2-(trifluoromethoxy)benzenesulfonamide;
2,5-dimethoxy-N-(5'-oxo-4',5'-dihydrospiro[cyclopropane-1,3'-pyrido[3,2-f][1,4]oxazepin]-7'-yl)benzenesulfonamide; and
pharmacologically acceptable salts thereof;
(8) a compound according to the above (1), where the compound is 5-fluoro-2-methoxy-N-(5-oxo-2,3,4,5-tetrahydropyrido[3,2-f][1,4]oxazepin-7-yl)benzenesulfonamide, or a pharmacologically acceptable salt thereof;
(9) a compound according to the above (1), where the compound is 5-chloro-2-methoxy-N-(5'-oxo-4',5'-dihydrospiro[cyclopropane-1,3'-pyrido[3,2-f][1,4]oxazepin]-7'-yl)benzenesulfonamide, or a pharmacologically acceptable salt thereof;
(10) a compound according to the above (1), where the compound is
2-ethoxy-5-fluoro-N-(5'-oxo-4',5'-dihydrospiro[cyclopropane-1,3'-pyrido[3,2-f][1,4]oxazepin]-7'-yl)benzenesulfonamide, or a pharmacologically acceptable salt thereof;
(11) a compound according to the above (1) to (10), wherein the pharmacologically acceptable salt is sodium salt;
(12) a compound according to the above (1) to (10), wherein the pharmacologically acceptable salt is potassium salt;
(13) a pharmaceutical composition comprising a compound according to the above (1) to (10) or a pharmacologically acceptable salt thereof as an active ingredient;
(14) the pharmaceutical composition according to the above (13), wherein the pharmaceutical composition is intended for the treatment or prophylaxis of ectopic calcification, pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), or aortic stenosis;
(15) a TNAP inhibitor comprising a compound according to the above (1) to (10) or a pharmacologically acceptable salt thereof as an active ingredient;
(16) a method for the treatment or prophylaxis of a disease or condition selected from the group consisting of ectopic calcification, pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), and aortic stenosis, comprising administering a therapeutically effective amount of a compound according to the above (1) to (10) or a pharmacologically acceptable salt thereof to a subject in need thereof;
(17) a method according to (16), wherein the disease or condition is pseudoxanthoma elasticum (PXE);
(18) a method for inhibiting TNAP in a subject, comprising administering an effective amount of a compound according to the above (1) to (10) or a pharmacologically acceptable salt thereof to the subject;
(19) a method according to the above (16) to (18), wherein the subject is a human;
(20) use of a compound according to the above (1) to (10) or a pharmacologically acceptable salt thereof for the manufacturing a pharmaceutical composition;
(21) a compound according to the above (1) to (10) or a pharmacologically acceptable salt thereof for use in the treatment of disease or condition selected from the group consisting of ectopic calcification, pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), and aortic stenosis; and
(22) a compound according to the above (1) to (10) or a pharmacologically acceptable salt thereof for use in the treatment of pseudoxanthoma elastic (PXE).

In the present invention, the "C1-6 alkyl group" refers to a linear or branched alkyl group having 1 to 6 carbon atoms. Examples thereof can include methyl, ethyl, n-propyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl groups. For $R^1$, $R^2$, $R^3$, $R^4$, $R^5$, $R^6$, $R^7$, or $A^B$, the C1-6 alkyl group is preferably an alkyl group having 1 to 3 carbon atoms, most preferably an ethyl or methyl group.

In the present invention, the "C1-6 alkylcarbonyl group" refers to the aforementioned "C1-6 alkyl group" bonded to a carbonyl group. Examples thereof can include methylcarbonyl, ethylcarbonyl, n-propylcarbonyl, n-butylcarbonyl, isobutylcarbonyl, s-butylcarbonyl, tert-butylcarbonyl, n-pentylcarbonyl, isopentylcarbonyl, 2-methylbutylcarbonyl, neopentylcarbonyl, 1-ethylpropylcarbonyl, n-hexylcarbonyl, isohexylcarbonyl, 4-methylpentylcarbonyl, 3-methylpentylcarbonyl, 2-methylpentylcarbonyl, 1-methylpentylcarbonyl, 3,3-dimethylbutylcarbonyl, 2,2-dimethylbutylcarbonyl, 1,1-dimethylbutylcarbonyl, 1,2-dimethylbutylcarbonyl, 1,3-dimethylbutylcarbonyl, 2,3-dimethylbutylcarbonyl, and 2-ethylbutylcarbonyl groups. For $R^1$, $R^2$, or $R^3$, the C1-6 alkylcarbonyl group is preferably an alkylcarbonyl group having 1 to 3 carbon atoms, most preferably a methylcarbonyl group.

In the present invention, the "C3-8 cycloalkyl group" refers to a 3- to 8-membered saturated cyclic hydrocarbon group. Examples thereof can include cyclopropyl, cyclobutyl, cyclopentyl, cyclohexyl, cycloheptyl, and cyclooctyl groups. For $R^1$, $R^2$, $R^3$, $R^4$, $R^5$, $R^7$, $A^E$, $A^F$, $A^H$, or $A^J$, the C3-8 cycloalkyl group is preferably a 3- to 6-membered saturated cyclic hydrocarbon group, more preferably a cyclopropyl, cyclobutyl, cyclopentyl, or cyclohexyl group.

In the present invention, the "C6-10 aryl group" refers to an aromatic hydrocarbon group having 6 to 10 carbon atoms. Examples thereof can include phenyl, indenyl, and naphthyl groups. For $R^1$, $R^2$, $R^3$, $R^4$, $R^5$, $R^7$, $A^C$, $A^E$, $A^F$, $A^H$, or $A^J$, the C6-10 aryl group is preferably a phenyl group.

In the present invention, the "C1-6 alkoxy group" refers to the aforementioned "C1-6 alkyl group" bonded to an oxygen atom. Examples thereof can include linear or branched alkoxy groups each having 1 to 6 carbon atoms, such as methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, and 2,3-dimethylbutoxy. For $R^1$, $R^2$, $R^3$, $R^7$, $A^B$, $A^D$, $A^E$, $A^F$, $A^G$, $A^H$, or $A^J$, the C1-6 alkoxy group is preferably a methoxy or ethoxy group.

In the present invention, the "C1-6 alkoxycarbonyl group" refers to the aforementioned "C1-6 alkoxy group" bonded to a carbonyl group. Examples thereof can include linear or branched alkoxycarbonyl groups each having 1 to 6 carbon atoms, such as methoxycarbonyl, ethoxycarbonyl, n-propoxycarbonyl, isopropoxycarbonyl, n-butoxycarbonyl, isobutoxycarbonyl, s-butoxycarbonyl, tert-butoxycarbonyl, n-pentoxycarbonyl, isopentoxycarbonyl, 2-methylbutoxycarbonyl, neopentoxycarbonyl, n-hexyloxycarbonyl, 4-methylpentoxycarbonyl, 3-methylpentoxycarbonyl, 2-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, and 2,3-dimethylbutoxycarbonyl. For $R^1$, $R^2$, $R^3$, $R^7$, $A^H$, or $A^J$, the C1-6 alkoxycarbonyl group is preferably a methoxycarbonyl or ethoxycarbonyl group.

In the present invention, the "4- to 7-membered saturated heterocyclyl group containing one or two heteroatoms, which may be the same or different, selected from nitrogen, oxygen, and sulfur" refers to a 4- to 7-membered saturated heterocyclic group containing one or two atoms of nitrogen, oxygen, and sulfur. Examples thereof can include oxetanyl, morpholinyl, thiomorpholinyl, pyrrolidinyl, pyrrolinyl, imidazolidinyl, imidazolinyl, pyrazolidinyl, pyrazolinyl, piperidinyl, piperazinyl, tetrahydrofuranyl, tetrahydropyranyl, and 5-oxo-4,5-dihydro-1,2,4-oxadiazolyl groups.

In the present invention, the "4- to 7-membered saturated heterocyclylcarbonyl group containing one or two heteroatoms, which may be the same or different, selected from nitrogen, oxygen, and sulfur" refers to the aforementioned "4- to 7-membered saturated heterocyclyl group containing one or two heteroatoms, which may be the same or different, selected from nitrogen, oxygen, and sulfur" bonded to a carbonyl group. Examples thereof can include morpholinylcarbonyl, thiomorpholinylcarbonyl, pyrrolidinylcarbonyl, pyrrolinylcarbonyl, piperidinylcarbonyl, piperazinylcarbonyl, tetrahydrofuranylcarbonyl, tetrahydropyranylcarbonyl, and 5-oxo-4,5-dihydro-1,2,4-oxadiazolylcarbonyl groups.

In the present invention, the "4- to 7-membered saturated heterocyclylcarbonyloxy group containing one or two heteroatoms, which may be the same or different, selected from nitrogen, oxygen, and sulfur" refers to the aforementioned "4- to 7-membered saturated heterocyclylcarbonyl group containing one or two heteroatoms, which may be the same or different, selected from nitrogen, oxygen, and sulfur" bonded to an oxygen atom. Examples thereof can include morpholinylcarbonyloxy, thiomorpholinylcarbonyloxy, pyrrolidinylcarbonyloxy, pyrrolinylcarbonyloxy, piperidinylcarbonyloxy, piperazinylcarbonyloxy, tetrahydrofuranylcarbonyloxy, tetrahydropyranylcarbonyloxy, and 5-oxo-4,5-dihydro-1,2,4-oxadiazolylcarbonyloxy groups.

In the present invention, the "3- to 10-membered heterocyclyl group containing one to four heteroatoms, which may be the same or different, selected from nitrogen, oxygen, and sulfur" refers to a 3- to 10-membered heterocyclic group containing one to four atoms of nitrogen, oxygen, and sulfur. Examples thereof can include the groups listed as the examples of the aforementioned "4- to 7-membered heterocyclyl group containing one or two heteroatoms, which may be the same or different, selected from nitrogen, oxygen, and sulfur", and aromatic heterocyclic groups such as furyl, thienyl, pyrrolyl, azepinyl, pyrazolyl, imidazolyl, oxazolyl, oxadiazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, and pyrazinyl. The "3- to 10-membered heterocyclic group" may be condensed with an additional cyclic group. Examples thereof can include benzofuranyl, chromenyl, indolizinyl, isoindolyl, indolyl, indazolyl, purinyl, quinolizinyl, isoquinolyl, quinolyl, phthalazinyl, naphthyridinyl, quinoxalinyl, quinazolinyl, isoindolinyl, 2,3-dihydro-1-benzofuranyl, 3,4-dihydro-1H-isochromenyl, 1,2,3,4-tetrahydroquinolinyl, and 1,2,3,4-tetrahydroisoquinolinyl groups.

In the present invention, the "3- to 10-membered heterocyclylcarbonyl group containing one to four heteroatoms, which may be the same or different, selected from nitrogen, oxygen, and sulfur" refers to the aforementioned "3- to 10-membered heterocyclyl group containing one to four heteroatoms, which may be the same or different, selected from nitrogen, oxygen, and sulfur" bonded to a carbonyl group. Examples thereof can include the groups listed as the examples of the aforementioned "4- to 7-membered saturated heterocyclylcarbonyl group containing one or two heteroatoms, which may be the same or different, selected from nitrogen, oxygen, and sulfur", and carbonyl groups of aromatic heterocyclic groups such as furylcarbonyl, thienylcarbonyl, pyrrolylcarbonyl, azepinylcarbonyl, pyrazolylcarbonyl, imidazolylcarbonyl, oxazolylcarbonyl, oxadiazolylcarbonyl, isoxazolylcarbonyl, thiazolylcarbonyl, isothiazolylcarbonyl, 1,2,3-oxadiazolylcarbonyl, triazolylcarbonyl, tetrazolylcarbonyl, thiadiazolylcarbonyl, pyranylcarbonyl, pyridylcarbonyl, pyridazinylcarbonyl, pyrimidinylcarbonyl, and pyrazinylcarbonyl groups.

In the present invention, the "3- to 10-membered heterocyclylaminocarbonyl group containing one or two heteroatoms, which may be the same or different, selected from nitrogen, oxygen, and sulfur" refers to the aforementioned "3- to 10-membered heterocyclyl group containing one to four heteroatoms, which may be the same or different, selected from nitrogen, oxygen, and sulfur" bonded to a carbonyl group via an amino group. Examples thereof can include aminocarbonyl groups of aromatic heterocyclic groups such as furylaminocarbonyl, thienylaminocarbonyl, pyrrolylaminocarbonyl, azepinylaminocarbonyl, pyrazolylaminocarbonyl, imidazolylaminocarbonyl, oxazolylaminocarbonyl, oxadiazolylaminocarbonyl, isoxazolylaminocarbonyl, thiazolylaminocarbonyl, isothiazolylaminocarbonyl, 1,2,3-oxadiazolylaminocarbonyl, triazolylaminocarbonyl, tetrazolylaminocarbonyl, thiadiazolylaminocarbonyl, pyranylaminocarbonyl, pyridylaminocarbonyl, pyridazinylaminocarbonyl, pyrimidinylaminocarbonyl, and pyrazinylaminocarbonyl groups.

In the present invention, the "halogeno group" refers to a fluoro, chloro, bromo, or iodo group. For $R^1$, $R^2$, $R^3$, $R^7$, $A^B$, $A^C$, $A^D$, $A^E$, $A^F$, $A^G$, $A^H$, or $A^J$, the halogeno group is preferably a fluoro, chloro, or bromo group.

Preferably, $R^1$ of the present invention is a hydrogen atom, a C1-6 alkyl group (wherein the alkyl group is optionally substituted by one hydroxy group or C1-6 alkoxy group), a C6-10 aryl group, or a 3- to 10-membered heterocyclyl group containing one to four heteroatoms, which may be the same or different, selected from nitrogen, oxygen, and sulfur.

Preferably, $R^2$ and $R^3$ of the present invention are the same or different and each represent a hydrogen atom or a C1-6 alkyl group (wherein the alkyl group is optionally substituted by one hydroxy group), or the C1-6 alkyl groups of $R^2$ and $R^3$ are bonded to each other to form a 3- to 6-membered saturated carbocyclic ring.

Preferably, each of $R^4$ and $R^5$ of the present invention is a hydrogen atom.

Preferably, $R^6$ of the present invention is a hydrogen atom.

Preferably, each $R^7$ of the present invention, which may be the same or different, represents a C1-6 alkoxy group (wherein the alkoxy group is optionally substituted by one to three halogeno groups) or a halogeno group.

The compound represented by the general formula (I) of the present invention can form a salt with a base. Such a salt with a base is included in the scope of the present invention. Examples of the salt with a base can include: alkali metal salts such as lithium salt, sodium salt, potassium salt, and cesium salt; alkaline earth metal salts such as magnesium salt, calcium salt, and barium salt; inorganic nitrogen compound salts such as ammonium salt and hydrazine salt; primary amine salts such as methylamine salt, ethylamine salt, n-propylamine salt, isopropylamine salt, n-butylamine salt, 2-butylamine salt, isobutylamine salt, and tert-butylamine salt; secondary amine salts such as dimethylamine salt, diethylamine salt, diisopropylamine salt, pyrrolidine salt, piperidine salt, and morpholine salt; tertiary amine salts such as triethylamine salt and N-methylmorpholine salt; and aromatic amine salts such as pyridine salt, 4-(N,N-dimethylamino)pyridine salt, imidazole salt, and 1-methylimidazole salt. The salt is preferably an alkali metal salt, most preferably sodium salt or potassium salt. The compound represented by the general formula (I) of the present invention can form any ratio of a salt with a base. The respective salts with bases or mixtures thereof are included in the scope of the present invention.

The compound represented by the general formula (I) of the present invention can form an acid-addition salt, depending on its substituent. Such an acid-addition salt is included in the scope of the present invention. The compound represented by the general formula (I) of the present invention can form any ratio of an acid-addition salt, depending on its substituent. The respective acid-addition salts (e.g., mono-acid salt and hemi-acid salt) or mixtures thereof are included in the salt of the present invention.

The compound represented by the general formula (I) of the present invention or the pharmacologically acceptable salt thereof can form an anhydrate, a hydrate, or a solvate. The respective forms or mixtures thereof are included in the scope of the present invention.

When the compound represented by the general formula (I) of the present invention or the pharmacologically acceptable salt thereof has at least one asymmetric center, carbon-carbon double bond, axial chirality, tautomerism, or the like, optical isomers (including enantiomers and diastereomers), geometric isomers, rotational isomers, and tautomers may exist. These isomers and mixtures thereof are represented by a single formula such as the formula (I). The present invention encompasses these isomers and mixtures (including racemates) thereof at any ratio.

The compound represented by the general formula (I) of the present invention or the pharmacologically acceptable salt thereof can form an isotopic compound by the replacement of one or more atoms constituting the compound or the salt with isotopes at nonnatural ratios. The isotopes can be radioactive or nonradioactive. Examples thereof include deuterium ($^2$H; D), tritium ($^3$H; T), carbon-14 ($^{14}$C), and iodine-125 ($^{125}$I). The radioactive or nonradioactive isotopic compound may be used as a pharmaceutical for the treatment or prophylaxis of a disease, a reagent for research (e.g., a reagent for assay), a diagnostic agent (e.g., a diagnostic imaging agent), or the like. The present invention encompasses these radioactive or nonradioactive isotopic compounds.

The compound represented by the general formula (I) of the present invention can be produced by, for example, the following method:

Method A:

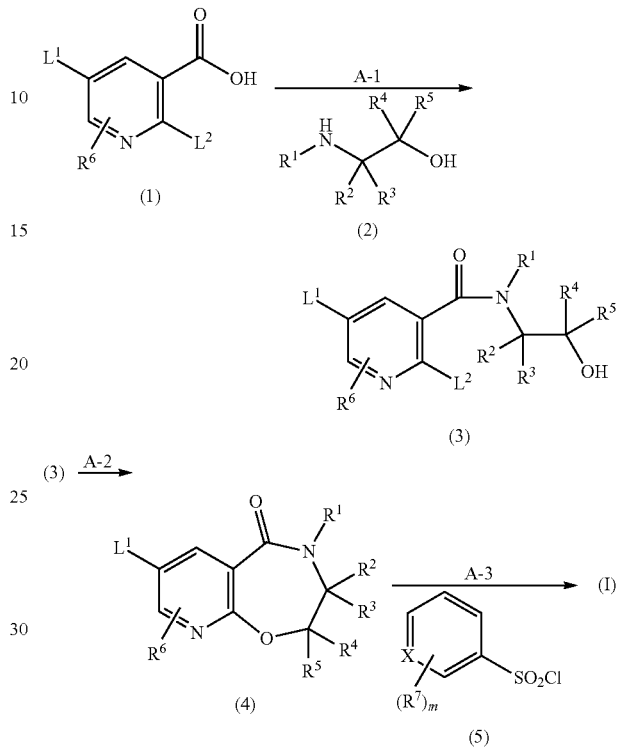

In the structural formulas of the compounds in the method A and the description below, $R^1$, $R^2$, $R^3$, $R^4$, $R^5$, $R^6$, $R^7$, m, and X are as defined in the formula (I);

$L^1$ represents a nitro group, a halogeno group, or an amino group and is preferably a nitro group or a bromo group; and $L^2$ represents a halogeno group and is preferably a chloro group.

When a compound serving as a reactive substrate in the reaction of each step in the method A has a group inhibiting the reaction of interest, such as an amino group, a hydroxy group, or a carboxyl group, an appropriate protective group may be introduced to the functional group and the introduced protective group may be removed, if necessary. Such a protective group is not particularly limited as long as the protective group is one usually used. The protective group can be a protective group described in, for example, T. W. Greene, P. G. M. Wuts, Protective Groups in Organic Synthesis, Fourth Edition, 2007, John Wiley & Sons, Inc. The reactions for the introduction and removal of these protective groups can be carried out according to routine methods such as methods described in the literature.

The solvent for use in the reaction of each step in the method A is not particularly limited as long as the solvent partially dissolves starting materials without inhibiting the reaction. The solvent is selected from, for example, the following solvent group: aliphatic hydrocarbons such as hexane, pentane, heptane, petroleum ether, and cyclohexane; aromatic hydrocarbons such as toluene, benzene, and xylene; halogenated hydrocarbons such as methylene chloride, chloroform, carbon tetrachloride, dichloroethane, chlorobenzene, and dichlorobenzene; ethers such as diethyl ether, diisopropyl ether, cyclopentylmethyl ether, t-butyl methyl ether, tetrahydrofuran, 1,4-dioxane, dimethoxyethane, and diethylene glycol dimethyl ether; ketones such as acetone, methyl ethyl ketone, methyl isobutyl ketone, and cyclohexanone; esters such as methyl acetate, ethyl acetate, propyl acetate, butyl acetate, and diethyl carbonate; nitriles such as acetonitrile, propionitrile, butyronitrile, and isobutyronitrile; organic acids such as formic acid, acetic acid, propionic acid, trifluoroacetic acid, and pentafluoropropionic acid; alcohols such as methanol, ethanol, 1-propanol, 2-propanol, 1-butanol, 2-butanol, 2-methyl-1-propanol, and 2-methyl-2-propanol; amides such as formamide, N,N-dimethylformamide, N,N-dimethylacetamide, N-methylpyrrolidone, N,N'-dimethylpropyleneurea, and hexamethylphosphortriamide; sulfoxides such as dimethyl sulfoxide and sulfolane; water; and mixtures thereof.

The acid for use in the reaction of each step in the method A mentioned below is not particularly limited as long as the acid does not inhibit the reaction. The acid is selected from the following acid group: inorganic acids such as hydrochloric acid, hydrobromic acid, hydroiodic acid, phosphoric acid, sulfuric acid, and nitric acid; organic acids such as formic acid, acetic acid, propionic acid, trifluoroacetic acid, and pentafluoropropionic acid; and organic sulfonic acids such as methanesulfonic acid, trifluoromethanesulfonic acid, p-toluenesulfonic acid, and camphorsulfonic acid.

The base for use in the reaction of each step in the method A mentioned below is not particularly limited as long as the base does not inhibit the reaction. The base is selected from the following base group: alkali metal carbonates such as lithium carbonate, sodium carbonate, potassium carbonate, and cesium carbonate; alkali metal bicarbonates such as lithium bicarbonate, sodium bicarbonate, and potassium bicarbonate; alkali metal hydroxides such as lithium hydroxide, sodium hydroxide, and potassium hydroxide; alkaline earth metal hydroxides such as calcium hydroxide and barium hydroxide; alkali metal phosphates such as sodium phosphate and potassium phosphate; alkali metal hydrides such as lithium hydride, sodium hydride, and potassium hydride; alkali metal amides such as lithium amide, sodium amide, and potassium amide; metal alkoxides such as lithium methoxide, sodium methoxide, sodium ethoxide, sodium tert-butoxide, and potassium tert-butoxide; lithium amides such as lithium diisopropylamide (LDA), lithium cyclohexylisopropylamide, and lithium tetramethylpiperazide; alkali metal silylamides such as lithium bistrimethylsilylamide, sodium bistrimethylsilylamide, and potassium bistrimethylsilylamide; alkyllithiums such as methyllithium, n-butyllithium, sec-butyllithium, and tert-butyllithium; alkyl magnesium halides such as methyl magnesium chloride, methyl magnesium bromide, methyl magnesium iodide, ethyl magnesium chloride, ethyl magnesium bromide, isopropyl magnesium chloride, isopropyl magnesium bromide, and isobutyl magnesium chloride; and organic amines such as triethylamine, tributylamine, diisopropylethylamine, diethylamine, diisopropylamine, N-methylpiperidine, N-methylmorpholine, N-ethylmorpholine, pyridine, picoline, 2,6-lutidine, 4-(N,N-dimethylamino)pyridine, N,N-dimethylaniline, N,N-diethylaniline, 1,5-diazabicyclo[4,3,0]non-5-ene, 1,4-diazabicyclo[2,2,2]octane (DABCO), and 1,8-diazabicyclo[5,4,0]-7-undecene (DBU).

In the reaction of each step in the method A mentioned below, the reaction temperature differs depending on solvents, starting materials, reagents, etc., and the reaction time differs depending on solvents, starting materials, reagents, etc.

After the completion of the reaction of each step in the method A mentioned below, the compound of interest of each step is isolated from the reaction mixture according to a routine method. The compound of interest is obtained, for example, by: (i) if necessary, filtering off insoluble matter such as a catalyst; (ii) adding water and a water-immiscible solvent (e.g., methylene chloride, chloroform, diethyl ether, ethyl acetate, or toluene) to the reaction mixture to extract the compound of interest; (iii) washing the organic layer with water, followed by drying using a desiccant such as anhydrous sodium sulfate or anhydrous magnesium sulfate; and (iv) distilling off the solvent. The obtained compound of interest can be further purified, if necessary, by a routine method, for example, recrystallization, reprecipitation, or silica gel column chromatography. Alternatively, the compound of interest of each step may be used directly in the next reaction without being purified.

In the reaction of each step in the method A mentioned below, optical isomers can be resolved by resolution using a chiral column.

Hereinafter, the reaction of each step in the method A will be described.

(Step A-1)

Step A-1 is the step of condensing compound (1) with compound (2) to produce compound (3). The compound (2) is known in the art or is easily obtained from a compound known in the art.

The method for condensing a carboxylic acid with an amine differs depending on the type of the carboxylic acid and can be generally carried out by a method well known in the techniques of organic synthetic chemistry, for example, a method described in Comprehensive Organic Transformations (Second Edition, 1999, John Wiley & Sons, Inc., pp. 1929-1930, 1941-1949, and 1953-1954). A preferred method involves converting the carboxylic acid to a corresponding acid halide, which is then condensed with a corresponding amine. Thus, step A-1 comprises:

(step A-1a): the step of reacting compound (1) with a halogenating agent; and (step A-1b): the step of reacting the compound obtained in the step A-1a with compound (2) in the presence of a base.

(Step A-1a)

Examples of the halogenating agent used can include: thionyl chloride, phosphorus trichloride, phosphorus oxychloride, phosphorus pentachloride, phosphorus tribromide, phosphorus pentabromide, oxalyl chloride, carbon tetrachloride-triphenylphosphine, hexachloroethane-triphenylphosphine, N-chlorosuccinimide-triphenylphosphine, carbon tetrabromide-triphenylphosphine, and N-bromosuccinimide-triphenylphosphine; and combinations of these halogenating agents with additives such as N,N-dimethylformamide. The halogenating agent is preferably a combination of thionyl chloride with an additive or a combination of oxalyl chloride with an additive, more preferably a combination of oxalyl chloride with N,N-dimethylformamide.

Examples of the solvent used can include aliphatic hydrocarbons, aromatic hydrocarbons, halogenated hydrocarbons, ethers, and esters. The solvent is preferably a halogenated hydrocarbon or an ether, more preferably methylene chloride or tetrahydrofuran.

The reaction temperature is preferably 0° C. to 100° C., more preferably room temperature.

The reaction time is preferably 15 minutes to 6 hours.

(Step A-1b)

Examples of the base used can include alkali metal carbonates, alkali metal bicarbonates, alkali metal hydrides, lithium amides, alkali metal silylamides, alkyllithiums, and organic amines. The base is preferably an organic amine, more preferably triethylamine or diisopropylethylamine.

Examples of the solvent used can include aliphatic hydrocarbons, aromatic hydrocarbons, halogenated hydrocarbons, ethers, esters, and amides. The solvent is preferably an ether or an amide, more preferably tetrahydrofuran or N,N-dimethylformamide.

The reaction temperature is preferably −78° C. to 100° C., more preferably −20° C. to room temperature.

The reaction time is preferably 15 minutes to 24 hours.

(Step A-2)

Step A-2 is the step of intramolecularly cyclizing the compound (3) obtained in the step A-1b in the presence of a base to produce compound (4). The compound (4) of interest of this step can also be converted, if necessary, to another compound (4) of interest through deprotection reaction. Alternatively, the compound (4) of interest of this step can also be converted, if necessary, to another compound (4) of interest through modification reaction on the nitrogen atom of the amide group.

Examples of the base used can include alkali metal carbonates, alkali metal bicarbonates, alkali metal hydrides, alkali metal hydroxides, alkaline earth metal hydroxides, alkali metal alkoxides, lithium amides, alkali metal silylamides, and organic amines. The base is preferably an alkali metal hydride, an alkali metal carbonate, an alkali metal silylamide, or an organic amine, more preferably sodium bistrimethylsilylamide, sodium hydride, potassium carbonate, or cesium carbonate.

Examples of the solvent used can include aliphatic hydrocarbons, aromatic hydrocarbons, halogenated hydrocarbons, alcohols, ethers, esters, nitriles, ketones, and amides. The solvent is preferably an ether, a nitrile, or an amide, more preferably tetrahydrofuran, acetonitrile, or N,N-dimethylformamide.

The reaction temperature is preferably −78° C. to 100° C.

The reaction time is preferably 15 minutes to 24 hours.

The reaction for converting the compound (4) of interest obtained in this step to another compound (4) of interest by the removal of the protective group differs depending on the type of the protective group and can be generally carried out according to a routine method such as a method well known in the techniques of organic synthetic chemistry, for example, a method described in T. W. Greene, P. G. M. Wuts, Protective Groups in Organic Synthesis, Fourth Edition, 2007, John Wiley & Sons, Inc.

The reaction for converting the compound (4) of interest obtained in this step to another compound (4) of interest through modification on the nitrogen atom of the amide group is not particularly limited as long as the reaction does not influence the other parts of the compound. This reaction can be carried out by, for example, a method described in Comprehensive Organic Transformations (Second Edition, 1999, John Wiley & Sons, Inc., pp. 1978-1982).

(Step A-3)

Step A-3 is the step of reacting the compound (4) obtained in the step A-2 with compound (5) in the presence of a base to produce compound (I). The compound (5) is known in the art or is easily obtained from a compound known in the art. The compound (I) of interest of this step can also be converted, if necessary, to another compound (I) of interest through deprotection reaction. The reaction for converting the obtained compound (I) of interest to another compound (I) of interest by the removal of the protective group is not particularly limited as long as the reaction does not influence the other parts of the compound. This reaction can be carried out according to a routine method, for example, a method described in T. W. Greene, P. G. M. Wuts, Protective Groups in Organic Synthesis, Fourth Edition, 2007, John Wiley & Sons, Inc.

Hereinafter, this step is referred to as step A-3-1 when $L^1$ is a nitro group, as step A-3-2 when $L^1$ is an amino group, and as step A-3-3 when $L^1$ is a halogeno group.

(Step A-3-1)

When $L^1$ is a nitro group, step A-3-1 comprises:

(step A-3-1a): the step of selectively reducing the nitro group of the compound obtained in the step A-2 into an amino group; and (step A-3-1b): the step of reacting the compound obtained in the step A-3-1a with compound (5) in the presence of a base to produce compound (I).

(Step A-3-1a)

The method for selectively reducing the nitro group is not particularly limited as long as the method does not influence the other parts of the compound. This method can be generally carried out by a method well known in the techniques of organic synthetic chemistry, for example, a method described in Comprehensive Organic Transformations (Second Edition, 1999, John Wiley & Sons, Inc., pp. 821-828). The method is preferably a catalytic reduction method or a method using a combination of a reducing agent and an additive.

Examples of the metal catalyst for use in the catalytic reduction method can include: palladium catalysts such as palladium on carbon, palladium black, palladium hydroxide on carbon, and palladium on barium sulfate; platinum catalysts such as platinum oxide and platinum black, platinum on carbon; rhodium catalysts such as rhodium on aluminum oxide and chlorotris(triphenylphosphine)rhodium (I); and nickel catalysts such as Raney nickel. The metal catalyst is preferably a palladium catalyst, more preferably 10% palladium on carbon.

The hydrogen pressure in the catalytic reduction method is preferably 1 to 10 atm, more preferably 1 atm.

The solvent for use in the catalytic reduction method is not particularly limited as long as the solvent is inert to this reaction. Examples thereof can include aliphatic hydrocarbons, aromatic hydrocarbons, halogenated hydrocarbons, alcohols, ethers, esters, nitriles, ketones, amides, and mixtures thereof. The solvent is preferably an alcohol, an ether, an amide, or a mixture thereof, more preferably methanol or a mixture of tetrahydrofuran and ethanol.

The reaction temperature in the catalytic reduction method is preferably room temperature to 60° C.

The reaction time in the catalytic reduction method is preferably 1 hour to 24 hours.

The combination of the reagents for use in the reaction using the combination of the reducing agent and the additive is preferably a combination of sodium borohydride and nickel(II) chloride hexahydrate, a combination of zinc powder and acetic acid, a combination of iron powder and acetic acid, or a combination of tin(II) chloride and hydrochloric acid, more preferably a combination of sodium borohydride and nickel(II) chloride hexahydrate.

The solvent for use in the reaction using the combination of the reducing agent and the additive is preferably a mixture of an alcohol and an ether, more preferably a mixture of tetrahydrofuran and methanol.

The reaction temperature in the reaction using the combination of the reducing agent and the additive is preferably 0° C. to room temperature.

The reaction time in the reaction using the combination of the reducing agent and the additive is preferably 5 minutes to 2 hours.

(Step A-3-1b)

Examples of the base used can include alkali metal carbonates, alkali metal bicarbonates, alkali metal hydrides, alkali metal hydroxides, alkali metal alkoxides, lithium amides, alkali metal silylamides, and organic amines. The base is preferably an organic amine, more preferably pyridine.

Examples of the solvent used can include aliphatic hydrocarbons, aromatic hydrocarbons, halogenated hydrocarbons, ethers, esters, nitriles, ketones, and amides. Alternatively, the solvent may not be used. Preferably, the solvent is not used.

The reaction temperature is preferably 0° C. to 100° C., more preferably room temperature to 80° C.

The reaction time is preferably 15 minutes to 24 hours, more preferably 30 minutes to 3 hours.

The reaction for converting the obtained compound (I) of interest obtained in this step to another compound (I) of interest by the removal of the protective group is not particularly limited as long as the reaction does not influence the other parts of the compound. This reaction can be carried out according to a routine method, for example, a method described in T. W. Greene, P. G. M. Wuts, Protective Groups in Organic Synthesis, Fourth Edition, 2007, John Wiley & Sons, Inc.

(Step A-3-2)

When $L^1$ is an amino group, the compound (I) can be produced according to the step A-3-1b.

(Step A-3-3)

When $L^1$ is a halogeno group, step A-3-3 comprises:

(step A-3-3a): the step of converting the bromo group of the compound produced in the step A-2 to a N-Boc amide group using a metal catalyst in the presence of a base;

(step A-3-3b): the step of deprotecting the N-Boc group of the compound obtained in the step A-3-3a to form an amino group; and (step A-3-3c): the step of reacting the compound obtained in the step A-3-3b with compound (5) in the presence of a base to produce compound (I).

(Step A-3-3a)

The method for converting the bromo group on the aromatic ring to a N-Boc amide group is not particularly limited as long as the method does not influence the other parts of the compound. This method can be carried out according to a method well known in the techniques of organic synthetic chemistry, for example, a method described in A. P. Dishington, P. D. Johnson, J. G. Kettle, Tetrahedron Letters, 45, 3733 (2004) or S. Bhagwanth, A. G. Waterson, G. M. Adjabeng, K. R. Hornberger, Journal of Organic Chemistry, 74, 4634 (2009).

The metal catalyst used is preferably a combination of tris(dibenzylideneacetone)dipalladium(0) chloroform complex and 9,9-dimethyl-4,5-bis(diphenylphosphino)xanthene (Xantphos™) or a combination of tris(dibenzylideneacetone)dipalladium(0) chloroform complex and di-tert-butyl (2',4',6'-triisopropylbiphenyl-2-yl)phosphine (tBuXPhos™).

The base used is preferably an alkali metal carbonate, an alkali metal phosphate, or an alkali metal alkoxide, more preferably potassium carbonate, cesium carbonate, potassium phosphate, or sodium tert-butoxide.

Examples of the solvent used can include aliphatic hydrocarbons, aromatic hydrocarbons, halogenated hydrocarbons, alcohols, ethers, esters, nitriles, ketones, amides, and mixtures thereof. The solvent is preferably an aromatic hydrocarbon, an ether, a nitrile, or an amide, more preferably toluene, 1,4-dioxane, acetonitrile, or N,N-dimethylformamide.

The reaction temperature is preferably room temperature to 100° C.

The reaction time is preferably 1 hour to 48 hours.

(Step A-3-3b)

The method for deprotecting the N-Boc group is not particularly limited as long as the method does not influence the other parts of the compound. This method can be carried out according to a routine method, for example, a method described in T. W. Greene, P. G. M. Wuts, Protective Groups in Organic Synthesis, Fourth Edition, 2007, John Wiley & Sons, Inc., pp. 725-735.

(Step A-3-3c)

The compound (I) can be produced according to the step A-3-1b.

When $L^1$ is a bromo group, the compound (I) can also be produced through the reaction of the compound (4) with the following compound (6):

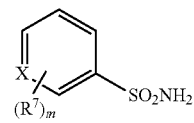

(6)

using a metal catalyst in the presence of a base.

The method for converting the bromo group on the aromatic ring to a benzenesulfonamide group is not particularly limited as long as the method does not influence the other parts of the compound. This method can be carried out according to a method well known in the techniques of organic synthetic chemistry, for example, a method described in X. Wang, A. Guram, M. Ronk, J. E. Milne, J. S. Tedrow, M. M. Faul, Tetrahedron Letters, 53, 7 (2012), W. Deng, L. Liu, C. Zhang, M. Liu, Q.-X. Guo, Tetrahedron Letters, 46, 7295 (2005), or D. K. Luci, J. B. Jameson, A. Yasgar, G. Diaz, N. Joshi, A. Kantz, K. Markham, S. Perry, N. Kuhn, J. Yeung, E. H. Kerns, L. Schultz, M. Holinstat, J. Nadler, D. A. Taylor-Fishwick, A. Jadhav, A. Simeonov, T. R. Holman, D. J. Maloney, Journal of Medicinal Chemistry, 57, 495 (2014).

The metal catalyst used is preferably a combination of copper(I) iodide and N-methyl-2-(methylamino)ethylamine.

The base used is preferably an alkali metal carbonate, an alkali metal phosphate, or an alkali metal alkoxide, more preferably potassium carbonate or cesium carbonate.

Examples of the solvent used can include aliphatic hydrocarbons, aromatic hydrocarbons, halogenated hydrocarbons, alcohols, ethers, esters, nitriles, ketones, amides, and mixtures thereof. The solvent is preferably an aromatic hydrocarbon, an ether, a nitrile, or an amide, more preferably xylene, 1,4-dioxane, acetonitrile, or N,N-dimethylformamide.

The reaction temperature is preferably room temperature to 100° C.

The reaction time is preferably 1 hour to 48 hours.

When the compound represented by the general formula (I) of the present invention or the pharmacologically acceptable salt thereof is used as a pharmaceutical, the compound or the salt can be administered alone (i.e., as a bulk) or can be administered orally as an appropriate pharmaceutically acceptable preparation such as a tablet, a capsule, granules, a powder, or a syrup or parenterally as an appropriate pharmaceutically acceptable preparation such as an injection, a suppository, or a patch (preferably orally).

These preparations are produced by well-known methods using additives such as excipients, binders, disintegrants, lubricants, emulsifiers, stabilizers, corrigents, diluents, solvents for injections, oleaginous bases, and water-soluble bases.

Examples of the excipients can include organic excipients and inorganic excipients. Examples of the organic excipients can include: sugar derivatives such as lactose, saccharose, glucose, mannitol, and sorbitol; starch derivatives such as corn starch, potato starch, α-starch, dextrin, and carboxymethyl starch; cellulose derivatives such as crystalline cellulose, low-substituted hydroxypropylcellulose, hydroxypropylmethylcellulose, carboxymethylcellulose, carboxymethylcellulose calcium, and internally cross-linked carboxymethylcellulose sodium; gum arabic; dextran; and pullulan. Examples of the inorganic excipients can include: light anhydrous silicic acid and silicate derivatives such as synthetic aluminum silicate and calcium silicate; phosphates such as calcium phosphate; and sulfates such as calcium sulfates.

Examples of the binders can include: the excipients listed above; gelatin; polyvinylpyrrolidone; and polyethylene glycol.

Examples of the disintegrants can include: the excipients listed above; chemically modified starch or cellulose derivatives such as croscarmellose sodium and carboxymethyl starch sodium; and cross-linked polyvinylpyrrolidone.

Examples of the lubricants can include: talc; stearic acid; stearic acid metal salts such as calcium stearate and magnesium stearate; colloidal silica; waxes such as bees wax and spermaceti; boric acid; glycol; D,L-leucine; carboxylic acids such as fumaric acid and adipic acid; carboxylic acid sodium salts such as sodium benzoate; sulfates such as sodium sulfate; lauryl sulfates such as sodium lauryl sulfate and magnesium lauryl sulfate; silicic acids such as silicic anhydride and silicic acid hydrate; and the starch derivatives listed as the excipients.

Examples of the emulsifiers can include: colloidal clay such as bentonite and veegum; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester, and sucrose fatty acid ester.

Examples of the stabilizers can include: p-hydroxybenzoic acid esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid.

Examples of the corrigents can include sweeteners, acidulants, and flavors usually used.

Examples of the diluents can include water, ethanol, propylene glycol, ethoxylated isostearyl alcohol, and polyoxyethylene sorbitan fatty acid esters.

Examples of the solvents for injections can include water, ethanol, and glycerin.

Examples of the oleaginous bases can include cacao butter, laurin butter, coconut oil, palm kernel oil, camellia oil, liquid paraffin, white petrolatum, purified lanoline, glycerin monostearate, polyoxyethylene hydrogenated castor oil, sorbitan fatty acid ester, sucrose fatty acid ester, stearyl alcohol, and cetanol.

Examples of the water-soluble bases can include glycerin, polyethylene glycol, ethanol, and purified water.

The dose of the compound represented by the general formula (I) of the present invention or the pharmacologically acceptable salt thereof serving as an active ingredient differs depending on the symptoms and age of a patient, etc. The single dose thereof is 0.001 mg/kg (preferably 0.01 mg/kg) as the lower limit and 10 mg/kg (preferably 1 mg/kg) as the upper limit for oral administration and 0.001 mg/kg (preferably 0.01 mg/kg) as the lower limit and 10 mg/kg (preferably 1 mg/kg) as the upper limit for parenteral administration and can be administered once to six times a day according to the symptoms.

The compound of the present invention can be used in combination with any of various therapeutic or prophylactic agents for the aforementioned disease for which the compound of the present invention is probably effective. In this combined use, the compound of the present invention and the agent may be administered simultaneously, separately but continuously, or at the desired time interval. The preparations to be administered simultaneously may be formulated as a combination drug or formulated as separate preparations.

The pyridine compound or the pharmacologically acceptable salt thereof, which is the compound of the present invention, has an excellent TNAP inhibitory effect and is useful as a therapeutic or prophylactic agent for pseudoxanthoma elasticum (PXE), generalized arterial calcification of infancy (GACI), craniometaphyseal dysplasia (CMD), ossification of the yellow ligament (OYL), arterial calcification due to deficiency of CD73 (ACDC), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, or peritoneal calcification. Moreover, the compound of the present invention has low toxicity and excellent safety and as such, is very useful as a pharmaceutical.

DETAILED DESCRIPTION OF THE PREFERRED EMBODIMENTS

Hereinafter, the present invention will be described in more detail with reference to Examples, etc. However, the scope of the present invention is not intended to be limited by them.

The chemical structural formulas described in Examples represent the chemical structures of corresponding compounds in a free form.

Elution in column chromatography in Examples was carried out under observation by thin layer chromatography (TLC). In the TLC observation, silica gel 60$F_{254}$ manufactured by Merck KGaA was used as a TLC plate; a solvent used as an eluting solvent in column chromatography was used as a developing solvent; and a UV detector or a chromogenic method using a coloring agent (e.g., a ninhydrin coloring solution, an anisaldehyde coloring solution, an ammonium phosphomolybdate coloring solution, a cerium ammonium nitrate (CAM) coloring solution, or an alkaline permanganate coloring solution) was used as a detection method. Silica gel SK-85 (230-400 mesh) also manufactured by Merck KGaA, silica gel 60 N (40-50 μm) manufactured by Kanto Chemical Co., Inc., or Chromatorex NH (200-350 mesh) manufactured by Fuji Silysia Chemical Ltd. was used as silica gel for columns. In addition to general column chromatography, an automatic chromatography apparatus (Purif-α2 or Purif-espoir2) manufactured by Shoko Scientific Co., Ltd., an automatic chromatography apparatus (W-Prep 2XY) manufactured by Yamazen Corp., an automatic chromatography apparatus (Isolera One) manufactured by Biotage Japan Ltd., or an automatic chromatography apparatus (CombiFlash Rf) manufactured by Teledyne Isco, Inc. was appropriately used. The eluting solvent was determined on the basis of the TLC observation.

In Examples, nuclear magnetic resonance ($^1$H NMR) spectra were indicated by chemical shift δ values (ppm) determined with tetramethylsilane as a standard. Splitting patterns were indicated by s for singlet, d for doublet, t for triplet, q for quartet, m for multiplet, and br for broad. Mass spectrometry (hereinafter, referred to as MS) was conducted by the electron ionization (EI), electron spray ionization (ESI), atmospheric pressure chemical ionization (APCI), electron spray atmospheric pressure chemical ionization (ES/APCI), or fast atom bombardment (FAB) method.

In each step of Examples, the adjustment of a reaction solution and reaction were carried out at room temperature unless the temperature is otherwise specified.

EXAMPLES (Example 1) 5-Chloro-2-methoxy-N-(4-methyl-5-oxo-2,3,4,5-tetrahydropyrido[3,2-f][1,4]oxazepin-7-yl)benzenesulfonamide

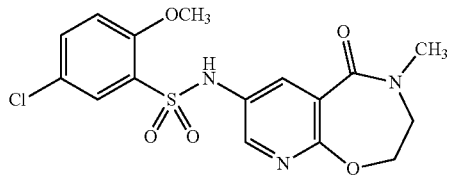 [SMILES: COc1ccc(Cl)cc1S(=O)(=O)Nc1cnc2c(c1)C(=O)N(C)CCO2]

(1a) 2-Chloro-N-(2-hydroxyethyl)-N-methyl-5-nitro-pyridine-3-carboxamide

To a suspension of 2-chloro-5-nitropyridine-3-carboxylic acid (500 mg, 2.47 mmol) in methylene chloride (10 mL), oxalyl chloride (0.28 mL, 3.3 mmol) and N,N-dimethylformamide (0.05 mL, 0.64 mmol) were added at room temperature, and the mixture was stirred at the same temperature as above for 2 hours. The reaction mixture was concentrated under reduced pressure to prepare a crude product of 2-chloro-5-nitropyridine-3-carboxylic acid chloride. To a solution of 2-(methylamino)ethanol (0.197 mL, 2.47 mmol) and N,N-diisopropylethylamine (0.84 mL, 4.9 mmol) in tetrahydrofuran (5 mL), a solution of the crude product of 2-chloro-5-nitropyridine-3-carboxylic acid chloride in tetrahydrofuran (5 mL) was added over 10 minutes under ice cooling, and the mixture was stirred at room temperature for 1 hour. The reaction mixture was diluted with ethyl acetate, washed with a saturated aqueous solution of sodium chloride, and dried over anhydrous sodium sulfate. After filtration, the solvent was distilled off under reduced pressure, and the residue was purified in an automatic chromatography apparatus (n-hexane/ethyl acetate=100/0-0/100) to obtain the title compound (494.3 mg, yield: 77%).

$^1$H NMR spectrum (CDCl$_3$, 400 MHz) δ: 9.30-9.22 (1H, m), 8.58-8.46 (1H, m), 4.00-3.68 (4H, m), 3.24-2.99 (3H, m).

(1b) 4-Methyl-7-nitro-3,4-dihydropyrido[3,2-f][1,4]oxazepin-5(2H)-one

To a suspension of 2-chloro-N-(2-hydroxyethyl)-N-methyl-5-nitropyridine-3-carboxamide (259.2 mg, 1.00 mmol) obtained in Example (1a) in tetrahydrofuran (50 mL), sodium hydride (63% content, 68.8 mg, 1.81 mmol) was added under ice cooling, and the mixture was stirred at room temperature for 22 hours. The reaction mixture was cooled in an ice water bath. A 1 N aqueous sodium hydroxide solution (10 mL) was added thereto, and the mixture was stirred at room temperature for 20 minutes. The reaction mixture was diluted by addition of ethyl acetate, and the organic layer was separated and dried over anhydrous sodium sulfate. After filtration, the solvent was distilled off under reduced pressure to obtain the title compound (173.3 mg, yield: 78%).

$^1$H NMR spectrum (CDCl$_3$, 400 MHz) δ: 9.35 (1H, d, J=3.0 Hz), 9.23 (1H, d, J=3.0 Hz), 4.76-4.70 (2H, m), 3.83-3.73 (2H, m), 3.27 (3H, s).

(1c) 7-Amino-4-methyl-3,4-dihydropyrido[3,2-f][1,4]oxazepin-5(2H)-one

To a mixture of 4-methyl-7-nitro-3,4-dihydropyrido[3,2-f][1,4]oxazepin-5(2H)-one (173.3 mg, 0.78 mmol) obtained in Example (1b) in tetrahydrofuran (5 L) and methanol (5 mL), nickel(II) chloride hexahydrate (386 mg, 1.62 mmol) was added. Subsequently, the mixture was cooled in an ice water bath. Sodium borohydride (122 mg, 3.22 mmol) was added thereto over 10 minutes, and then, the mixture was stirred at room temperature for 30 minutes. The reaction mixture was diluted by addition of acetone and a saturated aqueous solution of sodium bicarbonate, further Celite 545 (R) (approximately 0.6 g) was added thereto, and the mixture was stirred at room temperature for 30 minutes. The reaction mixture was filtered, and the filtrate was concentrated under reduced pressure. The residue was purified by reverse-phase silica gel column chromatography (Chromatorex ODS 100-200 mesh 50 mL, water/methanol=100/0-70/30) to obtain the title compound (96.4 mg, yield: 64%).

$^1$H NMR spectrum (CD$_3$OD, 400 MHz) δ: 7.77 (1H, d, J=3.0 Hz), 7.47 (1H, d, J=3.0 Hz), 4.44 (2H, t, J=5.2 Hz), 3.61 (2H, t, J=5.2 Hz), 3.19 (3H, s).

(1d) 5-Chloro-2-methoxy-N-(4-methyl-5-oxo-2,3,4,5-tetrahydropyrido[3,2-f][1,4]oxazepin-7-yl)benzenesulfonamide To a mixture of 7-amino-4-methyl-3,4-dihydropyrido[3,2-f][1,4]oxazepin-5(2H)-one (40.0 mg, 0.21 mmol) obtained in Example (1c) and pyridine (1.0 mL, 12.4 mmol), 5-chloro-2-methoxybenzenesulfonyl chloride (56.5 mg, 0.23 mmol) was added, and the mixture was stirred at 80° C. for 2 hours in an oil bath. The reaction mixture was cooled and then concentrated under reduced pressure, and the residue was purified in an automatic chromatography apparatus (ethyl acetate/methanol=100/0-80/20). The obtained solid was suspended by the addition of diisopropyl ether (1 mL), and then, the solid was collected by filtration and dried to obtain the title compound (31.9 mg, yield: 39%).

$^1$H NMR spectrum (CDCl$_3$, 400 MHz) δ: 8.28 (1H, d, J=2.4 Hz), 8.08 (1H, d, J=3.0 Hz), 7.74 (1H, d, J=2.4 Hz), 7.47 (1H, dd, J=8.8, 2.7 Hz), 7.02-6.98 (2H, m), 4.53 (2H, t, J=4.6 Hz), 4.08 (3H, s), 3.64 (2H, t, J=4.3 Hz), 3.19 (3H, s).

MS spectrum (ES/APCI⁺): 398 (M+H), 400 (M+2+H).

(Example 2) 5-Fluoro-2-methoxy-N-(4-methyl-5-oxo-2,3,4,5-tetrahydropyrido[3,2-f][1,4]oxazepin-7-yl)benzenesulfonamide

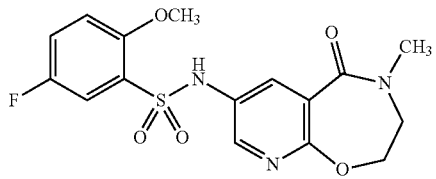 [SMILES: COc1ccc(F)cc1S(=O)(=O)Nc1cnc2c(c1)C(=O)N(C)CCO2]

To a mixture of 7-amino-4-methyl-3,4-dihydropyrido[3,2-f][1,4]oxazepin-5(2H)-one (96.4 mg, 0.50 mmol) obtained in Example (1c) and pyridine (2.0 mL, 24.9 mmol), 5-fluoro-2-methoxybenzenesulfonyl chloride (124.4 mg, 0.56 mmol) was added, and the mixture was stirred at 80° C. for 70 minutes in an oil bath. The reaction mixture was cooled and then concentrated under reduced pressure, and the residue was purified in an automatic chromatography apparatus (ethyl acetate/methanol=100/0-85/15). The obtained solid was suspended by the addition of diisopropyl ether (1 mL), and then, the solid was collected by filtration and dried to obtain the title compound (145.4 mg, yield: 76%).

¹H NMR spectrum (CDCl₃, 400 MHz) δ: 8.27 (1H, d, J=2.4 Hz), 8.08 (1H, d, J=3.0 Hz), 7.50 (1H, dd, J=7.3, 3.0 Hz), 7.25-7.20 (1H, m), 7.07 (1H, s), 7.02 (1H, dd, J=9.1, 4.3 Hz), 4.52 (2H, t, J=4.6 Hz), 4.06 (3H, s), 3.63 (2H, t, J=4.6 Hz), 3.19 (3H, s).

MS spectrum (ES/APCI⁺): 382 (M+H).

(Example 3) 5-Chloro-N-(4-ethyl-5-oxo-2,3,4,5-tetrahydropyrido[3,2-f][1,4]oxazepin-7-yl)-2-methoxybenzenesulfonamide

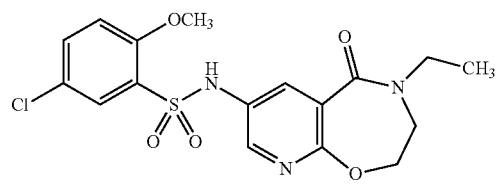 [SMILES: CCN1CCOc2ncc(NS(=O)(=O)c3cc(Cl)ccc3OC)cc2C1=O]

(3a) 4-Ethyl-7-nitro-3,4-dihydropyrido[3,2-f][1,4]oxazepin-5(2H)-one

The title compound (288 mg, yield for 2 steps: 49%) was obtained by production according to Examples (1a) and (1b) using 2-chloro-5-nitropyridine-3-carboxylic acid (502 mg, 2.47 mmol) and 2-(ethylamino)ethanol (223 mg, 2.50 mmol) as starting materials.

¹H NMR spectrum (CDCl₃, 400 MHz) δ: 9.34 (1H, d, J=3.0 Hz), 9.22 (1H, d, J=3.0 Hz), 4.71-4.69 (2H, m), 3.76-3.74 (2H, m), 3.69 (2H, q, J=7.3 Hz), 1.26 (3H, t, J=7.3 Hz).

(3b) 7-Amino-4-ethyl-3,4-dihydropyrido[3,2-f][1,4]oxazepin-5(2H)-one

A mixture of 4-ethyl-7-nitro-3,4-dihydropyrido[3,2-f][1,4]oxazepin-5(2H)-one (288 mg, 1.22 mmol) obtained in Example (3a) and 10% palladium carbon (water content: 54.6%, 31 mg) in methanol (15 mL) was stirred at room temperature for 5 hours at normal pressure under the hydrogen atmosphere. Hydrogen in the reaction container was replaced with nitrogen, and then, the reaction mixture was filtered through pad of Celite 545(R). The solvent in the filtrate was distilled off under reduced pressure to obtain the title compound (247 mg, yield: 98%).

¹H NMR spectrum (CDCl₃, 400 MHz) δ: 7.88 (1H, d, J=3.0 Hz), 7.60 (1H, d, J=3.0 Hz), 4.47 (2H, t, J=4.9 Hz), 3.68-3.63 (4H, m), 3.55 (2H, t, J=4.9 Hz), 1.25 (3H, t, J=7.3 Hz).

(3c) 5-Chloro-N-(4-ethyl-5-oxo-2,3,4,5-tetrahydropyrido[3,2-f][1,4]oxazepin-7-yl)-2-methoxybenzenesulfonamide The title compound (222 mg, yield: 90%) was obtained by production according to Example (1d) using 7-amino-4-ethyl-3,4-dihydropyrido[3,2-f][1,4]oxazepin-5(2H)-one (124 mg, 0.60 mmol) obtained in Example (3b) and 5-chloro-2-methoxybenzenesulfonyl chloride (159 mg, 0.66 mmol).

¹H NMR spectrum (CDCl₃, 400 MHz) δ: 8.26 (1H, d, J=2.4 Hz), 8.07 (1H, d, J=3.0 Hz), 7.74 (1H, d, J=2.4 Hz), 7.47 (1H, dd, J=8.8, 2.7 Hz), 7.05-6.98 (2H, m), 4.52 (2H, t, J=4.3 Hz), 4.08 (3H, s), 3.65-3.59 (4H, m), 1.22 (3H, t, J=7.0 Hz).

MS spectrum (ES/APCI⁺): 412 (M+H), 414 (M+2+H).

(Example 4) N-(4-Ethyl-5-oxo-2,3,4,5-tetrahydropyrido[3,2-f][1,4]oxazepin-7-yl)-5-fluoro-2-methoxybenzenesulfonamide

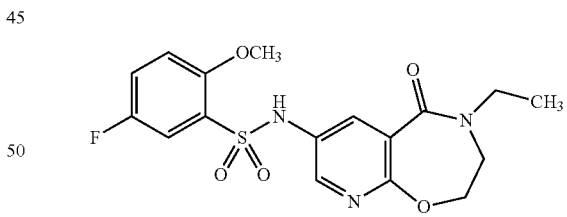

The title compound (206 mg, yield: 88%) was obtained by production according to the method described in Example (1d) using 7-amino-4-ethyl-3,4-dihydropyrido[3,2-f][1,4]oxazepin-5(2H)-one (123 mg, 0.59 mmol) obtained in Example (3b) and 5-fluoro-2-methoxybenzenesulfonyl chloride (150 mg, 0.67 mmol).

¹H NMR spectrum (CDCl₃, 400 MHz) δ: 8.26 (1H, d, J=3.0 Hz), 8.08 (1H, d, J=2.4 Hz), 7.50 (1H, dd, J=7.6, 3.3 Hz), 7.25-7.21 (1H, m), 7.10-7.07 (1H, m), 7.02 (1H, dd, J=9.1, 3.6 Hz), 4.51 (2H, t, J=4.6 Hz), 4.06 (3H, s), 3.65-3.58 (4H, m), 1.22 (3H, t, J=7.3 Hz).

MS spectrum (ES/APCI⁺): 396 (M+H).

(Example 5) 5-Chloro-2-methoxy-N-[5-oxo-4-(propan-2-yl)-2,3,4,5-tetrahydropyrido[3,2-f][1,4]oxazepin-7-yl]benzenesulfonamide

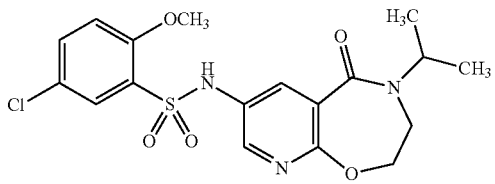 [SMILES: COc1ccc(Cl)cc1S(=O)(=O)Nc1cnc2c(c1)C(=O)N(C(C)C)CCO2]

(5a) 5-Chloro-2-methoxybenzenesulfonamide

To a solution of 5-chloro-2-methoxybenzenesulfonyl chloride (3 g, 12.4 mmol) in tetrahydrofuran (20 mL), a 28% aqueous ammonia solution (20 mL, 295 mmol) was added, and the mixture was stirred at room temperature for 19 hours. The reaction mixture was diluted by addition of 1 N hydrochloric acid, followed by extraction with ethyl acetate. The organic layer was washed with water and a saturated aqueous solution of sodium chloride and dried over anhydrous sodium sulfate. After filtration, the solvent was distilled off under reduced pressure to obtain the title compound (2.74 g, yield: quantitative).

$^1$H NMR spectrum (CDCl3, 400 MHz) δ: 7.91 (1H, d, J=3.0 Hz), 7.56-7.46 (1H, m), 7.00 (1H, d, J=8.5 Hz), 5.06 (2H, br s), 4.02 (3H, s).

(5b) 5-Bromo-2-chloro-N-(2-hydroxyethyl)-N-(propan-2-yl)pyridine-3-carboxamide The title compound (1.20 g, yield: 88%) was obtained by production according to the method described in Example (1a) using 5-bromo-2-chloropyridine-3-carboxylic acid (1.00 g, 4.22 mmol) and 2-(propan-2-ylamino)ethanol (481 mg, 4.66 mmol).

$^1$H NMR spectrum (CDCl$_3$, 400 MHz) δ: 8.51-8.46 (1H, m), 7.82-7.73 (1H, m), 3.96-3.85 (2H, m), 3.72-3.54 (3H, m), 3.31-3.25 (1H, m), 1.38-1.09 (6H, m).

(5c) 7-Bromo-4-(propan-2-yl)-3,4-dihydropyrido[3,2-f][1,4]oxazepin-5(2H)-one To a solution of 5-bromo-2-chloro-N-(2-hydroxyethyl)-N-(propan-2-yl)pyridine-3-carboxamide (600 mg, 1.87 mmol) obtained in Example (5b) in N,N-dimethylformamide (20 mL), sodium hydride (63% content, 141 mg, 3.70 mmol) was added under ice cooling, and the mixture was stirred at 80° C. for 3 hours and 20 minutes in an oil bath. The reaction mixture was cooled and diluted by addition of a saturated aqueous solution of sodium chloride, followed by extraction with ethyl acetate. The organic layer was washed with a 5% aqueous sodium chloride solution three times and dried over anhydrous sodium sulfate. After filtration, the solvent was distilled off under reduced pressure, and the residue was purified in an automatic chromatography apparatus (hexane/ethyl acetate=100/0-0/100) to obtain the title compound (142 mg, yield: 27%).

$^1$H NMR spectrum (CDCl$_3$, 400 MHz) δ: 8.48-8.47 (1H, m), 8.43-8.42 (1H, m), 5.06-4.99 (1H, m), 4.52 (2H, t, J=4.6 Hz), 3.52 (2H, t, J=4.6 Hz), 1.21 (6H, d, J=6.7 Hz).

(5d) 5-Chloro-2-methoxy-N-[5-oxo-4-(propan-2-yl)-2,3,4,5-tetrahydropyrido[3,2-f][1,4]oxazepin-7-yl]benzenesulfonamide A mixture of 7-bromo-4-(propan-2-yl)-3,4-dihydropyrido[3,2-f][1,4]oxazepin-5(2H)-one (142 mg, 0.50 mmol) obtained in Example (5c), 5-chloro-2-methoxybenzenesulfonamide (114 mg, 0.51 mmol) obtained in Example (5a), potassium carbonate (145 mg, 1.05 mmol), N,N'-dimethylethylene-1,2-diamine (0.27 mL, 2.5 mmol), and copper(I) iodide (48.8 mg, 0.26 mmol) in acetonitrile (5 mL) was heated to reflux for 6 hours and 30 minutes in an oil bath. The reaction mixture was cooled, diluted by addition of 1 N hydrochloric acid, and then stirred at room temperature for 30 minutes. The reaction mixture was filtered through pad of Celite 545(R), and the filtrate was subjected to extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-85/15). The obtained solid was suspended by the addition of diisopropyl ether, and then, the solid was collected by filtration and dried to obtain the title compound (44.4 mg, yield: 21%).

$^1$H NMR spectrum (CDCl$_3$, 400 MHz) δ: 8.25 (1H, d, J=2.4 Hz), 8.03 (1H, d, J=2.4 Hz), 7.75 (1H, d, J=3.0 Hz), 7.48 (1H, dd, J=8.8, 2.7 Hz), 7.02-6.98 (2H, m), 5.02-4.95 (1H, m), 4.47 (2H, t, J=4.6 Hz), 4.08 (3H, s), 3.48 (2H, t, J=4.6 Hz), 1.19 (6H, d, J=6.7 Hz).

MS spectrum (ES/APCI$^+$): 426 (M+H), 428 (M+2+H).

(Example 6) 5-Chloro-N-[4-(2-hydroxyethyl)-5-oxo-2,3,4,5-tetrahydropyrido[3,2-f][1,4]oxazepin-7-yl]-2-methoxybenzenesulfonamide

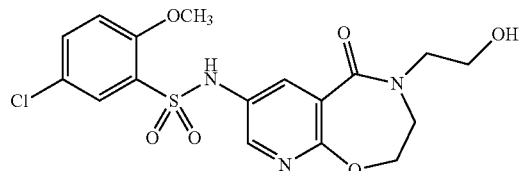

(6a) 4-(2-Hydroxyethyl)-7-nitro-3,4-dihydropyrido[3,2-f][1,4]oxazepin-5(2H)-one The title compound (318 mg, yield for 2 steps: 51%) was obtained by production according to the method described in Examples (1a) and (1b) using 2-chloro-5-nitropyridine-3-carboxylic acid (501 mg, 2.47 mmol) and 2,2-iminodiethanol (257 mg, 2.44 mmol).

$^1$H NMR spectrum (CDCl$_3$, 400 MHz) δ: 9.24 (1H, d, J=2.4 Hz), 8.56 (1H, d, J=2.4 Hz), 4.23-4.14 (1H, m), 4.06-3.96 (1H, m), 3.90-3.82 (2H, m), 3.73-3.59 (2H, m), 3.44-3.32 (1H, m), 3.06-3.00 (1H, m), 2.53-2.47 (1H, m).

(6b) 7-Amino-4-(2-hydroxyethyl)-3,4-dihydropyrido[3,2-f][1,4]oxazepin-5(2H)-one The title compound (125 mg, yield: 90%) was obtained by production according to the method described in Example (3c) using 4-(2-hydroxyethyl)-7-nitro-3,4-dihydropyrido[3,2-f][1,4]oxazepin-5(2H)-one (158 mg, 0.62 mmol) obtained in Example (6a).

$^1$H NMR spectrum (CDCl$_3$, 400 MHz) δ: 7.90 (1H, d, J=3.0 Hz), 7.58 (1H, d, J=3.0 Hz), 4.52 (2H, t, J=4.9 Hz), 3.92-3.88 (2H, m), 3.81-3.78 (2H, m), 3.68-3.65 (3H, m).

(6c) 5-Chloro-N-[4-(2-hydroxyethyl)-5-oxo-2,3,4,5-tetrahydropyrido[3,2-f][1,4]oxazepin-7-yl]-2-methoxybenzenesulfonamide The title compound (199 mg, yield: 83%) was obtained by production according to Example (1d) using 7-amino-4-(2-hydroxyethyl)-3,4-dihydropyrido[3,2-f][1,4]oxazepin-5(2H)-one (125 mg, 0.56 mmol) obtained in Example (6b) and 5-chloro-2-methoxybenzenesulfonyl chloride (150 mg, 0.62 mmol).

$^1$H NMR spectrum (DMSO-d6, 400 MHz) δ: 10.34 (1H, s), 8.08 (1H, d, J=3.0 Hz), 7.94 (1H, d, J=3.0 Hz), 7.70-7.62 (2H, m), 7.26 (1H, dd, J=10.9, 2.4 Hz), 4.82-4.79 (1H, m), 4.44 (2H, t, J=4.6 Hz), 3.87 (3H, s), 3.63 (2H, t, J=4.6 Hz), 3.59-3.51 (4H, m).

MS spectrum (ES/APCI$^+$): 428 (M+H), 430 (M+2+H).

(Example 7) 5-Chloro-2-methoxy-N-[4-(2-methoxyethyl)-5-oxo-2,3,4,5-tetrahydropyrido[3,2-f][1,4]oxazepin-7-yl]benzenesulfonamide

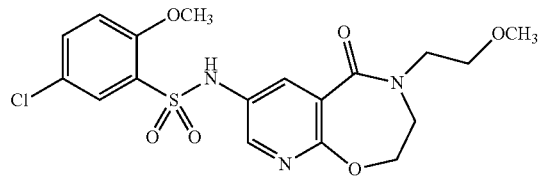 [SMILES: COCCN1CCOc2ncc(NS(=O)(=O)c3cc(Cl)ccc3OC)cc2C1=O]

(7a) 4-(2-Methoxyethyl)-7-nitro-3,4-dihydropyrido[3,2-f][1,4]oxazepin-5(2H)-one

To a solution of 4-(2-hydroxyethyl)-7-nitro-3,4-dihydropyrido[3,2-f][1,4]oxazepin-5(2H)-one (158 mg, 0.62 mmol) obtained in Example (6a) in tetrahydrofuran (4 mL), methyl iodide (0.062 mL, 1.0 mmol) and sodium hydride (63%, 32 mg, 0.84 mmol) were added under ice cooling, and the mixture was stirred at room temperature for 4 hours. To the mixture, methyl iodide (0.1 mL, 1.6 mmol) and sodium hydride (63%, 80 mg, 2.1 mmol) were further added, and the mixture was stirred at room temperature for 20 hours. Methyl iodide (0.1 mL, 1.6 mmol) and sodium hydride (63%, 60 mg, 1.6 mmol) were further added thereto, and the mixture was stirred at room temperature for 7 hours and 30 minutes. The reaction mixture was diluted by addition of a saturated aqueous solution of sodium chloride, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-85/15) to obtain the title compound (76.7 mg, yield: 46%).

$^1$H NMR spectrum (CDCl$_3$, 400 MHz) δ: 9.30 (1H, d, J=3.0 Hz), 9.23 (1H, d, J=3.0 Hz), 4.72 (2H, t, J=3.9 Hz), 3.87-3.84 (2H, m), 3.81 (2H, t, J=4.9 Hz), 3.65 (2H, t, J=4.9 Hz), 3.37 (3H, s).

(7b) 7-Amino-4-(2-methoxyethyl)-3,4-dihydropyrido[3,2-f][1,4]oxazepin-5(2H)-one

The title compound (65.3 mg, yield: 96%) was obtained by production according to the method described in Example (3c) using 4-(2-methoxyethyl)-7-nitro-3,4-dihydropyrido[3,2-f][1,4]oxazepin-5(2H)-one (76.7 mg, 0.29 mmol) obtained in Example (7a).

$^1$H NMR spectrum (CDCl$_3$, 400 MHz) δ: 7.88 (1H, d, J=3.0 Hz), 7.58 (1H, d, J=3.0 Hz), 4.49 (2H, t, J=5.2 Hz), 3.78 (2H, t, J=4.9 Hz), 3.67-3.61 (6H, m), 3.37 (3H, s).

(7c) 5-Chloro-2-methoxy-N-[4-(2-methoxyethyl)-5-oxo-2,3,4,5-tetrahydropyrido[3,2-f][1,4]oxazepin-7-yl]benzenesulfonamide The title compound (86.9 mg, yield: 72%) was obtained by production according to Example (1d) using 7-amino-4-(2-methoxyethyl)-3,4-dihydropyrido[3,2-f][1,4]oxazepin-5(2H)-one (65.3 mg, 0.28 mmol) obtained in Example (7b) and 5-chloro-2-methoxybenzenesulfonyl chloride (81.5 mg, 0.34 mmol).

$^1$H NMR spectrum (CDCl$_3$, 400 MHz) δ: 8.25 (1H, d, J=2.4 Hz), 8.07 (1H, d, J=2.4 Hz), 7.75 (1H, d, J=2.4 Hz), 7.47 (1H, dd, J=8.8, 2.7 Hz), 7.15-7.11 (1H, m), 7.00 (1H, d, J=8.5 Hz), 4.56-4.52 (2H, m), 4.06 (3H, s), 3.76-3.70 (4H, m), 3.61 (2H, t, J=4.9 Hz), 3.35 (3H, s).

MS spectrum (ES/APCI$^+$): 442 (M+H), 444 (M+2+H).

(Example 8) 5-Chloro-N-[4-(2,4-dimethoxybenzyl)-5-oxo-2,3,4,5-tetrahydropyrido[3,2-f][1,4]oxazepin-7-yl]-2-methoxybenzenesulfonamide

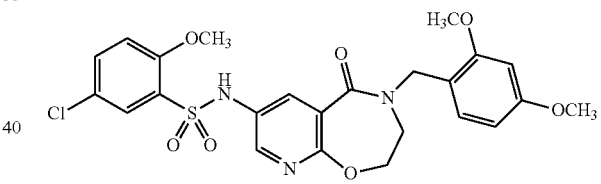

(8a) 2-[(2,4-Dimethoxybenzyl)amino]ethanol

To a mixture of 2,4-dimethoxybenzaldehyde (16.20 g, 97.5 mmol) and 2-aminoethanol (5.98 g, 97.9 mmol) in methanol (120 mL), anhydrous sodium sulfate (6.23 g, 43.9 mmol) was added, and the mixture was stirred at room temperature for 20 hours. Subsequently, to the mixture, sodium borohydride (1.84 g, 48.6 mmol) was added over 15 minutes, and the mixture was stirred at 22° C. for 30 minutes. To the reaction mixture, acetic acid (2.8 mL, 49 mmol) was added, and the mixture was stirred for 10 minutes and concentrated into approximately ½ of the amount under reduced pressure. The concentrated mixture was diluted by addition of water and a saturated aqueous solution of sodium bicarbonate, followed by extraction with methylene chloride. The organic layer was washed with a saturated aqueous solution of sodium chloride and dried over anhydrous sodium sulfate. After filtration, the solvent was distilled off under reduced pressure. To the residue, n-hexane (100 mL) and ethyl acetate (4 mL) were added, and the precipitated solid was collected by filtration, washed with n-hexane, and then dried to obtain the title compound (18.44 g, yield: 90%).

¹H NMR spectrum (CDCl₃, 400 MHz) δ: 7.12 (1H, d, J=8.2 Hz), 6.47-6.42 (2H, m), 3.82 (3H, s), 3.80 (3H, s), 3.74 (2H, S), 3.65-3.63 (2H, m), 2.76-2.74 (2H, m).

(8b) 2-Chloro-N-(2,4-dimethoxybenzyl)-N-(2-hydroxyethyl)-5-nitropyridine-3-carboxamide To a suspension of 2-chloro-5-nitropyridine-3-carboxylic acid (4.91 g, 24.2 mmol) and oxalyl chloride (2.6 mL, 30 mmol) in methylene chloride (120 mL), N,N-dimethylformamide (0.10 mL, 1.3 mmol) was added at room temperature, and the mixture was stirred at the same temperature as above for 30 minutes. The reaction mixture was concentrated under reduced pressure to prepare a crude product of 2-chloro-5-nitropyridine-3-carboxylic acid chloride. To a solution of 2-[(2,4-dimethoxybenzyl)amino]ethanol (5.11 g, 24.2 mmol) obtained in Example (8a) and N,N-diisopropylethylamine (8.25 mL, 48.5 mmol) in tetrahydrofuran (50 mL), a solution of the crude product of 2-chloro-5-nitropyridine-3-carboxylic acid chloride in tetrahydrofuran (70 mL) was added over 20 minutes under ice cooling, and the reaction mixture was stirred at the same temperature as above for 90 minutes. To the reaction mixture, water (0.05 mL) was added, and then, the mixture was concentrated under reduced pressure. The concentrated mixture was diluted by addition of water, followed by extraction with ethyl acetate. The organic layer was washed with water and a saturated aqueous solution of sodium chloride, and anhydrous magnesium sulfate and charcoal were added thereto. After filtration through pad of Celite 545 (R), the solvent was distilled off under reduced pressure. To the residue, diisopropyl ether (50 mL) and ethyl acetate (10 mL) were added to precipitate a solid. The suspension was stirred at room temperature for 30 minutes. The precipitated solid was collected by filtration, washed with a mixed solvent of diisopropyl ether/ethyl acetate=5/1, and then dried to obtain the title compound (8.30 g, yield: 87%).

¹H NMR spectrum (CDCl₃, 400 MHz) δ: 9.24 (0.8H, d, J=2.7 Hz), 9.21 (0.2H, d, J=2.7 Hz), 8.57 (0.2H, d, J=2.7 Hz), 8.44 (0.8H, d, J=2.7 Hz), 7.38 (0.2H, d, J=8.2 Hz), 6.99 (0.8H, d, J=8.2 Hz), 6.54-6.48 (0.4H, m), 6.45-6.40 (1.6H, m), 5.13 (0.2H, d, J=14.9 Hz), 4.53 (0.2H, d, J=14.9 Hz), 4.38-3.54 (10.8H, m), 3.24-3.19 (0.4H, t, J=5.1 Hz), 2.42 (0.4H, t, J=5.1 Hz).

(8c) 4-(2,4-Dimethoxybenzyl)-7-nitro-3,4-dihydropyrido[3,2-f][1,4]oxazepin-5(2H)-one A solution of sodium bis(trimethylsilyl)amide in tetrahydrofuran (ca. 1.9 mol/L, 14.4 mL, 27.4 mmol) was diluted with tetrahydrofuran (450 mL). A solution of 2-chloro-N-(2,4-dimethoxybenzyl)-N-(2-hydroxyethyl)-5-nitropyridine-3-carboxamide (7.22 g, 18.2 mmol) obtained in Example (8b) in tetrahydrofuran (450 mL) was added thereto over 70 minutes under ice cooling, and the mixture was stirred at the same temperature as above for 10 minutes and further stirred at room temperature for 30 minutes. To the reaction mixture, a saturated aqueous solution of ammonium chloride (100 mL) was added, and then, the reaction mixture was concentrated into approximately ⅕ of the amount under reduced pressure. The concentrated mixture was diluted by addition of water, followed by extraction with ethyl acetate twice. The organic layer was washed with water and a saturated aqueous solution of sodium chloride and dried over anhydrous magnesium sulfate. After filtration, the solvent was distilled off under reduced pressure, and the residue was purified by silica gel column chromatography (ethyl acetate/n-hexane/methylene chloride=1/1/1-3/2/2). To the obtained solid, diisopropyl ether (20 mL) and ethyl acetate (10 mL) were added, and the suspension was stirred at room temperature for overnight. The precipitated solid was collected by filtration, washed with a mixed solvent of diisopropyl ether/ethyl acetate=2/1, and then dried to obtain the title compound (4.18 g, yield: 64%).

¹H NMR spectrum (CDCl₃, 400 MHz) δ: 9.34 (1H, d, J=2.7 Hz), 9.20 (1H, d, J=2.7 Hz), 7.34-7.32 (1H, m), 6.50-6.48 (2H, m), 4.76 (2H, s), 4.53-4.51 (2H, m), 3.84 (3H, s), 3.81 (3H, s), 3.78-3.76 (2H, m).

(8d) 7-Amino-4-(2,4-dimethoxybenzyl)-3,4-dihydropyrido[3,2-f][1,4]oxazepin-5(2H)-one A mixture of 4-(2,4-dimethoxybenzyl)-7-nitro-3,4-dihydropyrido[3,2-f][1,4]oxazepin-5(2H)-one (4.18 g, 11.6 mmol) obtained in Example (8c) and 10% palladium carbon (water content: 54.6%, 1.36 g) in tetrahydrofuran (110 mL) and ethanol (55 mL) was stirred at room temperature for 3 hours at normal pressure under the hydrogen atmosphere. Hydrogen in the reaction container was replaced with nitrogen, and then, the reaction mixture was filtered through pad of Celite 545(R). The solvent in the filtrate was distilled off under reduced pressure to obtain the title compound (3.93 g, yield: quantitative).

¹H NMR spectrum (CDCl₃, 400 MHz) δ: 7.86 (1H, d, J=3.1 Hz), 7.62 (1H, d, J=3.1 Hz), 7.31-7.28 (1H, m), 6.49-6.47 (2H, m), 4.75 (2H, s), 4.25 (2H, t, J=4.9 Hz), 3.82 (3H, s), 3.81 (3H, s), 3.64 (2H, br s), 3.55 (2H, t, J=4.9 Hz).

(8e) 5-Chloro-N-[4-(2,4-dimethoxybenzyl)-5-oxo-2,3,4,5-tetrahydropyrido[3,2-f][1,4]oxazepin-7-yl]-2-methoxybenzenesulfonamide To a mixture of 7-amino-4-(2,4-dimethoxybenzyl)-3,4-dihydropyrido[3,2-f][1,4]oxazepin-5(2H)-one (229 mg, 0.70 mmol) obtained in Example (8d) and pyridine (3.0 mL, 37.3 mmol), 5-chloro-2-methoxybenzenesulfonyl chloride (190 mg, 0.79 mmol) was added at room temperature, and the mixture was stirred at 80° C. for 2.5 hours in an oil bath. The reaction mixture was cooled and then concentrated under reduced pressure, and the residue was purified in an automatic chromatography apparatus (ethyl acetate/methanol=100/0-85/15) to obtain the title compound (349 mg, yield: 94%).

¹H NMR spectrum (CDCl₃, 400 MHz) δ: 8.24 (1H, d, J=3.0 Hz), 8.07 (1H, d, J=3.0 Hz), 7.74 (1H, d, J=2.4 Hz), 7.48 (1H, dd, J=8.8, 2.7 Hz), 7.30-7.22 (2H, m), 7.01 (1H, d, J=9.1 Hz), 6.49-6.46 (2H, m), 4.70 (2H, s), 4.32 (2H, t, J=4.6 Hz), 4.09 (3H, s), 3.81-3.80 (6H, m), 3.60 (2H, t, J=4.6 Hz).

MS spectrum (ES/APCI⁺): 534 (M+H), 536 (M+2+H).

(Example 9) 5-Chloro-2-methoxy-N-(5-oxo-2,3,4,5-tetrahydropyrido[3,2-f][1,4]oxazepin-7-yl)benzenesulfonamide

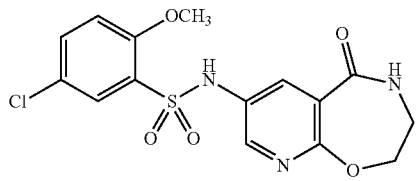

To a suspension of 5-chloro-N-[4-(2,4-dimethoxybenzyl)-5-oxo-2,3,4,5-tetrahydropyrido[3,2-f][1,4]oxazepin-7-yl]-2-methoxybenzenesulfonamide (335 mg, 0.63 mmol) obtained in Example (8e) in chloroform (5 mL), anisole (0.136 mL, 1.25 mmol), trifluoroacetic acid (2 mL, 26 mmol) and trifluoromethanesulfonic acid (0.165 mL, 1.88 mmol) were added at room temperature, and the mixture was stirred at room temperature for 1 hour. The reaction mixture was concentrated under reduced pressure, and the concentrated mixture was diluted by addition of chloroform and a saturated aqueous solution of sodium bicarbonate and stirred at room temperature for 10 minutes. The organic layer was separated, and the aqueous layer was subjected to extraction with a mixed solvent of ethyl acetate/tetrahydrofuran=2/1 three times. All the organic layers were combined and dried over anhydrous sodium sulfate. After filtration, the solvent was distilled off under reduced pressure. To the residue, ethyl acetate was added, and the precipitated solid was collected by filtration to obtain the title compound (154 mg, yield: 64%).

$^1$H NMR spectrum (DMSO-d6, 400 MHz) δ: 10.29 (1H, s), 8.53 (1H, br t, J=5.2 Hz), 8.11-8.08 (2H, m), 7.69-7.64 (2H, m), 7.26 (1H, d, J=8.5 Hz), 4.37-4.35 (2H, m), 3.88 (3H, s), 3.38-3.34 (2H, m).

MS spectrum (ES/APCI$^+$): 384 (M+H), 386 (M+2+H).

(Example 10) 5-Fluoro-2-methoxy-N-(5-oxo-2,3,4,5-tetrahydropyrido[3,2-f][1,4]oxazepin-7-yl)benzenesulfonamide

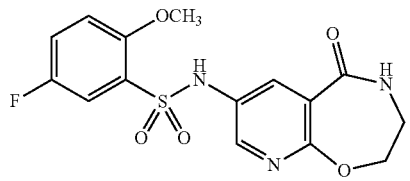 [SMILES: COc1ccc(F)cc1S(=O)(=O)Nc1cnc2c(c1)C(=O)NCCO2]

(10a) N-[4-(2,4-Dimethoxybenzyl)-5-oxo-2,3,4,5-tetrahydropyrido[3,2-f][1,4]oxazepin-7-yl]-5-fluoro-2-methoxybenzenesulfonamide To a mixture of 7-amino-4-(2,4-dimethoxybenzyl)-3,4-dihydropyrido[3,2-f][1,4]oxazepin-5(2H)-one (200 mg, 0.61 mmol) obtained in Example (8d) and pyridine (6 mL, 74.6 mmol), 5-fluoro-2-methoxybenzenesulfonyl chloride (158 mg, 0.70 mmol) was added at room temperature, and the mixture was stirred at 80° C. for 2 hours in an oil bath. The reaction mixture was cooled and then concentrated under reduced pressure, and the residue was purified in an automatic chromatography apparatus (ethyl acetate/methanol=100/0-90/10) to obtain the title compound (305 mg, yield: 97%).

$^1$H NMR spectrum (CDCl$_3$, 400 MHz) δ: 8.24 (1H, d, J=2.4 Hz), 8.08 (1H, d, J=2.4 Hz), 7.52-7.49 (1H, m), 7.26-7.20 (2H, m), 7.04-7.00 (1H, m), 6.95 (1H, br s), 6.48-6.46 (2H, m), 4.70 (2H, s), 4.31 (2H, br t, J=4.3 Hz), 4.08 (3H, s), 3.81-3.80 (6H, m), 3.59 (2H, br t, J=4.3 Hz).

(10b) 5-Fluoro-2-methoxy-N-(5-oxo-2,3,4,5-tetrahydropyrido[3,2-f][1,4]oxazepin-7-yl)benzenesulfonamide To a suspension of N-[4-(2,4-dimethoxybenzyl)-5-oxo-2,3,4,5-tetrahydropyrido[3,2-f][1,4]oxazepin-7-yl]-5-fluoro-2-methoxybenzenesulfonamide (305 mg, 0.59 mmol) obtained in Example (10a) in chloroform (5 mL), anisole (0.128 mL, 1.17 mmol), trifluoroacetic acid (2 mL, 26 mmol) and trifluoromethanesulfonic acid (0.155 mL, 1.77 mmol) were added at room temperature, and the mixture was stirred at room temperature for 1 hour. The reaction mixture was concentrated under reduced pressure, and the concentrated mixture was diluted by addition of ethyl acetate and a saturated aqueous solution of sodium bicarbonate and stirred at room temperature for 1.5 hours. The precipitated solid was collected by filtration to obtain the title compound (192 mg, yield: 89%).

$^1$H NMR spectrum (DMSO-d6, 400 MHz) δ: 10.28 (1H, s), 8.52 (1H, br t, J=4.9 Hz), 8.11-8.08 (2H, m), 7.51-7.46 (2H, m), 7.26-7.23 (1H, m), 4.36 (2H, t, J=4.3 Hz), 3.86 (3H, s), 3.40-3.35 (2H, m).

MS spectrum (ES/APCI$^+$): 368 (M+H).

(Example 11) 2,5-Dimethoxy-N-(5-oxo-2,3,4,5-tetrahydropyrido[3,2-f][1,4]oxazepin-7-yl)benzenesulfonamide

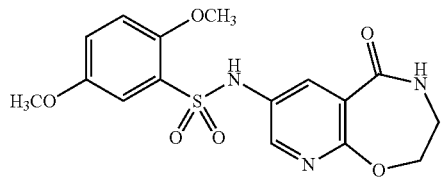 [SMILES: COc1ccc(OC)c(S(=O)(=O)Nc2cnc3c(c2)C(=O)NCCO3)c1]

(11a) N-[4-(2,4-Dimethoxybenzyl)-5-oxo-2,3,4,5-tetrahydropyrido[3,2-f][1,4]oxazepin-7-yl]-2,5-dimethoxybenzenesulfonamide To a mixture of 7-amino-4-(2,4-dimethoxybenzyl)-3,4-dihydropyrido[3,2-f][1,4]oxazepin-5(2H)-one (200 mg, 0.61 mmol) obtained in Example (8d) and pyridine (5 mL, 62 mmol), 2,5-dimethoxybenzenesulfonyl chloride (158 mg, 0.67 mmol) was added, and the mixture was stirred at 80° C. for 3 hours in an oil bath. The reaction mixture was cooled and then concentrated under reduced pressure, and the residue was purified in an automatic chromatography apparatus (ethyl acetate/methanol=100/0-85/15) to obtain the title compound (290 mg, yield: 90%).

$^1$H NMR spectrum (CDCl$_3$, 400 MHz) δ: 8.24 (1H, d, J=3.0 Hz), 8.09-8.08 (1H, m), 7.30-7.25 (2H, m), 7.07-6.98 (3H, m), 6.48-6.45 (2H, m), 4.70 (2H, s), 4.30 (2H, t, J=4.6 Hz), 4.04 (3H, s), 3.81-3.79 (6H, m), 3.75 (3H, s), 3.58 (2H, t, J=4.6 Hz).

(11b) 2,5-Dimethoxy-N-(5-oxo-2,3,4,5-tetrahydropyrido[3,2-f][1,4]oxazepin-7-yl)benzenesulfonamide To a solution of N-[4-(2,4-dimethoxybenzyl)-5-oxo-2,3,4,5-tetrahydropyrido[3,2-f][1,4]oxazepin-7-yl]-2,5-dimethoxybenzenesulfonamide (290 mg, 0.55 mmol) obtained in Example (11a) in chloroform (4 mL), anisole (0.12 mL, 1.1 mmol), trifluoroacetic acid (2 mL, 26 mmol) and trifluoromethanesulfonic acid (0.15 mL, 1.7 mmol) were added, and the mixture was stirred at room temperature for 1 hour. The reaction mixture was neutralized by the addition of a saturated aqueous solution of sodium bicarbonate, followed by extraction with chloroform. The organic layer was dried over anhydrous sodium sulfate. After filtration, the solvent was distilled off under reduced pressure. To the residue, diisopropyl ether was added, and the precipitated solid was collected by filtration, washed with diisopropyl ether, and then dried to obtain the title compound (144 mg, yield: 77%).

$^1$H NMR spectrum (DMSO-d6, 400 MHz) δ: 10.16 (1H, s), 8.51 (1H, t, J=5.2 Hz), 8.09 (2H, dd, J=10.3, 3.0 Hz), 7.21-7.12 (3H, m), 4.35 (2H, t, J=4.3 Hz), 3.81 (3H, s), 3.72 (3H, s), 3.39-3.34 (2H, m).

MS spectrum (ES/APCI$^+$): 380 (M+H).

(Example 12) 2-Methoxy-N-(5-oxo-2,3,4,5-tetrahydropyrido[3,2-f][1,4]oxazepin-7-yl)benzenesulfonamide

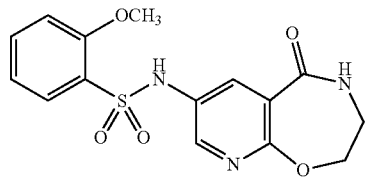 [SMILES: COc1ccccc1S(=O)(=O)Nc1cnc2c(c1)C(=O)NCCO2]

(12a) N-[4-(2,4-Dimethoxybenzyl)-5-oxo-2,3,4,5-tetrahydropyrido[3,2-f][1,4]oxazepin-7-yl]-2-methoxybenzenesulfonamide To a mixture of 7-amino-4-(2,4-dimethoxybenzyl)-3,4-dihydropyrido[3,2-f][1,4]oxazepin-5(2H)-one (150 mg, 0.46 mmol) obtained in Example (8d) and pyridine (4 mL, 50 mmol), 2-methoxybenzenesulfonyl chloride (104 mg, 0.50 mmol) was added, and the mixture was stirred at 80° C. for 2.5 hours in an oil bath. The reaction mixture was cooled and then concentrated under reduced pressure, and the residue was purified in an automatic chromatography apparatus (ethyl acetate/methanol=100/0-85/15) to obtain the title compound (212 mg, yield: 93%).

$^1$H NMR spectrum (CDCl$_3$, 400 MHz) δ: 8.23 (1H, d, J=2.4 Hz), 8.07-8.06 (1H, m), 7.79-7.77 (1H, m), 7.55-7.51 (1H, m), 7.30-7.24 (1H, m), 7.08-6.98 (2H, m), 6.92 (1H, s), 6.48-6.43 (2H, m), 4.69 (2H, s), 4.29 (2H, t, J=4.3 Hz), 4.09 (3H, s), 3.81-3.78 (6H, m), 3.56 (2H, t, J=4.6 Hz).

(12b) 2-Methoxy-N-(5-oxo-2,3,4,5-tetrahydropyrido[3,2-f][1,4]oxazepin-7-yl)benzenesulfonamide To a suspension of N-[4-(2,4-dimethoxybenzyl)-5-oxo-2,3,4,5-tetrahydropyrido[3,2-f][1,4]oxazepin-7-yl]-2-methoxybenzenesulfonamide (212 mg, 0.43 mmol) obtained in Example (12a) in chloroform (4 mL), anisole (0.1 mL, 0.9 mmol), trifluoroacetic acid (2 mL, 26 mmol) and trifluoromethanesulfonic acid (0.11 mL, 1.3 mmol) were added, and the mixture was stirred at room temperature for 3 hours. The reaction mixture was neutralized by the addition of a saturated aqueous solution of sodium bicarbonate, followed by extraction with chloroform twice. The organic layer was dried over anhydrous sodium sulfate. After filtration, the solvent was distilled off under reduced pressure. To the residue, diisopropyl ether was added, and the precipitated solid was collected by filtration, washed with diisopropyl ether, and then dried to obtain the title compound (55.2 mg, yield: 37%).

$^1$H NMR spectrum (DMSO-d6, 400 MHz) δ: 10.12 (1H, s), 8.52-8.48 (1H, m), 8.10-8.06 (2H, m), 7.70 (1H, dd, J=7.9, 1.8 Hz), 7.61-7.56 (1H, m), 7.20 (1H, d, J=8.5 Hz), 7.03 (1H, t, J=7.6 Hz), 4.34 (2H, t, J=4.3 Hz), 3.88 (3H, s), 3.37-3.31 (2H, m).

MS spectrum (ES/APCI$^+$): 350 (M+H).

(Example 13) 5-Chloro-N-(5-oxo-2,3,4,5-tetrahydropyrido[3,2-f][1,4]oxazepin-7-yl)-2-(trifluoromethoxy)benzenesulfonamide

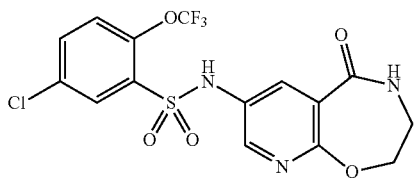 [SMILES: O=C1NCCOc2ncc(NS(=O)(=O)c3cc(Cl)ccc3OC(F)(F)F)cc21]

(13a) 5-Chloro-2-(trifluoromethoxy)benzenesulfonyl chloride

To chlorosulfonic acid (30.0 mL, 451 mmol), 4-chlorophenyl trifluoromethyl ether (2.60 mL, 18.1 mmol) was added, and the mixture was stirred at room temperature for 46 hours. The reaction mixture was carefully poured into ice (approximately 300 mL), followed by extraction with methylene chloride twice. The organic layer was washed with water and a saturated aqueous solution of sodium chloride and dried over anhydrous magnesium sulfate. After filtration, the solvent was distilled off under reduced pressure, and the residue was purified by silica gel column chromatography (n-hexane/methylene chloride=1/1) to obtain the title compound (approximately 83% content, 4.67 g, yield: 73%) as a mixture containing positional isomers.

$^1$H NMR spectrum (CDCl$_3$, 400 MHz) δ: 8.09 (0.83H, d, J=2.7 Hz), 8.02 (0.17H, br d, J=2.7 Hz), 7.75 (0.83H, dd, J=8.8, 2.7 Hz), 7.71 (0.17H, d, J=8.6 Hz), 7.55-7.52 (0.17H, m), 7.50-7.47 (0.83H, m).

(13b) 5-Chloro-N-[4-(2,4-dimethoxybenzyl)-5-oxo-2,3,4,5-tetrahydropyrido[3,2-f][1,4]oxazepin-7-yl]-2-(trifluoromethoxy)benzenesulfonamide To a mixture of 7-amino-4-(2,4-dimethoxybenzyl)-3,4-dihydropyrido[3,2-f][1,4]oxazepin-5(2H)-one (260 mg, 0.79 mmol) obtained in Example (8d) and pyridine (8 mL, 99 mmol), 5-chloro-2-(trifluoromethoxy)benzenesulfonyl chloride (approximately 83% content, 325 mg, 0.92 mmol) obtained in Example (13a) was added at room temperature, and the mixture was stirred at 80° C. for 2.5 hours in an oil bath. The reaction mixture was cooled and then concentrated under reduced pressure, and the residue was purified in an automatic chromatography apparatus (n-hexane/ethyl acetate=100/0-0/100) to obtain the title compound (305 mg, yield: 66%).

$^1$H NMR spectrum (CDCl$_3$, 400 MHz) δ: 8.29 (1H, d, J=3.0 Hz), 8.17 (1H, d, J=3.0 Hz), 7.90 (1H, d, J=3.0 Hz), 7.58-7.54 (1H, m), 7.38-7.27 (3H, m), 6.49-6.44 (2H, m), 4.73 (2H, s), 4.33 (2H, t, J=4.6 Hz), 3.81 (6H, s), 3.63-3.60 (2H, m).

(13c) 5-Chloro-N-(5-oxo-2,3,4,5-tetrahydropyrido[3,2-f][1,4]oxazepin-7-yl)-2-(trifluoromethoxy)benzenesulfonamide To a solution of 5-chloro-N-[4-(2,4-dimethoxybenzyl)-5-oxo-2,3,4,5-tetrahydropyrido[3,2-f][1,4]oxazepin-7-yl]-2-

(trifluoromethoxy)benzenesulfonamide (305 mg, 0.52 mmol) obtained in Example (13b) and anisole (0.113 mL, 1.04 mmol) in chloroform (8 mL), trifluoroacetic acid (3 mL, 39 mmol) and trifluoromethanesulfonic acid (0.137 mL, 1.56 mmol) were added at room temperature, and the mixture was stirred at room temperature for 2.5 hours. To the reaction mixture, water was added, and the mixture was stirred at room temperature for 1 hour, followed by extraction with ethyl acetate. The organic layer was washed with a saturated aqueous solution of sodium bicarbonate and dried over anhydrous sodium sulfate. After filtration, the solvent was distilled off under reduced pressure. To the residue, diisopropyl ether was added, and the precipitated solid was collected by filtration, washed with diisopropyl ether, and then dried to obtain the title compound (171 mg, yield: 75%).

$^1$H NMR spectrum (DMSO-d6, 400 MHz) δ: 10.78 (1H, s), 8.58-8.53 (1H, m), 8.13-8.06 (2H, m), 7.91-7.85 (2H, m), 7.65-7.60 (1H, m), 4.39 (2H, t, J=4.3 Hz), 3.41-3.36 (2H, m).

MS spectrum (ES/APCI$^+$): 438 (M+H), 440 (M+2+H).

(Example 14) 5-Chloro-N-(2,4-dimethyl-5-oxo-2,3,4,5-tetrahydropyrido[3,2-f][1,4]oxazepin-7-yl)-2-methoxybenzenesulfonamide

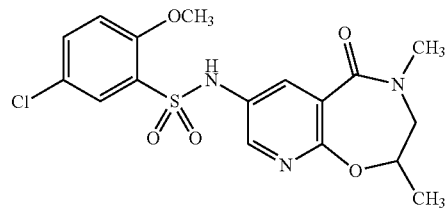 [SMILES: COc1ccc(Cl)cc1S(=O)(=O)Nc1cnc2c(c1)C(=O)N(C)CC(C)O2]

(14a) 2,4-Dimethyl-7-nitro-3,4-dihydropyrido[3,2-f][1,4]oxazepin-5(2H)-one

The title compound (280 mg, yield for 2 steps: 44%) was obtained by production according to Examples (1a) and (1b) using 2-chloro-5-nitropyridine-3-carboxylic acid (550 mg, 2.71 mmol) and 1-(methylamino)propan-2-ol (240 mg, 2.69 mmol) as starting materials.

$^1$H NMR spectrum (CDCl$_3$, 400 MHz) δ: 9.23 (2H, s), 4.92-4.85 (1H, m), 3.69-3.56 (2H, m), 3.27 (3H, s), 1.24 (3H, d, J=12.8 Hz).

(14b) 7-Amino-2,4-dimethyl-3,4-dihydropyrido[3,2-f][1,4]oxazepin-5(2H)-one

The title compound (200 mg, yield: 82%) was obtained by production according to the method described in Example (1c) using 2,4-dimethyl-7-nitro-3,4-dihydropyrido[3,2-f][1,4]oxazepin-5(2H)-one (280 mg, 1.18 mmol) obtained in Example (14a).

$^1$H NMR spectrum (CDCl$_3$, 400 MHz) δ: 7.87 (1H, d, J=3.0 Hz), 7.50 (1H, d, J=3.0 Hz), 4.77-4.70 (1H, m), 4.00-3.91 (1H, m), 3.65 (2H, br s), 3.49-3.44 (1H, m), 3.35-3.27 (1H, m), 3.23 (3H, s), 1.43 (5H, d, J=6.7 Hz).

(14c) 5-Chloro-N-(2,4-dimethyl-5-oxo-2,3,4,5-tetrahydropyrido[3,2-f][1,4]oxazepin-7-yl)-2-methoxy-benzenesulfonamide The title compound (90 mg, yield: 46%) was obtained by production according to Example (1d) using 7-amino-2,4-dimethyl-3,4-dihydropyrido[3,2-f][1,4]oxazepin-5(2H)-one (99 mg, 0.48 mmol) obtained in Example (14b) and 5-chloro-2-methoxybenzenesulfonyl chloride (132.5 mg, 0.55 mmol).

$^1$H NMR spectrum (DMSO-d6, 400 MHz) δ: 10.39 (1H, s), 8.08 (1H, d, J=3.0 Hz), 7.82 (1H, d, J=3.0 Hz), 7.69-7.66 (2H, m), 7.28-7.23 (1H, m), 4.73-4.67 (1H, m), 3.86 (3H, s), 3.55-3.49 (1H, m), 3.40-3.29 (2H, m), 3.07 (3H, s), 1.26 (4H, d, J=6.1 Hz).

MS spectrum (ES/APCI$^+$): 412 (M+H), 414 (M+2+H).

(Example 15) N-(2,4-Dimethyl-5-oxo-2,3,4,5-tetrahydropyrido[3,2-f][1,4]oxazepin-7-yl)-5-fluoro-2-methoxybenzenesulfonamide

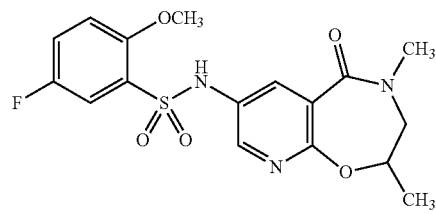 [SMILES: COc1ccc(F)cc1S(=O)(=O)Nc1cnc2c(c1)C(=O)N(C)CC(C)O2]

The title compound (104 mg, yield: 55%) was obtained by production according to Example (1d) using 7-amino-2,4-dimethyl-3,4-dihydropyrido[3,2-f][1,4]oxazepin-5(2H)-one (99 mg, 0.48 mmol) obtained in Example (14b) and 5-fluoro-2-methoxybenzenesulfonyl chloride (114 mg, 0.51 mmol).

$^1$H NMR spectrum (DMSO-d6, 400 MHz) δ: 10.38 (1H, s), 8.08 (1H, d, J=2.4 Hz), 7.82-7.81 (1H, m), 7.53-7.47 (2H, m), 7.24 (1H, dd, J=8.5, 4.3 Hz), 4.72-4.67 (1H, m), 3.85 (3H, s), 3.54-3.48 (1H, m), 3.39-3.30 (1H, m), 3.07 (3H, s), 1.25 (3H, d, J=6.1 Hz).

MS spectrum (ES/APCI$^+$): 396 (M+H).

(Example 16) 5-Chloro-N-(3,4-dimethyl-5-oxo-2,3,4,5-tetrahydropyrido[3,2-f][1,4]oxazepin-7-yl)-2-methoxybenzenesulfonamide

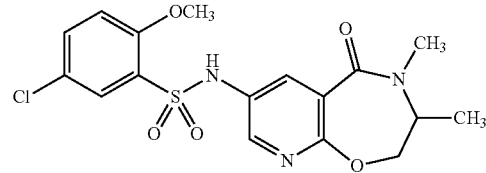 [SMILES: COc1ccc(Cl)cc1S(=O)(=O)Nc1cnc2c(c1)C(=O)N(C)C(C)CO2]

(16a) 3,4-Dimethyl-7-nitro-3,4-dihydropyrido[3,2-f][1,4]oxazepin-5(2H)-one

The title compound (234 mg, yield for 2 steps: 37%) was obtained by production according to the method described in Examples (1a) and (1b) using 2-chloro-5-nitropyridine-3-carboxylic acid (550 mg, 2.71 mmol) and 2-(methylamino)propan-1-ol (240 mg, 2.69 mmol).

$^1$H NMR spectrum (CDCl$_3$, 400 MHz) δ: 9.59 (1H, d, J=3.0 Hz), 9.23-9.20 (1H, m), 4.70 (1H, dd, J=13.1, 5.2 Hz), 4.47 (1H, d, J=12.8 Hz), 3.84-3.76 (1H, m), 3.25 (3H, s), 1.36 (4H, d, J=7.3 Hz).

(16b) 7-Amino-3,4-dimethyl-3,4-dihydropyrido[3,2-f][1,4]oxazepin-5(2H)-one

The title compound (168 mg, yield: 82%) was obtained by production according to the method described in Example (1c) using 3,4-dimethyl-7-nitro-3,4-dihydropyrido[3,2-f][1,4]oxazepin-5(2H)-one (234 mg, 0.99 mmol) obtained in Example (16a).

$^1$H NMR spectrum (CDCl$_3$, 400 MHz) δ: 8.00 (1H, d, J=3.0 Hz), 7.88 (1H, d, J=3.0 Hz), 4.44 (1H, dd, J=12.5, 6.4 Hz), 4.28-4.23 (1H, m), 3.81-3.71 (1H, m), 3.60 (2H, br s), 3.18 (3H, s), 1.32 (3H, d, J=6.7 Hz).

(16c) 5-Chloro-N-(3,4-dimethyl-5-oxo-2,3,4,5-tetrahydropyrido[3,2-f][1,4]oxazepin-7-yl)-2-methoxybenzenesulfonamide The title compound (73 mg, yield: 44%) was obtained by production according to Example (1d) using 7-amino-3,4-dimethyl-3,4-dihydropyrido[3,2-f][1,4]oxazepin-5(2H)-one (84 mg, 0.41 mmol) obtained in Example (16b) and 5-chloro-2-methoxybenzenesulfonyl chloride (111 mg, 0.46 mmol).

$^1$H NMR spectrum (CDCl$_3$, 400 MHz) δ: 8.36-8.32 (2H, m), 7.74 (1H, d, J=3.1 Hz), 7.46 (1H, dd, J=8.9, 2.7 Hz), 7.06 (1H, br s), 7.00 (1H, d, J=8.5 Hz), 4.51 (1H, dd, J=12.8, 5.5 Hz), 4.26 (1H, d, J=12.8 Hz), 4.08 (3H, s), 3.73-3.67 (1H, m), 3.17 (3H, s), 1.30 (3H, d, J=6.7 Hz).

MS spectrum (ES/APCI$^+$): 412 (M+H), 414 (M+2+H).

(Example 17) N-(3,4-Dimethyl-5-oxo-2,3,4,5-tetrahydropyrido[3,2-f][1,4]oxazepin-7-yl)-5-fluoro-2-methoxybenzenesulfonamide

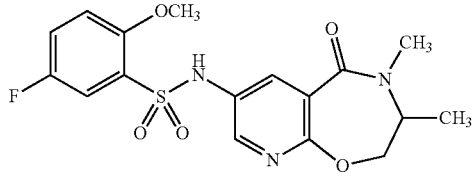 [SMILES: COc1ccc(F)cc1S(=O)(=O)Nc1cnc2c(c1)C(=O)N(C)C(C)CO2]

The title compound (78 mg, yield: 50%) was obtained by production according to Example (1d) using 7-amino-3,4-dimethyl-3,4-dihydropyrido[3,2-f][1,4]oxazepin-5(2H)-one (83 mg, 0.40 mmol) obtained in Example (16b) and 5-fluoro-2-methoxybenzenesulfonyl chloride (104 mg, 0.46 mmol).

$^1$H NMR spectrum (CDCl$_3$, 400 MHz) δ: 8.36-8.31 (2H, m), 7.49 (1H, dd, J=7.6, 3.4 Hz), 7.24-7.20 (1H, m), 7.08 (1H, br s), 7.02 (1H, dd, J=9.2, 4.3 Hz), 4.51 (1H, dd, J=12.5, 5.2 Hz), 4.25 (1H, d, J=12.8 Hz), 4.08 (3H, s), 3.73-3.66 (1H, m), 3.16 (3H, s), 1.29 (3H, d, J=7.3 Hz).

MS spectrum (ES/APCI$^+$): 396 (M+H).

(Example 18) 5-Chloro-N-[(3S)-3,4-dimethyl-5-oxo-2,3,4,5-tetrahydropyrido[3,2-f][1,4]oxazepin-7-yl]-2-methoxybenzenesulfonamide

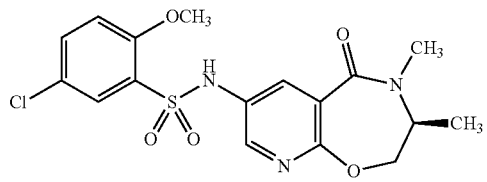 [SMILES: COc1ccc(Cl)cc1S(=O)(=O)Nc1cnc2c(c1)C(=O)N(C)[C@@H](C)CO2]

(18a) (2S)-2-[(2,4-Dimethoxybenzyl)amino]propan-1-ol

The title compound (2.98 g, yield: 99%) was obtained by production according to the method described in Example (8a) using 2,4-dimethoxybenzaldehyde (2.22 g, 13.4 mmol) and (2S)-2-aminopropan-1-ol (1 g, 13.3 mmol).

$^1$H NMR spectrum (CDCl$_3$, 400 MHz) δ: 7.13 (1H, d, J=7.9 Hz), 6.50-6.42 (2H, m), 3.85-3.79 (7H, m), 3.77-3.60 (3H, m), 3.26 (1H, dd, J=10.6, 6.4 Hz), 2.84-2.76 (1H, m), 1.06 (3H, d, J=6.7 Hz).

(18b) (3S)-4-(2,4-Dimethoxybenzyl)-3-methyl-7-nitro-3,4-dihydropyrido[3,2-f][1,4]oxazepin-5(2H)-one The title compound (781.8 mg, yield for 2 steps: 60%) was obtained by production according to the method described in Examples (1a) and (1b) using 2-chloro-5-nitropyridine-3-carboxylic acid (700 mg, 3.46 mmol) and (2S)-2-[(2,4-dimethoxybenzyl)amino]propan-1-ol (785 mg, 3.49 mmol) obtained in Example (18a).

$^1$H NMR spectrum (CDCl$_3$, 400 MHz) δ: 9.62-9.61 (1H, m), 9.20 (1H, d, J=3.0 Hz), 7.33 (1H, d, J=8.5 Hz), 6.50-6.47 (2H, m), 4.95 (1H, d, J=14.6 Hz), 4.65-4.55 (2H, m), 4.31 (1H, d, J=12.8 Hz), 4.04-3.97 (1H, m), 3.84 (3H, s), 3.81 (3H, s), 1.23 (3H, d, J=6.7 Hz).

(18c) (3S)-3-Methyl-7-nitro-3,4-dihydropyrido[3,2-f][1,4]oxazepin-5(2H)-one

To a solution of (3S)-4-(2,4-dimethoxybenzyl)-3-methyl-7-nitro-3,4-dihydropyrido[3,2-f][1,4]oxazepin-5(2H)-one (450 mg, 1.21 mmol) obtained in Example (18b) and anisole (0.2 mL, 1.8 mmol) in chloroform (5 mL), trifluoroacetic acid (3 mL, 39 mmol) and trifluoromethanesulfonic acid (0.2 mL, 2.3 mmol) were added, and the mixture was stirred at room temperature for 1 hour. The reaction mixture was concentrated under reduced pressure, and the concentrated mixture was diluted by addition of chloroform, washed with a saturated aqueous solution of sodium bicarbonate and a saturated aqueous solution of sodium chloride, and dried over anhydrous sodium sulfate. After filtration, the solvent was distilled off under reduced pressure. To the residue, diisopropyl ether was added, and the precipitated solid was collected by filtration, washed with diisopropyl ether, and then dried to obtain the title compound (228 mg, yield: 85%).

$^1$H NMR spectrum (CDCl$_3$, 400 MHz) δ: 9.49-9.47 (1H, m), 9.26-9.24 (1H, m), 6.49 (1H, br s), 4.60 (1H, d, J=12.1 Hz), 4.47-4.40 (1H, m), 4.02-3.94 (1H, m), 1.42-1.39 (3H, m).

(18d) (3S)-3,4-Dimethyl-7-nitro-3,4-dihydropyrido[3,2-f][1,4]oxazepin-5(2H)-one To a solution of (3S)-3-methyl-7-nitro-3,4-dihydropyrido[3,2-f][1,4]oxazepin-5(2H)-one (228 mg, 1.02 mmol) obtained in Example (18c) in N,N-dimethylformamide (5 mL), sodium hydride (63% content, 53 mg, 1.39 mmol) was added under ice cooling, and the mixture was stirred at room temperature for 20 minutes. Subsequently, the mixture was cooled in an ice water bath. Methyl iodide (0.127 mL, 2.04 mmol) was added thereto, and the mixture was stirred at room temperature for 1 hour and 45 minutes. The reaction mixture was diluted by addition of ethyl acetate, washed with a 5% aqueous sodium chloride solution three times, and dried over anhydrous sodium sulfate. After filtration, the solvent was distilled off under reduced pressure, and the residue was purified in an automatic chromatography apparatus (n-hexane/ethyl acetate=100/0-0/100) to obtain the title compound (160 mg, yield: 66%).

$^1$H NMR spectrum (CDCl$_3$, 400 MHz) δ: 9.59 (1H, d, J=3.0 Hz), 9.22-9.21 (1H, m), 4.70 (1H, dd, J=12.8, 5.5 Hz), 4.47 (1H, d, J=12.8 Hz), 3.84-3.77 (1H, m), 3.25 (3H, s), 1.36 (3H, d, J=7.3 Hz).

(18e) (3S)-7-Amino-3,4-dimethyl-3,4-dihydropyrido[3,2-f][1,4]oxazepin-5(2H)-one

The title compound (175 mg, yield: quantitative) was obtained by production according to the method described in Example (3c) using (3S)-3,4-dimethyl-7-nitro-3,4-dihydropyrido[3,2-f][1,4]oxazepin-5(2H)-one (160 mg, 0.67 mmol) obtained in Example (18d).

$^1$H NMR spectrum (CD$_3$OD, 400 MHz) δ: 7.87-7.85 (1H, m), 7.79-7.78 (1H, m), 5.47-5.44 (1H, m), 4.45-4.39 (1H, m), 4.22 (1H, d, J=12.8 Hz), 3.92-3.84 (2H, m), 3.15 (3H, s), 1.32-1.23 (3H, m).

(18f) 5-Chloro-N-[(3S)-3,4-dimethyl-5-oxo-2,3,4,5-tetrahydropyrido[3,2-f][1,4]oxazepin-7-yl]-2-methoxybenzenesulfonamide The title compound (87 mg, yield: 63%) was obtained by production according to Example (1d) using (3S)-7-amino-3,4-dimethyl-3,4-dihydropyrido[3,2-f][1,4]oxazepin-5(2H)-one (69 mg, 0.34 mmol) obtained in Example (18e) and 5-chloro-2-methoxybenzenesulfonyl chloride (91 mg, 0.38 mmol).

$^1$H NMR spectrum (CDCl$_3$, 400 MHz) δ: 8.34 (2H, dd, J=12.1, 2.4 Hz), 7.74 (1H, d, J=2.4 Hz), 7.46 (1H, dd, J=8.8, 2.7 Hz), 7.10 (1H, s), 7.00 (1H, d, J=9.1 Hz), 4.51 (1H, dd, J=12.8, 5.5 Hz), 4.26 (1H, d, J=12.8 Hz), 4.07 (3H, s), 3.74-3.66 (1H, m), 3.17 (3H, s), 1.30 (3H, d, J=7.3 Hz).

MS spectrum (ES/APCI$^+$): 412 (M+H), 414 (M+2+H).

(Example 19) N-[(3S)-3,4-Dimethyl-5-oxo-2,3,4,5-tetrahydropyrido[3,2-f][1,4]oxazepin-7-yl]-5-fluoro-2-methoxybenzenesulfonamide

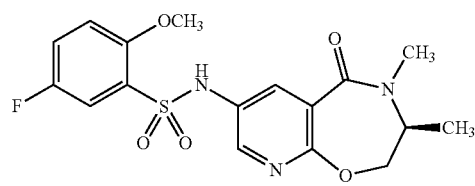 [SMILES: COc1ccc(F)cc1S(=O)(=O)Nc1cnc2c(c1)C(=O)N(C)[C@@H](C)CO2]

The title compound (81 mg, yield: 61%) was obtained by production according to Example (1d) using (3S)-7-amino-3,4-dimethyl-3,4-dihydropyrido[3,2-f][1,4]oxazepin-5(2H)-one (69 mg, 0.34 mmol) obtained in Example (18e) and 5-fluoro-2-methoxybenzenesulfonyl chloride (88 mg, 0.39 mmol).

$^1$H NMR spectrum (CDCl$_3$, 400 MHz) δ: 8.34 (2H, dd, J=14.9, 2.7 Hz), 7.49 (1H, dd, J=7.9, 3.0 Hz), 7.24-7.19 (1H, m), 7.08 (1H, s), 7.02 (1H, d, J=9.1, 4.3 Hz), 4.51 (1H, dd, J=12.8, 5.5 Hz), 4.25 (1H, d, J=12.8 Hz), 4.07 (3H, s), 3.73-3.66 (1H, m), 3.16 (3H, s), 1.29 (3H, d, J=6.7 Hz).

MS spectrum (ES/APCI$^+$): 396 (M+H).

(Example 20) 5-Chloro-N-[(3R)-3,4-dimethyl-5-oxo-2,3,4,5-tetrahydropyrido[3,2-f][1,4]oxazepin-7-yl]-2-methoxybenzenesulfonamide

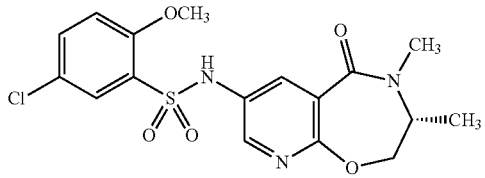

(20a) (2R)-2-[(2,4-Dimethoxybenzyl)amino]propan-1-ol

The title compound (3.10 g, yield: quantitative) was obtained by production according to the method described in Example (8a) using 2,4-dimethoxybenzaldehyde (2.25 g, 13.5 mmol) and (2R)-2-aminopropan-1-ol (1.02 g, 13.6 mmol).

$^1$H NMR spectrum (CDCl$_3$, 400 MHz) δ: 7.13 (1H, d, J=7.9 Hz), 6.50-6.42 (2H, m), 3.86-3.79 (7H, m), 3.77-3.61 (3H, m), 3.26 (1H, dd, J=10.6, 6.4 Hz), 2.84-2.76 (1H, m), 1.06 (3H, d, J=6.1 Hz).

(20b) (3R)-4-(2,4-Dimethoxybenzyl)-3-methyl-7-nitro-3,4-dihydropyrido[3,2-f][1,4]oxazepin-5(2H)-one The title compound (783 mg, yield for 2 steps: 61%) was obtained using 2-chloro-5-nitropyridine-3-carboxylic acid (700 mg, 3.46 mmol) and (2R)-2-[(2,4-dimethoxybenzyl)amino]propan-1-ol (778 mg, 3.45 mmol) obtained in Example (20a).

$^1$H NMR spectrum (CDCl$_3$, 400 MHz) δ: 9.62 (1H, d, J=3.0 Hz), 9.20 (1H, d, J=3.0 Hz), 7.33 (1H, d, J=8.5 Hz), 6.50-6.47 (2H, m), 4.95 (1H, d, J=14.0 Hz), 4.65-4.54 (2H, m), 4.31 (1H, d, J=13.4 Hz), 4.04-3.97 (1H, m), 3.84 (3H, s), 3.81 (3H, s), 1.23 (3H, d, J=7.3 Hz).

(20c) (3R)-3,4-Dimethyl-7-nitro-3,4-dihydropyrido[3,2-f][1,4]oxazepin-5(2H)-one

The title compound (120 mg, yield for 2 steps: 48%) was obtained by production according to the method described in Examples (18c) and (18d) using (3R)-4-(2,4-dimethoxybenzyl)-3-methyl-7-nitro-3,4-dihydropyrido[3,2-f][1,4]oxazepin-5(2H)-one (390 mg, 1.04 mmol) obtained in Example (20b).

$^1$H NMR spectrum (CDCl$_3$, 400 MHz) δ: 9.59 (1H, d, J=2.4 Hz), 9.21 (1H, d, J=2.4 Hz), 4.70 (1H, dd, J=13.1, 5.2 Hz), 4.47 (1H, d, J=13.1 Hz), 3.84-3.77 (1H, m), 3.25 (3H, s), 1.36 (3H, d, J=6.7 Hz).

(20d) (3R)-7-Amino-3,4-dimethyl-3,4-dihydropyrido[3,2-f][1,4]oxazepin-5(2H)-one

The title compound (87.9 mg, yield: 84%) was obtained by production according to the method described in Example (1c) using (3R)-3,4-dimethyl-7-nitro-3,4-dihydropyrido[3,2-f][1,4]oxazepin-5(2H)-one (120 mg, 0.51 mmol) obtained in Example (20c).

¹H NMR spectrum (CD₃OD, 400 MHz) δ: 7.86 (1H, d, J=3.0 Hz), 7.79 (1H, d, J=3.0 Hz), 4.42 (1H, dd, J=12.5, 7.0 Hz), 4.22 (1H, dd, J=12.5, 1.5 Hz), 3.93-3.86 (1H, m), 3.15 (3H, s), 1.27 (3H, d, J=6.7 Hz).

(20e) 5-Chloro-N-[(3R)-3,4-dimethyl-5-oxo-2,3,4,5-tetrahydropyrido[3,2-f][1,4]oxazepin-7-yl]-2-methoxybenzenesulfonamide The title compound (82 mg, yield: 96%) was obtained by production according to Example (1d) using (3R)-7-amino-3,4-dimethyl-3,4-dihydropyrido[3,2-f][1,4]oxazepin-5(2H)-one (43 mg, 0.21 mmol) obtained in Example (20d) and 5-chloro-2-methoxybenzenesulfonyl chloride (58 mg, 0.24 mmol).

¹H NMR spectrum (CDCl₃, 400 MHz) δ: 8.33 (2H, dd, J=8.8, 2.7 Hz), 7.73 (1H, d, J=3.0 Hz), 7.46 (1H, dd, J=8.8, 2.7 Hz), 7.02-6.97 (2H, m), 4.51 (1H, dd, J=12.8, 5.5 Hz), 4.26 (1H, d, J=12.8 Hz), 4.09 (3H, s), 3.73-3.67 (1H, m), 3.16 (3H, s), 1.30 (3H, d, J=6.7 Hz).

MS spectrum (ES/APCI⁺): 412 (M+H), 414 (M+2+H).

(Example 21) N-[(3R)-3,4-Dimethyl-5-oxo-2,3,4,5-tetrahydropyrido[3,2-f][1,4]oxazepin-7-yl]-5-fluoro-2-methoxybenzenesulfonamide

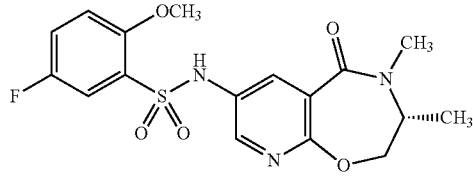 [SMILES: COc1ccc(F)cc1S(=O)(=O)Nc1cnc2c(c1)C(=O)N(C)[C@H](C)CO2]

The title compound (74 mg, yield: 90%) was obtained by production according to Example (1d) using (3R)-7-amino-3,4-dimethyl-3,4-dihydropyrido[3,2-f][1,4]oxazepin-5(2H)-one (43 mg, 0.21 mmol) obtained in Example (20d) and 5-fluoro-2-methoxybenzenesulfonyl chloride (56 mg, 0.25 mmol).

¹H NMR spectrum (CDCl₃, 400 MHz) δ: 8.33 (2H, dd, J=12.5, 2.7 Hz), 7.49 (1H, dd, J=7.3, 3.0 Hz), 7.24-7.19 (1H, m), 7.04-7.00 (2H, m), 4.51 (1H, dd, J=12.8, 5.5 Hz), 4.25 (1H, d, J=12.8 Hz), 4.08 (3H, s), 3.72-3.66 (1H, m), 3.16 (3H, s), 1.29 (3H, d, J=6.7 Hz).

MS spectrum (ES/APCI⁺): 396 (M+H).

(Example 22) 5-Chloro-2-methoxy-N-[(3S)-3-methyl-5-oxo-2,3,4,5-tetrahydropyrido[3,2-f][1,4]oxazepin-7-yl]benzenesulfonamide

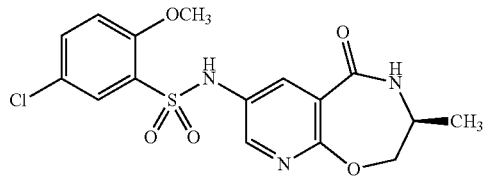 [SMILES: COc1ccc(Cl)cc1S(=O)(=O)Nc1cnc2c(c1)C(=O)N[C@@H](C)CO2]

(22a) (3S)-7-Amino-4-(2,4-dimethoxybenzyl)-3-methyl-3,4-dihydropyrido[3,2-f][1,4]oxazepin-5(2H)-one To a mixture of (3S)-4-(2,4-dimethoxybenzyl)-3-methyl-7-nitro-3,4-dihydropyrido[3,2-f][1,4]oxazepin-5(2H)-one (330 mg, 0.88 mmol) obtained in Example (18b) in tetrahydrofuran (4 mL) and methanol (4 mL), nickel(II) chloride hexahydrate (432 mg, 1.82 mmol) was added. Subsequently, the mixture was cooled in an ice water bath. Sodium borohydride (134 mg, 3.54 mmol) was added thereto over 10 minutes, and then, the mixture was stirred at room temperature for 2 hours. The reaction mixture was diluted by addition of acetone, then Celite 545(R) (approximately 0.6 g) was added thereto, and the mixture was stirred at room temperature for 1 hour. The reaction mixture was filtered, and the solvent in the filtrate was distilled off under reduced pressure to obtain the title compound (303 mg, yield: quantitative).

¹H NMR spectrum (CDCl₃, 400 MHz) δ: 8.10 (1H, d, J=3.0 Hz), 7.89 (1H, d, J=3.0 Hz), 7.31-7.26 (1H, m), 6.49-6.44 (2H, m), 4.93 (1H, d, J=14.6 Hz), 4.57 (1H, d, J=14.6 Hz), 4.38 (1H, dd, J=12.8, 5.8 Hz), 4.12 (1H, d, J=12.8 Hz), 4.00-3.74 (7H, m), 3.57 (2H, br s), 1.21 (3H, d, J=7.3 Hz).

(22b) 5-Chloro-N-[(3S)-4-(2,4-dimethoxybenzyl)-3-methyl-5-oxo-2,3,4,5-tetrahydropyrido[3,2-f][1,4]oxazepin-7-yl]-2-methoxybenzenesulfonamide To a mixture of (3S)-7-amino-4-(2,4-dimethoxybenzyl)-3-methyl-3,4-dihydropyrido[3,2-f][1,4]oxazepin-5(2H)-one (150 mg, 0.44 mmol) obtained in Example (22a) and pyridine (3 mL, 37 mmol), 5-chloro-2-methoxybenzenesulfonyl chloride (121 mg, 0.50 mmol) was added, and the mixture was stirred at 80° C. for 1 hour in an oil bath. The reaction mixture was cooled and then concentrated under reduced pressure, and the residue was purified in an automatic chromatography apparatus (ethyl acetate/methanol=100/0-85/15) to obtain the title compound (200 mg, yield: 83%).

¹H NMR spectrum (CDCl₃, 400 MHz) δ: 8.38 (1H, d, J=2.4 Hz), 8.31 (1H, d, J=2.4 Hz), 7.74 (1H, d, J=2.4 Hz), 7.47 (1H, dd, J=9.1, 2.4 Hz), 7.21 (1H, d, J=9.1 Hz), 7.01 (1H, d, J=9.1 Hz), 6.92 (1H, s), 6.47-6.43 (2H, m), 4.91 (1H, d, J=15.2 Hz), 4.51-4.41 (2H, m), 4.15-4.11 (1H, m), 4.09 (3H, s), 3.85-3.80 (1H, m), 3.80-3.79 (6H, m), 1.17 (3H, d, J=6.7 Hz).

(22c) 5-Chloro-2-methoxy-N-[(3S)-3-methyl-5-oxo-2,3,4,5-tetrahydropyrido[3,2-f][1,4]oxazepin-7-yl]benzenesulfonamide To a solution of 5-chloro-N-[(3S)-4-(2,4-dimethoxybenzyl)-3-methyl-5-oxo-2,3,4,5-tetrahydropyrido[3,2-f][1,4]oxazepin-7-yl]-2-methoxybenzenesulfonamide (200 mg, 0.36 mmol) obtained in Example (22b) and anisole (0.1 mL, 0.9 mmol) in chloroform (3 mL), trifluoroacetic acid (1 mL, 13 mmol) and trifluoromethanesulfonic acid (0.1 mL, 1.1 mmol) were added, and the mixture was stirred at room temperature for 1 hour. The reaction mixture was concentrated under reduced pressure, and then, the residue was diluted with chloroform, washed with a saturated aqueous solution of sodium bicarbonate and a saturated aqueous solution of sodium chloride, and dried over anhydrous sodium sulfate. After filtration, the solvent was distilled off under reduced pressure. To the residue, diisopropyl ether was added, and the precipitated solid was collected by filtration, washed with diisopropyl ether, and then dried to obtain the title compound (105 mg, yield: 72%).

¹H NMR spectrum (CDCl₃, 400 MHz) δ: 8.31 (1H, d, J=3.0 Hz), 8.22 (1H, d, J=2.4 Hz), 7.74 (1H, d, J=2.4 Hz), 7.47 (1H, dd, J=9.1, 2.4 Hz), 7.02-6.95 (2H, m), 6.10 (1H, br s), 4.41 (1H, d, J=12.1 Hz), 4.23 (1H, dd, J=12.8, 7.3 Hz), 4.08 (3H, s), 1.31 (3H, d, J=6.7 Hz).

MS spectrum (ES/APCI⁺): 398 (M+H), 400 (M+2+H).

(Example 23) 5-Fluoro-2-methoxy-N-[(3S)-3-methyl-5-oxo-2,3,4,5-tetrahydropyrido[3,2-f][1,4]oxazepin-7-yl]benzenesulfonamide

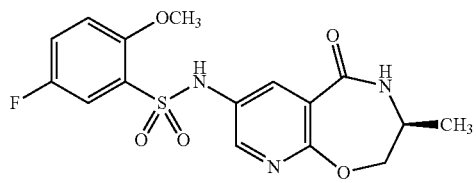 [SMILES: COc1ccc(F)cc1S(=O)(=O)Nc1cnc2c(c1)C(=O)N[C@@H](C)CO2]

(23a) N-[(3S)-4-(2,4-Dimethoxybenzyl)-3-methyl-5-oxo-2,3,4,5-tetrahydropyrido[3,2-f][1,4]oxazepin-7-yl]-5-fluoro-2-methoxybenzenesulfonamide To a mixture of (3S)-7-amino-4-(2,4-dimethoxybenzyl)-3-methyl-3,4-dihydropyrido[3,2-f][1,4]oxazepin-5(2H)-one (150 mg, 0.44 mmol) obtained in Example (22a) and pyridine (3 mL, 37 mmol), 5-fluoro-2-methoxybenzenesulfonyl chloride (120 mg, 0.53 mmol) was added, and the mixture was stirred at 80° C. for 2 hours and 20 minutes in an oil bath. The reaction mixture was cooled and then concentrated under reduced pressure, and the residue was purified in an automatic chromatography apparatus (ethyl acetate/methanol=100/0-85/15) to obtain the title compound (189 mg, yield: 81%).

¹H NMR spectrum (CDCl₃, 400 MHz) δ: 8.39 (1H, d, J=3.0 Hz), 8.30-8.29 (1H, m), 7.50 (1H, dd, J=7.9, 3.0 Hz), 7.31-7.20 (2H, m), 7.03 (1H, dd, J=9.1, 3.6 Hz), 6.95 (1H, br s), 6.46-6.44 (2H, m), 4.91 (1H, d, J=14.6 Hz), 4.49 (1H, d, J=14.6 Hz), 4.43 (1H, dd, J=12.8, 5.5 Hz), 4.16-4.11 (1H, m), 4.09 (3H, s), 3.84-3.79 (7H, m), 1.16 (3H, d, J=6.7 Hz).

(23b) 5-Fluoro-2-methoxy-N-[(3S)-3-methyl-5-oxo-2,3,4,5-tetrahydropyrido[3,2-f][1,4]oxazepin-7-yl]benzenesulfonamide To a solution of N-[(3S)-4-(2,4-dimethoxybenzyl)-3-methyl-5-oxo-2,3,4,5-tetrahydropyrido[3,2-f][1,4]oxazepin-7-yl]-5-fluoro-2-methoxybenzenesulfonamide (189 mg, 0.35 mmol) obtained in Example (23a) and anisole (0.1 mL, 0.9 mmol) in chloroform (3 mL), trifluoroacetic acid (1 mL, 13 mmol) and trifluoromethanesulfonic acid (0.1 mL, 1.1 mmol) were added, and the mixture was stirred at room temperature for 1 hour. The reaction mixture was concentrated under reduced pressure, and then, the residue was diluted with chloroform, washed with a saturated aqueous solution of sodium bicarbonate and a saturated aqueous solution of sodium chloride, and dried over anhydrous sodium sulfate. After filtration, the solvent was distilled off under reduced pressure. To the residue, diisopropyl ether was added, and the precipitated solid was collected by filtration, washed with diisopropyl ether, and then dried to obtain the title compound (73.1 mg, yield: 54%).

¹H NMR spectrum (CDCl₃, 400 MHz) δ: 8.31 (1H, d, J=2.4 Hz), 8.23 (1H, d, J=2.4 Hz), 7.49 (1H, dd, J=7.6, 3.3 Hz), 7.25-7.20 (1H, m), 7.07-7.00 (2H, m), 6.14 (1H, br s), 4.41 (1H, d, J=11.5 Hz), 4.22 (1H, dd, J=12.8, 7.3 Hz), 4.07 (3H, s), 3.88-3.82 (1H, m), 1.30 (3H, d, J=7.3 Hz).

MS spectrum (ES/APCI⁺): 382 (M+H).

(Example 24) 5-Chloro-N-[(3S)-3-ethyl-4-methyl-5-oxo-2,3,4,5-tetrahydropyrido[3,2-f][1,4]oxazepin-7-yl]-2-methoxybenzenesulfonamide

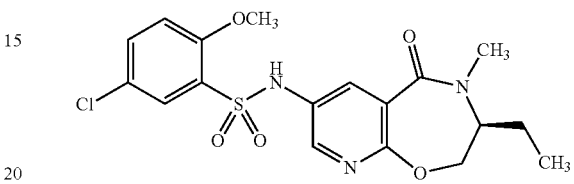

(24a) (2S)-2-[(2,4-Dimethoxybenzyl)amino]butan-1-ol

The title compound (2.54 g, yield: 97%) was obtained by production according to the method described in Example (8a) using 2,4-dimethoxybenzaldehyde (1.81 g, 10.9 mmol) and (2S)-2-aminobutan-1-ol (0.98 g, 11.0 mmol).

¹H NMR spectrum (CDCl₃, 400 MHz) δ: 7.12 (1H, d, J=8.5 Hz), 6.48-6.41 (2H, m), 3.83 (3H, s), 3.80 (3H, s), 3.71 (2H, s), 3.66 (1H, dd, J=10.3, 4.3 Hz), 3.31 (1H, dd, J=10.3, 6.1 Hz), 2.60-2.52 (1H, m), 1.54-1.38 (2H, m), 0.90 (3H, t, J=7.3 Hz).

(24b) (3S)-7-Bromo-4-(2,4-dimethoxybenzyl)-3-ethyl-3,4-dihydropyrido[3,2-f][1,4]oxazepin-5(2H)-one The title compound (379 mg, yield for 2 steps: 78%) was obtained by production according to the method described in Examples (1a) and (1b) using 5-bromo-2-chloropyridine-3-carboxylic acid (500 mg, 2.11 mmol) and (2S)-2-[(2,4-dimethoxybenzyl)amino]butan-1-ol (506 mg, 2.11 mmol) obtained in Example (24a).

¹H NMR spectrum (CDCl₃, 400 MHz) δ: 8.90 (1H, d, J=2.4 Hz), 8.38 (1H, d, J=2.4 Hz), 7.34-7.31 (1H, m), 6.49-6.46 (2H, m), 5.08 (1H, d, J=14.6 Hz), 4.62 (1H, dd, J=13.1, 5.2 Hz), 4.41 (1H, d, J=14.6 Hz), 4.11-4.09 (1H, m), 3.83 (3H, s), 3.81 (3H, s), 3.69-3.63 (1H, m), 1.62-1.52 (2H, m), 1.00 (3H, t, J=7.3 Hz).

(24c) (3S)-7-Bromo-3-ethyl-4-methyl-3,4-dihydropyrido[3,2-f][1,4]oxazepin-5(2H)-one The title compound (85.1 mg, yield for 2 steps: 66%) was obtained by production according to the method described in Examples (18c) and (18d) using (3S)-7-bromo-4-(2,4-dimethoxybenzyl)-3-ethyl-3,4-dihydropyrido[3,2-f][1,4]oxazepin-5(2H)-one (189 mg, 0.45 mmol) obtained in Example (24b).

¹H NMR spectrum (CDCl₃, 400 MHz) δ: 8.86 (1H, d, J=2.4 Hz), 8.39 (1H, d, J=2.4 Hz), 4.72 (1H, dd, J=13.1, 5.2 Hz), 4.30 (1H, d, J=12.8 Hz), 3.48-3.41 (1H, m), 3.22 (3H, s), 1.72-1.64 (2H, m), 1.05 (3H, t, J=7.6 Hz).

(24d) 5-Chloro-N-[(3S)-3-ethyl-4-methyl-5-oxo-2,3,4,5-tetrahydropyrido[3,2-f][1,4]oxazepin-7-yl]-2-methoxybenzenesulfonamide The title compound (63.2 mg, yield: 50%) was obtained by production according to the method described in Example (5d) using (3S)-7-bromo-3-ethyl-4-methyl-3,4-dihydropyrido[3,2-f][1,4]oxazepin-5(2H)-one (85.1 mg, 0.30 mmol) obtained in Example (24c) and 5-chloro-2-methoxybenzenesulfonamide (75.8 mg, 0.34 mmol) obtained in Example (5a).

$^1$H NMR spectrum (CDCl$_3$, 400 MHz) δ: 8.39-8.31 (2H, m), 7.74 (1H, d, J=3.0 Hz), 7.46 (1H, dd, J=8.8, 2.7 Hz), 7.13 (1H, br s), 6.99 (1H, d, J=9.1 Hz), 4.67 (1H, dd, J=13.4, 5.5 Hz), 4.22 (1H, d, J=12.8 Hz), 4.07 (3H, s), 3.43-3.37 (1H, m), 3.19 (3H, s), 1.70-1.60 (2H, m), 1.02 (3H, t, J=7.3 Hz).

MS spectrum (ES/APCI$^+$): 426 (M+H), 428 (M+2+H).

(Example 25) 5-Chloro-N-[(3S)-3-ethyl-5-oxo-2,3,4,5-tetrahydropyrido[3,2-f][1,4]oxazepin-7-yl]-2-methoxybenzenesulfonamide

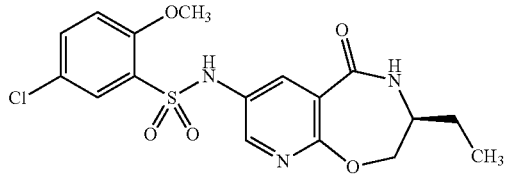 [SMILES: CC[C@H]1COc2ncc(NS(=O)(=O)c3cc(Cl)ccc3OC)cc2C(=O)N1]

The title compound (133 mg, yield for 2 steps: 72%) was obtained by production according to the method described in Examples (5d) and (9) using (3S)-7-bromo-4-(2,4-dimethoxybenzyl)-3-ethyl-3,4-dihydropyrido[3,2-f][1,4]oxazepin-5(2H)-one (189 mg, 0.45 mmol) obtained in Example (24b) and 5-chloro-2-methoxybenzenesulfonamide (104 mg, 0.47 mmol) obtained in Example (5a).

$^1$H NMR spectrum (CDCl$_3$, 400 MHz) δ: 8.31 (1H, d, J=2.4 Hz), 8.25 (1H, d, J=3.0 Hz), 7.75 (1H, d, J=3.0 Hz), 7.47 (1H, dd, J=9.1, 2.4 Hz), 7.29-7.25 (1H, m), 7.00 (1H, d, J=9.1 Hz), 6.27 (1H, br s), 4.42 (1H, d, J=12.8 Hz), 4.33 (1H, dd, J=12.8, 6.7 Hz), 4.07 (3H, s), 3.59-3.53 (1H, m), 1.73-1.60 (2H, m), 1.05 (3H, t, J=7.3 Hz).

MS spectrum (ES/APCI$^+$): 412 (M+H), 414 (M+2+H).

(Example 26) 5-Chloro-2-methoxy-N-[(3S)-5-oxo-3-(propan-2-yl)-2,3,4,5-tetrahydropyrido[3,2-f][1,4]oxazepin-7-yl]benzenesulfonamide

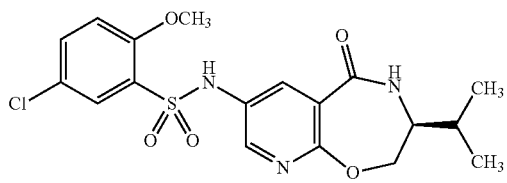 [SMILES: COc1ccc(Cl)cc1S(=O)(=O)Nc1cnc2c(c1)C(=O)N[C@@H](C(C)C)CO2]

(26a) (2S)-2-[(2,4-Dimethoxybenzyl)amino]-3-methylbutan-1-ol

The title compound (2.53 g, yield: 99%) was obtained by production according to the method described in Examples (8a) using 2,4-dimethoxybenzaldehyde (1.68 g, 10.9 mmol) and (2S)-2-amino-3-methylbutan-1-ol (1.04 g, 10.1 mmol).

$^1$H NMR spectrum (CDCl$_3$, 400 MHz) δ: 7.11 (1H, d, J=7.9 Hz), 6.50-6.42 (2H, m), 3.88-3.81 (7H, m), 3.71 (2H, d, J=4.3 Hz), 3.65 (1H, dd, J=10.3, 4.3 Hz), 3.35 (1H, dd, J=10.3, 6.7 Hz), 2.40-2.35 (1H, m), 1.84-1.73 (1H, m), 0.95 (3H, d, J=6.7 Hz), 0.89 (3H, d, J=6.7 Hz).

(26b) (3S)-7-Bromo-4-(2,4-dimethoxybenzyl)-3-(propan-2-yl)-3,4-dihydropyrido[3,2-f][1,4]oxazepin-5(2H)-one The title compound (1.43 g, yield for 2 steps: 77%) was obtained by production according to the method described in Examples (1a) and (1b) using 5-bromo-2-chloropyridine-3-carboxylic acid (1.00 g, 4.23 mmol) and (2S)-2-[(2,4-dimethoxybenzyl)amino]-3-methylbutan-1-ol (1.07 g, 4.22 mmol) obtained in Example (26a).

$^1$H NMR spectrum (CDCl$_3$, 400 MHz) δ: 8.84 (1H, d, J=2.4 Hz), 8.37 (1H, d, J=2.4 Hz), 7.38-7.35 (1H, m), 6.50-6.43 (2H, m), 5.33 (1H, d, J=14.0 Hz), 4.66 (1H, dd, J=12.8, 5.5 Hz), 4.17-4.11 (1H, m), 4.00 (1H, d, J=12.8 Hz), 3.83 (3H, s), 3.81 (3H, s), 3.40 (1H, dd, J=10.9, 5.5 Hz), 1.85-1.78 (1H, m), 1.05 (3H, d, J=6.7 Hz), 1.02 (3H, d, J=6.7 Hz).

(26c) 5-Chloro-2-methoxy-N-[(3S)-5-oxo-3-(propan-2-yl)-2,3,4,5-tetrahydropyrido[3,2-f][1,4]oxazepin-7-yl]benzenesulfonamide The title compound (186 mg, yield for 2 steps: 53%) was obtained by production according to the method described in Examples (5d) and (9) using (3S)-7-bromo-4-(2,4-dimethoxybenzyl)-3-(propan-2-yl)-3,4-dihydropyrido[3,2-f][1,4]oxazepin-5(2H)-one (355 mg, 0.82 mmol) obtained in Example (26b) and 5-chloro-2-methoxybenzenesulfonamide (199 mg, 0.90 mmol) obtained in Example (5a).

$^1$H NMR spectrum (CDCl$_3$, 400 MHz) δ: 8.29 (2H, dd, J=16.4, 3.0 Hz), 7.75 (1H, d, J=2.4 Hz), 7.47 (1H, dd, J=8.8, 2.7 Hz), 7.10 (1H, s), 7.00 (1H, d, J=8.5 Hz), 6.36-6.33 (1H, m), 4.47-4.39 (2H, m), 4.07 (3H, s), 3.35-3.29 (1H, m), 1.95-1.88 (1H, m), 1.08-1.00 (6H, m).

MS spectrum (ES/APCI$^+$): 426 (M+H), 428 (M+2+H).

(Example 27) 5-Chloro-N-[(3S)-3-(hydroxymethyl)-5-oxo-2,3,4,5-tetrahydropyrido[3,2-f][1,4]oxazepin-7-yl]-2-methoxybenzenesulfonamide

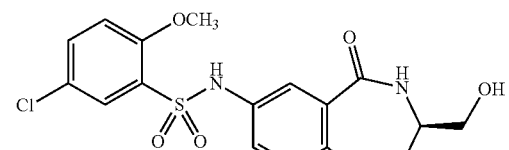

(27a) (2R)-3-(Benzyloxy)-2-[(2,4-dimethoxybenzyl)amino]propan-1-ol

The title compound (4.18 g, yield: quantitative) was obtained by production according to the method described in Example (8a) using 2,4-dimethoxybenzaldehyde (2.00 g, 12.0 mmol) and (2R)-2-amino-3-(benzyloxy)propan-1-ol (2.18 g, 12.0 mmol).

¹H NMR spectrum (CDCl₃, 400 MHz) δ: 7.36-2.26 (5H, m), 7.12 (1H, d, J=7.8 Hz), 6.45-6.42 (2H, m), 4.46 (2H, s), 3.81-3.68 (9H, m), 3.52 (2H, d, J=5.9 Hz), 3.44 (1H, dd, J=11.0, 4.3 Hz), 2.95-2.90 (1H, m).

(27b) N-[(2R)-1-(Benzyloxy)-3-hydroxypropan-2-yl]-2-chloro-N-(2,4-dimethoxybenzyl)-5-nitropyridine-3-carboxamide To a suspension of 2-chloro-5-nitropyridine-3-carboxylic acid (1.21 g, 5.97 mmol) in methylene chloride (30 mL), oxalyl chloride (0.64 mL, 7.5 mmol) and N,N-dimethylformamide (0.024 mL, 0.31 mmol) were added at room temperature, and the mixture was stirred at the same temperature as above for 30 minutes. The reaction mixture was concentrated under reduced pressure to prepare a crude product of 2-chloro-5-nitropyridine-3-carboxylic acid chloride. To a solution of (2R)-3-(benzyloxy)-2-[(2,4-dimethoxybenzyl)amino]propan-1-ol (1.98 g, 5.97 mmol) obtained in Example (27a) and N,N-diisopropylethylamine (2.05 mL, 12.1 mmol) in tetrahydrofuran (15 mL), a solution of the crude product of 2-chloro-5-nitropyridine-3-carboxylic acid chloride in tetrahydrofuran (15 mL) was added over 10 minutes under ice cooling, and the mixture was stirred at the same temperature as above for 10 minutes. To the reaction mixture, water (0.05 mL) was added, and then, the mixture was concentrated under reduced pressure. The concentrated mixture was diluted by addition of water, followed by extraction with ethyl acetate. The organic layer was washed with water and a saturated aqueous solution of sodium chloride and dried over anhydrous magnesium sulfate. After filtration, the solvent was distilled off under reduced pressure, and the residue was purified by silica gel column chromatography (n-hexane/ethyl acetate=3/2-2/3) to obtain the title compound (2.74 g, yield: 89%).
¹H NMR spectrum (CDCl₃, 400 MHz) δ: 9.21-9.18 (1H, m), 8.59-8.25 (1H, m), 7.58-6.98 (6H, m), 6.54-6.30 (2H, m), 4.97-2.83 (14H, m).

(27c) (3S)-3-[(Benzyloxy)methyl]-4-(2,4-dimethoxybenzyl)-7-nitro-3,4-dihydropyrido[3,2-f][1,4]oxazepin-5(2H)-one A solution of sodium bis(trimethylsilyl)amide in tetrahydrofuran (ca. 1.9 mol/L, 4.2 mL, 8.0 mmol) was diluted with tetrahydrofuran (130 mL). A solution of N-[(2R)-1-(benzyloxy)-3-hydroxypropan-2-yl]-2-chloro-N-(2,4-dimethoxybenzyl)-5-nitropyridine-3-carboxamide (2.73 g, 5.29 mmol) obtained in Example (27b) in tetrahydrofuran (130 mL) was added thereto over 40 minutes under ice cooling, and the mixture was stirred at the same temperature as above for 10 minutes and further stirred at room temperature for 40 minutes. To the reaction mixture, a saturated aqueous solution of ammonium chloride (50 mL) was added, and then, the mixture was concentrated into approximately ⅕ of the amount under reduced pressure. The concentrated mixture was diluted by addition of water, followed by extraction with ethyl acetate twice. The organic layer was washed with water and a saturated aqueous solution of sodium chloride and dried over anhydrous magnesium sulfate. After filtration, the solvent was distilled off under reduced pressure, and the residue was purified by silica gel column chromatography (n-hexane/ethyl acetate=1/1) to obtain the title compound (1.93 g, yield: 76%).
¹H NMR spectrum (CDCl₃, 400 MHz) δ: 9.53 (1H, d, J=3.1 Hz), 9.12 (1H, d, J=3.1 Hz), 7.35-7.19 (6H, m), 6.49-6.46 (2H, m), 5.06 (1H, d, J=14.1 Hz), 4.88 (1H, dd, J=12.9, 5.1 Hz), 4.52 (1H, d, J=14.1 Hz), 4.46 (1H, d, J=11.7 Hz), 4.40 (1H, d, J=11.7 Hz), 4.26 (1H, d, J=12.9 Hz), 4.16-4.10 (1H, m), 3.83 (6H, s) 3.56 (1H, dd, J=9.4, 7.4 Hz), 3.48 (1H, dd, J=9.4, 6.1 Hz).

(27d) (3S)-7-Amino-3-[(benzyloxy)methyl]-4-(2,4-dimethoxybenzyl)-3,4-dihydropyrido[3,2-f][1,4]oxazepin-5(2H)-one A mixture of (3S)-3-[(benzyloxy)methyl]-4-(2,4-dimethoxybenzyl)-7-nitro-3,4-dihydropyrido[3,2-f][1,4]oxazepin-5(2H)-one (1.93 g, 4.03 mmol) obtained in Example (27c) and 10% palladium carbon (water content: 54.6%, 0.48 g) in tetrahydrofuran (26 mL) and ethanol (13 mL) was stirred at room temperature for 5 hours at normal pressure under the hydrogen atmosphere. Hydrogen in the reaction container was replaced with nitrogen, and then, the reaction mixture was filtered through pad of Celite 545(R). The solvent in the filtrate was distilled off under reduced pressure, and the residue was purified by silica gel column chromatography (ethyl acetate/methanol=1/0-20/1) to obtain the title compound (1.57 g, yield: 87%).
¹H NMR spectrum (CDCl₃, 400 MHz) δ: 8.09 (1H, d, J=3.1 Hz), 7.87 (1H, d, J=3.1 Hz), 7.35-7.26 (6H, m), 6.46-6.44 (2H, m), 5.09 (1H, d, J=14.9 Hz), 4.67 (1H, dd, J=12.7, 5.3 Hz), 4.53-4.42 (3H, m), 4.08-3.97 (2H, m), 3.80 (6H, s), 3.63 (1H, dd, J=9.6, 7.2 Hz), 3.56-3.47 (3H, m).

(27e) N-[(3S)-3-[(Benzyloxy)methyl]-4-(2,4-dimethoxybenzyl)-5-oxo-2,3,4,5-tetrahydropyrido[3,2-f][1,4]oxazepin-7-yl]-5-chloro-2-methoxybenzenesulfonamide To a mixture of (3S)-7-amino-3-[(benzyloxy)methyl]-4-(2,4-dimethoxybenzyl)-3,4-dihydropyrido[3,2-f][1,4]oxazepin-5(2H)-one (226 mg, 0.50 mmol) obtained in Example (27d) and pyridine (0.81 mL, 37.3 mmol), 5-chloro-2-methoxybenzenesulfonyl chloride (134 mg, 0.55 mmol) was added, and the mixture was stirred at 80° C. for 30 minutes in an oil bath. The reaction mixture was cooled and then concentrated under reduced pressure, and the concentrated mixture was diluted by addition of water, followed by extraction with ethyl acetate. The organic layer was washed with water and a saturated aqueous solution of sodium chloride and dried over anhydrous magnesium sulfate. After filtration, the solvent was distilled off under reduced pressure, and the residue was purified by silica gel column chromatography (ethyl acetate) to obtain the title compound (323 mg, yield: 98%).
¹H NMR spectrum (CDCl₃, 400 MHz) δ: 8.36 (1H, d, J=2.7 Hz), 8.30 (1H, d, J=2.7 Hz), 7.74 (1H, d, J=2.7 Hz), 7.46 (1H, dd, J=9.0, 2.7 Hz), 7.34-7.21 (6H, m), 7.00 (1H, d, J=9.0 Hz), 6.90 (1H, br s), 6.45-6.43 (2H, m), 5.04 (1H, d, J=14.5 Hz), 4.73 (1H, dd, J=12.9, 5.1 Hz), 4.49-4.39 (3H, m), 4.08-4.05 (4H, m), 4.01-3.97 (1H, m), 3.79 (3H, s), 3.77 (3H, s), 3.55 (1H, dd, J=9.6, 7.6 Hz), 3.43 (1H, dd, J=9.6, 6.5 Hz).

(27f) 5-Chloro-N-[(3S)-3-(hydroxymethyl)-5-oxo-2,3,4,5-tetrahydropyrido[3,2-f][1,4]oxazepin-7-yl]-2-methoxybenzenesulfonamide To a solution of N-[(3S)-3-[(benzyloxy)methyl]-4-(2,4-dimethoxybenzyl)-5-oxo-2,3,4,5-tetrahydropyrido[3,2-f][1,4]oxazepin-7-yl]-5-chloro-2-methoxybenzenesulfonamide (324 mg, 0.50 mmol) obtained in Example (27e) and anisole (0.17 mL, 1.6 mmol) in chloroform (2.5 mL), trifluoroacetic acid (0.76 mL, 9.9 mmol) and trifluoromethanesulfonic acid (0.13 mL, 1.5 mmol) were added, and the mixture was stirred at room temperature for 3 hours. The reaction mixture was poured into a mixture of sodium bicarbonate (0.83 g, 9.9 mmol) and water (5 mL), and the mixture was stirred at room temperature for 30 minutes. To the reaction mixture, sodium bicarbonate (0.13 g, 1.5 mmol) was further added, and then, the mixture was concentrated under reduced pressure. The concentrated mixture was diluted by addition of tetrahydrofuran (5 mL). 2 N sulfuric acid (0.50 mL, 1.0 mmol) was added thereto, and the mixture was stirred at room temperature for 10 minutes. To the reaction mixture, a 2 N aqueous sodium hydroxide solution (0.50 mL, 1.0 mmol) was added, and the mixture was concentrated under reduced pressure. To the concentrated mixture, a saturated aqueous solution of sodium chloride was added, and the mixture was washed with ethyl acetate. The aqueous layer was rendered acidic by the addition of 1 N hydrochloric acid, followed by extraction with a mixed solvent of chloroform/isopropanol=3/1 twice. The organic layer was dried over anhydrous magnesium sulfate. After filtration, the solvent was distilled off under reduced pressure. To the residue, ethyl acetate was added, and the precipitated solid was collected by filtration, washed with ethyl acetate, and then dried to obtain the title compound (162 mg, yield: 79%).

$^1$H NMR spectrum (DMSO-d6, 400 MHz) δ: 10.29 (1H, br s), 8.35 (1H, br d, J=4.3 Hz), 8.24 (1H, d, J=3.1 Hz), 8.07 (1H, d, J=3.1 Hz), 7.68-7.64 (2H, m), 7.25 (1H, d, J=9.0 Hz), 5.04 (1H, t, J=5.5 Hz), 4.40-4.32 (2H, m), 3.87 (3H, s), 3.48-3.36 (3H, m).

MS spectrum (ES/APCI): 412 (M−H), 414 (M+2−H).

(Example 28) 5-Fluoro-N-[(3S)-3-(hydroxymethyl)-5-oxo-2,3,4,5-tetrahydropyrido[3,2-f][1,4]oxazepin-7-yl]-2-methoxybenzenesulfonamide

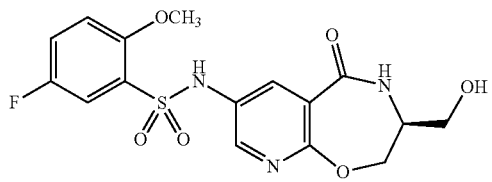

(28a) N-[(3S)-3-[(Benzyloxy)methyl]-4-(2,4-dimethoxybenzyl)-5-oxo-2,3,4,5-tetrahydropyrido[3,2-f][1,4]oxazepin-7-yl]-5-fluoro-2-methoxybenzenesulfonamide To a mixture of (3S)-7-amino-3-[(benzyloxy)methyl]-4-(2,4-dimethoxybenzyl)-3,4-dihydropyrido[3,2-f][1,4]oxazepin-5(2H)-one (310 mg, 0.69 mmol) obtained in Example (27d) and pyridine (1.1 mL, 13.7 mmol), 5-fluoro-2-methoxybenzenesulfonyl chloride (171 mg, 0.76 mmol) was added, and the mixture was stirred at 80° C. for 30 minutes in an oil bath. The reaction mixture was cooled and then concentrated under reduced pressure, and the concentrated mixture was diluted by addition of water, followed by extraction with ethyl acetate. The organic layer was washed with water and a saturated aqueous solution of sodium chloride and dried over anhydrous magnesium sulfate. After filtration, the solvent was distilled off under reduced pressure, and the residue was purified by silica gel column chromatography (ethyl acetate) to obtain the title compound (425 mg, yield: 97%).

$^1$H NMR spectrum (CDCl$_3$, 400 MHz) δ: 8.37 (1H, d, J=2.7 Hz), 8.29 (1H, d, J=2.7 Hz), 7.49 (1H, dd, J=7.4, 3.1 Hz), 7.34-7.19 (7H, m), 7.02 (1H, dd, J=9.0, 3.9 Hz), 6.97 (1H, br s), 6.45-6.42 (2H, m), 5.03 (1H, d, J=14.5 Hz), 4.72 (1H, dd, J=12.7, 5.3 Hz), 4.48-4.39 (3H, m), 4.07-3.96 (5H, m), 3.79 (3H, s), 3.77 (3H, s), 3.54 (1H, dd, J=9.6, 7.4 Hz), 3.42 (1H, dd, J=9.6, 6.5 Hz).

(28b) 5-Fluoro-N-[(3S)-3-(hydroxymethyl)-5-oxo-2,3,4,5-tetrahydropyrido[3,2-f][1,4]oxazepin-7-yl]-2-methoxybenzenesulfonamide To a solution of N-[(3S)-3-[(benzyloxy)methyl]-4-(2,4-dimethoxybenzyl)-5-oxo-2,3,4,5-tetrahydropyrido[3,2-f][1,4]oxazepin-7-yl]-5-fluoro-2-methoxybenzenesulfonamide (213 mg, 0.33 mmol) obtained in Example (28a) and anisole (0.11 mL, 1.0 mmol) in chloroform (1.7 mL), trifluoroacetic acid (0.51 mL, 6.6 mmol) and trifluoromethanesulfonic acid (0.09 mL, 1.0 mmol) were added, and the mixture was stirred at room temperature for 4 hours. The reaction mixture was poured into a mixture of sodium bicarbonate (0.65 g, 7.7 mmol) and water (3.4 mL), and the mixture was stirred at room temperature for 30 minutes. The reaction mixture was concentrated under reduced pressure, and the concentrated mixture was diluted by addition of tetrahydrofuran (3.4 mL). 2 N sulfuric acid (0.34 mL, 0.68 mmol) was added thereto, and the mixture was stirred at room temperature for 1 hour. To the reaction mixture, a 2 N aqueous sodium hydroxide solution (0.34 mL, 0.68 mmol) was added, and the mixture was concentrated under reduced pressure. To the concentrated mixture, a saturated aqueous solution of sodium chloride was added, and the mixture was washed with ethyl acetate. The aqueous layer was rendered acidic by the addition of 1 N hydrochloric acid, followed by extraction with a mixed solvent of chloroform/isopropanol=3/1 twice. The organic layer was dried over anhydrous magnesium sulfate. After filtration, the solvent was distilled off under reduced pressure. To the residue, ethyl acetate was added, and the precipitated solid was collected by filtration, washed with ethyl acetate, and then dried to obtain the title compound (113 mg, yield: 85%).

$^1$H NMR spectrum (DMSO-d6, 400 MHz) δ: 10.27 (1H, br s), 8.34 (1H, br d, J=3.9 Hz), 8.24 (1H, d, J=2.7 Hz), 8.07 (1H, d, J=2.7 Hz), 7.51-7.47 (2H, m), 7.26-7.22 (1H, m), 5.04 (1H, t, J=5.5 Hz), 4.38-4.32 (2H, m), 3.86 (3H, s), 3.50-3.38 (3H, m).

MS spectrum (ES/APCI$^+$): 398 (M+H).

(Example 29) 5-Bromo-N-[(3S)-3-(hydroxymethyl)-5-oxo-2,3,4,5-tetrahydropyrido[3,2-f][1,4]oxazepin-7-yl]-2-methoxybenzenesulfonamide

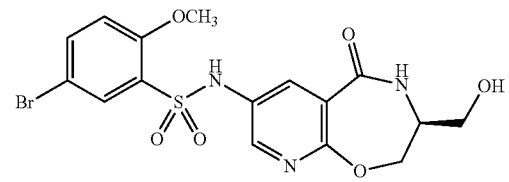 [SMILES: COc1ccc(Cl)cc1S(=O)(=O)Nc1cnc2c(c1)C(=O)N[C@@H](CO)CO2]

(29a) N-[(3S)-3-[(Benzyloxy)methyl]-4-(2,4-dimethoxybenzyl)-5-oxo-2,3,4,5-tetrahydropyrido[3,2-f][1,4]oxazepin-7-yl]-5-bromo-2-methoxybenzenesulfonamide To a mixture of (3S)-7-amino-3-[(benzyloxy)methyl]-4-(2,4-dimethoxybenzyl)-3,4-dihydropyrido[3,2-f][1,4]oxazepin-5(2H)-one (200 mg, 0.45 mmol) obtained in Example (27d) and pyridine (0.72 mL, 8.9 mmol), 5-bromo-2-methoxybenzenesulfonyl chloride (140 mg, 0.49 mmol) was added, and the mixture was stirred at 80° C. for 2 hours in an oil bath. The reaction mixture was cooled and then concentrated under reduced pressure, and the residue was purified in an automatic chromatography apparatus (n-hexane/ethyl acetate=100/0-0/100) to obtain the title compound (318 mg, yield: quantitative).
$^1$H NMR spectrum (CDCl$_3$, 400 MHz) δ: 8.37 (1H, d, J=2.7 Hz), 8.30 (1H, d, J=2.7 Hz), 7.87 (1H, d, J=2.0 Hz), 7.60 (1H, dd, J=8.6, 2.3 Hz), 7.33-7.21 (5H, m), 6.95 (2H, d, J=8.6 Hz), 6.44 (2H, d, J=6.7 Hz), 5.04 (1H, d, J=14.5 Hz), 4.73 (1H, dd, J=12.9, 5.1 Hz), 4.49-4.39 (3H, m), 4.08-4.05 (4H, m), 3.99 (1H, dd, J=12.3, 6.6 Hz), 3.79 (3H, s), 3.77 (3H, s), 3.55 (1H, t, J=8.6 Hz), 3.44 (1H, dd, J=9.4, 6.6 Hz).

(29b) 5-Bromo-N-[(3S)-3-(hydroxymethyl)-5-oxo-2,3,4,5-tetrahydropyrido[3,2-f][1,4]oxazepin-7-yl]-2-methoxybenzenesulfonamide To a solution of N-[(3S)-3-[(benzyloxy)methyl]-4-(2,4-dimethoxybenzyl)-5-oxo-2,3,4,5-tetrahydropyrido[3,2-f][1,4]oxazepin-7-yl]-5-bromo-2-methoxybenzenesulfonamide (318 mg, 0.46 mmol) obtained in Example (29a) and anisole (0.15 mL, 1.4 mmol) in chloroform (2.5 mL), trifluoroacetic acid (0.7 mL, 9.1 mmol) and trifluoromethanesulfonic acid (0.12 mL, 1.4 mmol) were added, and the mixture was stirred at room temperature for 2 hours. The reaction mixture was diluted by addition of water (5 mL) and tetrahydrofuran (2.5 mL) and stirred at room temperature for 1 hour. To the reaction mixture, sodium bicarbonate (0.92 g, 10.9 mmol) was carefully added, and the mixture was stirred at room temperature for 10 minutes. To the mixture, a 2 N aqueous sodium hydroxide solution (0.5 mL, 1.0 mmol) was added, and the mixture was washed with ethyl acetate. To the aqueous layer, 2 N hydrochloric acid (0.75 mL, 1.5 mmol) was added, followed by extraction with a mixed solvent of chloroform/isopropanol=3/1. The organic layer was dried over anhydrous sodium sulfate. After filtration, the solvent was distilled off under reduced pressure. To the residue, ethyl acetate was added, and the precipitated solid was collected by filtration, washed with ethyl acetate, and then dried to obtain the title compound (147 mg, yield: 71%).
$^1$H NMR spectrum (DMSO-d6, 400 MHz) δ: 10.29 (1H, s), 8.36 (1H, d, J=3.9 Hz), 8.23 (1H, d, J=2.7 Hz), 8.06 (1H, d, J=2.7 Hz), 7.80-7.76 (1H, m), 7.75 (1H, d, J=2.7 Hz), 7.19 (1H, d, J=9.4 Hz), 5.05 (1H, t, J=5.3 Hz), 4.37-4.35 (2H, m), 3.86 (3H, s), 3.50-3.38 (3H, m).
MS spectrum (ES/APCI$^+$): 458 (M+H), 460 (M+2+H).

(Example 30) N-[(3S)-3-(Hydroxymethyl)-5-oxo-2,3,4,5-tetrahydropyrido[3,2-f][1,4]oxazepin-7-yl]-2,5-dimethoxybenzenesulfonamide (30a) N-[(3S)-3-[(Benzyloxy)methyl]-4-(2,4-dimethoxybenzyl)-5-oxo-2,3,4,5-tetrahydropyrido[3,2-f][1,4]oxazepin-7-yl]-2,5-dimethoxybenzenesulfonamide To a mixture of (3S)-7-amino-3-[(benzyloxy)methyl]-4-(2,4-dimethoxybenzyl)-3,4-dihydropyrido[3,2-f][1,4]oxazepin-5(2H)-one (180 mg, 0.40 mmol) obtained in Example (27d) and pyridine (0.65 mL, 8.0 mmol), 2,5-dimethoxybenzenesulfonyl chloride (104 mg, 0.44 mmol) was added, and the mixture was stirred at 80° C. for 2 hours in an oil bath. The reaction mixture was cooled and then concentrated under reduced pressure, and the residue was purified in an automatic chromatography apparatus (n-hexane/ethyl acetate=100/0-0/100) to obtain the title compound (266 mg, yield: quantitative).
$^1$H NMR spectrum (CDCl$_3$, 400 MHz) δ: 8.42 (1H, d, J=2.7 Hz), 8.30 (1H, d, J=2.7 Hz), 7.33-7.21 (8H, m), 7.03 (1H, dd, J=9.0, 3.1 Hz), 6.98 (1H, d, J=9.0 Hz), 6.45-6.41 (2H, m), 5.03 (1H, d, J=14.5 Hz), 4.71 (1H, dd, J=12.7, 5.3 Hz), 4.47-4.38 (3H, m), 4.06-3.95 (5H, m), 3.79 (3H, s), 3.77 (3H, s), 3.73 (3H, s), 3.55 (1H, dd, J=9.6, 7.6 Hz), 3.42 (1H, dd, J=9.6, 6.5 Hz).

(30b) N-[(3S)-3-(Hydroxymethyl)-5-oxo-2,3,4,5-tetrahydropyrido[3,2-f][1,4]oxazepin-7-yl]-2,5-dimethoxybenzenesulfonamide To a solution of N-[(3S)-3-[(benzyloxy)methyl]-4-(2,4-dimethoxybenzyl)-5-oxo-2,3,4,5-tetrahydropyrido[3,2-f][1,4]oxazepin-7-yl]-2,5-dimethoxybenzenesulfonamide (266 mg, 0.41 mmol) obtained in Example (30a) and anisole (0.13 mL, 1.2 mmol) in chloroform (2.5 mL), trifluoroacetic acid (0.63 mL, 8.2 mmol) and trifluoromethanesulfonic acid (0.11 mL, 1.2 mmol) were added, and the mixture was stirred at room temperature for 2 hours. The reaction mixture was diluted by addition of water (5 mL) and tetrahydrofuran (2.5 mL) and stirred at room temperature for 1 hour. To the reaction mixture, sodium bicarbonate (0.83 g, 9.8 mmol) was carefully added, and the mixture was stirred at room temperature for 10 minutes. To the reaction mixture, a 2 N aqueous sodium hydroxide solution (0.5 mL, 1.0 mmol) was added, and the mixture was washed with ethyl acetate. To the aqueous layer, 2 N hydrochloric acid (0.75 mL, 1.5 mmol) was added, followed by extraction with a mixed solvent of chloroform/isopropanol=3/1. The organic layer was dried over anhydrous sodium sulfate. After filtration, the solvent was distilled off under reduced pressure. To the residue, ethyl acetate was added, and the precipitated solid was collected by filtration, washed with ethyl acetate, and then dried to obtain the title compound (74 mg, yield: 44%).
$^1$H NMR spectrum (DMSO-d6, 400 MHz) δ: 10.17 (1H, br s), 8.35 (1H, d, J=3.9 Hz), 8.25 (1H, d, J=2.7 Hz), 8.07 (1H, d, J=2.7 Hz), 7.21 (1H, d, J=2.7 Hz), 7.19-7.13 (2H, m), 4.36-4.32 (2H, m), 3.81 (3H, s), 3.72 (3H, s), 3.49-3.35 (3H, m).
MS spectrum (ES/APCI$^+$): 410 (M+H).

(Example 31) 5-Chloro-N-[(3S)-3-(hydroxymethyl)-5-oxo-2,3,4,5-tetrahydropyrido[3,2-f][1,4]oxazepin-7-yl]-2-(trifluoromethoxy)benzenesulfonamide

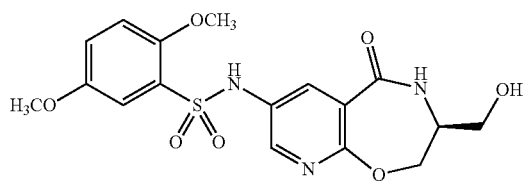 [SMILES: COc1ccc(OC)c(S(=O)(=O)Nc2cnc3c(c2)C(=O)N[C@@H](CO)CO3)c1]

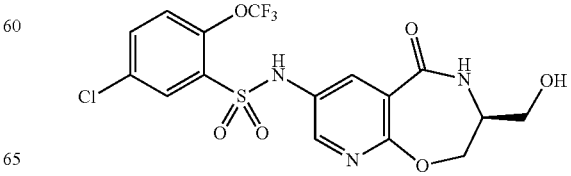

(31a) N-[(3S)-3-[(Benzyloxy)methyl]-4-(2,4-dimethoxybenzyl)-5-oxo-2,3,4,5-tetrahydropyrido[3,2-f][1,4]oxazepin-7-yl]-5-chloro-2-(trifluoromethoxy)benzenesulfonamide To a mixture of (3S)-7-amino-3-[(benzyloxy)methyl]-4-(2,4-dimethoxybenzyl)-3,4-dihydropyrido[3,2-f][1,4]oxazepin-5(2H)-one (220 mg, 0.49 mmol) obtained in Example (27d) and pyridine (0.79 mL, 9.8 mmol), 5-chloro-2-(trifluoromethoxy)benzenesulfonyl chloride (approximately 83% content, 159 mg, 0.54 mmol) obtained in Example (13a) was added, and the mixture was stirred at 80° C. for 1 hour in an oil bath. The reaction mixture was cooled and then diluted by addition of water, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-65/35) to obtain the title compound (239 mg, yield: 69%).

$^1$H NMR spectrum (CDCl$_3$, 400 MHz) δ: 8.45 (1H, d, J=2.7 Hz), 8.28 (1H, d, J=2.7 Hz), 7.88 (1H, d, J=2.7 Hz), 7.56 (1H, dd, J=8.8, 2.5 Hz), 7.39-7.21 (7H, m), 6.99 (1H, br s), 6.46-6.42 (2H, m), 5.05 (1H, d, J=14.5 Hz), 4.75 (1H, dd, J=12.9, 5.1 Hz), 4.50-4.39 (3H, m), 4.10-4.00 (2H, m), 3.79 (3H, s), 3.78 (3H, s), 3.55 (1H, dd, J=9.6, 7.6 Hz), 3.44 (1H, dd, J=9.6, 6.5 Hz).

(31b) 5-Chloro-N-[(3S)-3-(hydroxymethyl)-5-oxo-2,3,4,5-tetrahydropyrido[3,2-f][1,4]oxazepin-7-yl]-2-(trifluoromethoxy)benzenesulfonamide To a solution of N-[(3S)-3-[(benzyloxy)methyl]-4-(2,4-dimethoxybenzyl)-5-oxo-2,3,4,5-tetrahydropyrido[3,2-f][1,4]oxazepin-7-yl]-5-chloro-2-(trifluoromethoxy)benzenesulfonamide (234 mg, 0.33 mmol) obtained in Example (31a) and anisole (0.11 mL, 1.0 mmol) in chloroform (1.6 mL), trifluoroacetic acid (0.51 mL, 6.6 mmol) and trifluoromethanesulfonic acid (0.09 mL, 1.0 mmol) were added, and the mixture was stirred at room temperature for 1 hour. The reaction mixture was diluted by addition of water (3.2 mL) and tetrahydrofuran (1.6 mL) and stirred at room temperature for 1 hour. To the reaction mixture, sodium bicarbonate (0.67 g, 7.9 mmol) was carefully added, and the mixture was stirred at room temperature for 10 minutes. The reaction mixture was concentrated under reduced pressure. To the concentrated mixture, a 2 N aqueous sodium hydroxide solution (0.33 mL, 0.66 mmol) was added, and the mixture was washed with ethyl acetate. To the aqueous layer, 1 N hydrochloric acid (0.66 mL, 0.66 mmol) was added, followed by extraction with a mixed solvent of methylene chloride/isopropanol=4/1. The organic layer was dried over anhydrous sodium sulfate. After filtration, the solvent was distilled off under reduced pressure. To the residue, ethyl acetate was added, and the precipitated solid was collected by filtration, washed with ethyl acetate, and then dried to obtain the title compound (101 mg, yield: 65%).

$^1$H NMR spectrum (DMSO-d6, 400 MHz) δ: 10.77 (1H, br s), 8.41 (1H, br d, J=4.3 Hz), 8.21 (1H, d, J=2.7 Hz), 8.11 (1H, d, J=2.7 Hz), 7.91 (1H, d, J=2.7 Hz), 7.87 (1H, dd, J=8.8, 2.7 Hz), 7.64-7.60 (1H, m), 5.07 (1H, t, J=5.5 Hz), 4.43-4.34 (2H, m), 3.52-3.37 (3H, m).

MS spectrum (ESI$^+$): 468 (M+H), 470 (M+2+H).

(Example 32) 5-Fluoro-N-[(3S)-3-(hydroxymethyl)-5-oxo-2,3,4,5-tetrahydropyrido[3,2-f][1,4]oxazepin-7-yl]-2-(trifluoromethoxy)benzenesulfonamide

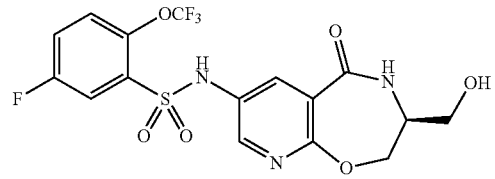 [SMILES: O=C1N[C@@H](CO)COc2ncc(NS(=O)(=O)c3cc(F)ccc3OC(F)(F)F)cc21]

(32a) 5-Fluoro-2-(trifluoromethoxy)benzenesulfonyl chloride

The title compound (approximately 50% content, 2.49 g, yield: 81%) was obtained as a mixture containing positional isomers by production according to the method described in Example (13a) using 4-fluorophenyl trifluoromethyl ether (2.00 g, 11.1 mmol).

$^1$H NMR spectrum (CDCl$_3$, 400 MHz) δ: 7.87-7.82 (1H, m), 7.65-7.60 (0 5H, m), 7.57-7.47 (1H, m), 7.42 (0 5H, t, J=9.0 Hz).

(32b) N-[(3S)-3-[(Benzyloxy)methyl]-4-(2,4-dimethoxybenzyl)-5-oxo-2,3,4,5-tetrahydropyrido[3,2-f][1,4]oxazepin-7-yl]-5-fluoro-2-(trifluoromethoxy)benzenesulfonamide To a mixture of (3S)-7-amino-3-[(benzyloxy)methyl]-4-(2,4-dimethoxybenzyl)-3,4-dihydropyrido[3,2-f][1,4]oxazepin-5(2H)-one (410 mg, 0.91 mmol) obtained in Example (27d) and pyridine (1.48 mL, 18.2 mmol), 5-fluoro-2-(trifluoromethoxy)benzenesulfonyl chloride (approximately 50% content, 280 mg, 1.00 mmol) obtained in Example (32a) was added, and the mixture was stirred at 80° C. for 1 hour in an oil bath. The reaction mixture was cooled and then diluted by addition of water, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-65/35) to obtain the title compound (265 mg, yield: 42%).

$^1$H NMR spectrum (CDCl$_3$, 400 MHz) δ: 8.44 (1H, d, J=2.7 Hz), 8.27 (1H, d, J=2.7 Hz), 7.61 (1H, dd, J=7.4, 3.1 Hz), 7.45-7.40 (1H, m), 7.34-7.22 (7H, m), 7.01 (1H, br s), 6.46-6.42 (2H, m), 5.04 (1H, d, J=14.5 Hz), 4.74 (1H, dd, J=12.9, 5.1 Hz), 4.49-4.39 (3H, m), 4.10-3.99 (2H, m), 3.79 (3H, s), 3.78 (3H, s), 3.55 (1H, dd, J=9.6, 7.6 Hz), 3.43 (1H, dd, J=9.6, 6.3 Hz).

(32c) 5-Fluoro-N-[(3S)-3-(hydroxymethyl)-5-oxo-2,3,4,5-tetrahydropyrido[3,2-f][1,4]oxazepin-7-yl]-2-(trifluoromethoxy)benzenesulfonamide To a solution of N-[(3S)-3-[(benzyloxy)methyl]-4-(2,4-dimethoxybenzyl)-5-oxo-2,3,4,5-tetrahydropyrido[3,2-f][1,4]oxazepin-7-yl]-5-fluoro-2-(trifluoromethoxy)benzenesulfonamide (258 mg, 0.37 mmol) obtained in Example (32b) and anisole (0.12 mL, 1.1 mmol) in chloroform (1.8 mL), trifluoroacetic acid (0.57 mL, 7.5 mmol) and trifluoromethanesulfonic acid (0.10 mL, 1.1 mmol) were added, and the mixture was stirred at room temperature for 1 hour. The reaction mixture was diluted by addition of water (3.6 mL) and tetrahydrofuran (1.8 mL) and stirred at room temperature for 1 hour. To the reaction mixture, sodium bicarbonate (0.75 g, 9.0 mmol) was carefully added, and the mixture was stirred at room temperature for 10 minutes. The reaction mixture was concentrated under reduced pressure. To the concentrated mixture, a 2 N aqueous sodium hydroxide solution (0.37 mL, 0.74 mmol) was added, followed by extraction with ethyl acetate. To the aqueous layer, 1 N hydrochloric acid (0.75 mL, 0.75 mmol) was added, followed by extraction with a mixed solvent of methylene chloride/isopropanol=4/1. The organic layer was dried over anhydrous sodium sulfate. After filtration, the solvent was distilled off under reduced pressure. To the residue, ethyl acetate was added, and the precipitated solid was collected by filtration, washed with ethyl acetate, and then dried to obtain the title compound (135 mg, yield: 80%).

$^1$H NMR spectrum (DMSO-d6, 400 MHz) δ: 10.77 (1H, br s), 8.40 (1H, br d, J=4.3 Hz), 8.21 (1H, d, J=2.7 Hz), 8.11 (1H, d, J=2.7 Hz), 7.76-7.72 (1H, m), 7.69-7.63 (2H, m), 5.07 (1H, t, J=5.3 Hz), 4.44-4.34 (2H, m), 3.54-3.37 (3H, m).

MS spectrum (ESI$^+$): 452 (M+H).

(Example 33) 5-Chloro-N-[(3S)-3-(2-hydroxyethyl)-5-oxo-2,3,4,5-tetrahydropyrido[3,2-f][1,4]oxazepin-7-yl]-2-methoxybenzenesulfonamide

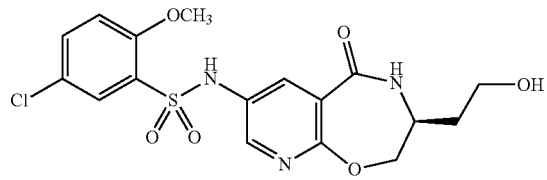 [SMILES: COc1ccc(Cl)cc1S(=O)(=O)Nc1cnc2c(c1)C(=O)N[C@@H](CCO)CO2]

(33a) (6S)—N-(2,4-Dimethoxybenzyl)-2,2,11,11-tetramethyl-3,3,10,10-tetraphenyl-4,9-dioxa-3,10-disiladodecan-6-amine To a solution of tert-butyl [(2S)-1,4-dihydroxybutan-2-yl]carbamate (2.00 g, 9.74 mmol) in methylene chloride (50 mL), imidazole (1.99 g, 11.5 mmol) and tert-butyl(chloro)diphenylsilane (5.89 g, 21.4 mmol) were added, and the mixture was stirred at room temperature for 2 hours. The reaction mixture was diluted by addition of water, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-90/10) to obtain tert-butyl [(6S)-2,2,11,11-tetramethyl-3,3,10,10-tetraphenyl-4,9-dioxa-3,10-disiladodecan-6-yl]carbamate. To tert-butyl [(6S)-2,2,11,11-tetramethyl-3,3,10,10-tetraphenyl-4,9-dioxa-3,10-disiladodecan-6-yl]carbamate thus obtained, trifluoroacetic acid (50 mL, 653 mmol) was added, and the mixture was stirred at room temperature for 1 hour. The reaction mixture was concentrated under reduced pressure, and the residue was neutralized by the addition of saturated sodium bicarbonate, followed by extraction with ethyl acetate. The organic layer was washed with a saturated aqueous solution of sodium chloride and dried over anhydrous sodium sulfate. After filtration, the solvent was distilled off under reduced pressure to obtain a crude product of (6S)-2,2,11,11-tetramethyl-3,3,10,10-tetraphenyl-4,9-dioxa-3,10-disiladodecan-6-amine. To a solution of the crude product of (6S)-2,2,11,11-tetramethyl-3,3,10,10-tetraphenyl-4,9-dioxa-3,10-disiladodecan-6-amine thus obtained in methanol (9.35 mL), 2,4-dimethoxybenzaldehyde (2.11 g, 12.7 mmol) and triethylamine (9.56 mL, 69.2 mmol) were added, and the mixture was stirred at room temperature for 1 hour. Subsequently, to the reaction mixture, anhydrous sodium sulfate (0.901 g, 6.34 mmol) was added, and the mixture was stirred at room temperature for 18 hours. Subsequently, to the reaction mixture, sodium borohydride (0.24 g, 6.34 mmol) was added under ice cooling, and the reaction mixture was stirred at the same temperature as above for 1 hour. The reaction mixture was diluted by addition of a saturated aqueous solution of sodium bicarbonate, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-40/60) to obtain the title compound (8.08 g, yield for 3 steps: quantitative).

$^1$H NMR spectrum (CDCl$_3$, 400 MHz) δ: 7.70-7.59 (8H, m), 7.45-7.30 (12H, m), 7.04 (1H, d, J=8.2 Hz), 6.51-6.35 (2H, m), 3.82 (3H, s), 3.81 (3H, s), 3.74-3.51 (6H, m), 2.90-2.75 (1H, m), 1.77-1.56 (2H, m).

(33b) (3S)-4-(2,4-Dimethoxybenzyl)-3-(2-hydroxyethyl)-7-nitro-3,4-dihydropyrido[3,2-f][1,4]oxazepin-5(2H)-one To a suspension of 2-chloro-5-nitropyridine-3-carboxylic acid (2.24 g, 11.04 mmol) in methylene chloride (110 mL), oxalyl chloride (1.42 mL, 16.6 mmol) and N,N-dimethylformamide (1.42 mL, 5.52 mmol) were added at room temperature, and the mixture was stirred at the same temperature as above for 2 hours. The reaction mixture was concentrated under reduced pressure to prepare a crude product of 2-chloro-5-nitropyridine-3-carboxylic acid chloride. Subsequently, to a solution of (6S)—N-(2,4-dimethoxybenzyl)-2,2,11,11-tetramethyl-3,3,10,10-tetraphenyl-4,9-dioxa-3,10-disiladodecan-6-amine (8.08 g, 11.04 mmol) obtained in Example (33a) and N,N-diisopropylethylamine (3.85 mL, 22.1 mmol) in tetrahydrofuran (110 mL), a solution of the crude product of 2-chloro-5-nitropyridine-3-carboxylic acid chloride in tetrahydrofuran (20 mL) was added under ice cooling, and the mixture was stirred at room temperature for 2 hours. The reaction mixture was diluted by addition of water, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-80/20) to obtain 2-chloro-N-(2,4-dimethoxybenzyl)-5-nitro-N-[(6S)-2,2,11,11-tetramethyl-3,3,10,10-tetraphenyl-4,9-dioxa-3,10-disiladodecan-6-yl]pyridine-3-carboxamide (7.193 g, yield: 71%). To a solution of 2-chloro-N-(2,4-dimethoxybenzyl)-5-nitro-N-[(6S)-2,2,11,11-tetramethyl-3,3,10,10-tetraphenyl-4,9-dioxa-3,10-disiladodecan-6-yl]pyridine-3-carboxamide (1.09 g, 1.19 mmol) thus obtained in tetrahydrofuran (15 mL), a solution of tetrabutylammonium fluoride in tetrahydrofuran (1 mol/L, 3.57 mL, 3.57 mmol) was added under ice cooling, and the mixture was stirred at room temperature for 24 hours. The reaction mixture was diluted by addition of a saturated aqueous solution of ammonium chloride, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-0/100) to obtain the title compound (233 mg, yield: 49%).

$^1$H NMR spectrum (CDCl$_3$, 400 MHz) δ: 9.58 (1H, d, J=2.5 Hz), 9.19 (1H, d, J=2.5 Hz), 7.37 (1H, d, J=8.2 Hz), 6.52-6.47 (2H, m), 5.12 (1H, d, J=14.3 Hz), 4.76 (1H, dd, J=12.9, 5.5 Hz), 4.48 (1H, d, J=14.3 Hz), 4.31-4.22 (2H, m), 3.84 (3H, s), 3.81 (3H, s), 3.79-3.67 (2H, m), 1.89-1.79 (1H, m), 1.75-1.65 (1H, m).

(33c) (3S)-7-Amino-4-(2,4-dimethoxybenzyl)-3-(2-hydroxyethyl)-3,4-dihydropyrido[3,2-f][1,4]oxazepin-5(2H)-one The title compound (60.0 mg, yield: quantitative) was obtained by production according to the method described in Example (3c) using (3S)-4-(2,4-dimethoxybenzyl)-3-(2-hydroxyethyl)-7-nitro-3,4-dihydropyrido[3,2-f][1,4]oxazepin-5(2H)-one (64.0 mg, 0.16 mmol) obtained in Example (33b).

$^1$H NMR spectrum (CDCl$_3$, 400 MHz) δ: 8.09 (1H, d, J=2.7 Hz), 7.86 (1H, d, J=2.7 Hz), 7.33-7.31 (1H, m), 6.48-6.46 (2H, m), 5.10 (1H, d, J=14.5 Hz), 4.54 (1H, dd, J=12.9, 5.5 Hz), 4.45 (1H, d, J=14.5 Hz), 4.08 (1H, d, J=12.9 Hz), 4.05-3.97 (1H, m), 3.82 (3H, s), 3.80 (3H, s), 3.76-3.49 (5H, m), 1.90-1.70 (2H, m).

(33d) 5-Chloro-N-[(3S)-4-(2,4-dimethoxybenzyl)-3-(2-hydroxyethyl)-5-oxo-2,3,4,5-tetrahydropyrido[3,2-f][1,4]oxazepin-7-yl]-2-methoxybenzenesulfonamide The title compound (67 mg, yield: 72%) was obtained by production according to Example (1d) using (3S)-7-amino-4-(2,4-dimethoxybenzyl)-3-(2-hydroxyethyl)-3,4-dihydropyrido[3,2-f][1,4]oxazepin-5(2H)-one (60.0 mg, 0.16 mmol) obtained in Example (33c) and 5-chloro-2-methoxybenzenesulfonyl chloride (42.6 mg, 0.18 mmol).

$^1$H NMR spectrum (CDCl3, 400 MHz) δ: 8.40 (1H, d, J=2.7 Hz), 8.30 (1H, d, J=2.7 Hz), 7.74 (1H, dd, J=3.7, 2.5 Hz), 7.49-7.43 (1H, m), 7.34-7.24 (1H, m), 7.00 (1H, dd, J=9.0, 3.9 Hz), 6.48-6.43 (2H, m), 5.08 (1H, dd, J=14.4, 3.6 Hz), 4.59 (1H, dt, J=12.7, 4.7 Hz), 4.41 (1H, dd, J=14.4, 3.6 Hz), 4.15-4.03 (8H, m), 3.80 (3H, s), 3.75-3.62 (2H, m), 1.85-1.58 (2H, m).

(33e) 5-Chloro-N-[(3S)-3-(2-hydroxyethyl)-5-oxo-2,3,4,5-tetrahydropyrido[3,2-f][1,4]oxazepin-7-yl]-2-methoxybenzenesulfonamide The title compound (42 mg, yield: 85%) was obtained by production according to the method described in Example (9) using 5-chloro-N-[(3S)-4-(2,4-dimethoxybenzyl)-3-(2-hydroxyethyl)-5-oxo-2,3,4,5-tetrahydropyrido[3,2-f][1,4]oxazepin-7-yl]-2-methoxybenzenesulfonamide (67 mg, 0.12 mmol) obtained in Example (33d).

$^1$H NMR spectrum (DMSO-d6, 400 MHz) δ: 10.29 (1H, br s), 8.48 (1H, d, J=5.9 Hz), 8.14 (1H, d, J=2.7 Hz), 8.08 (1H, d, J=2.7 Hz), 7.68 (1H, d, J=2.4 Hz), 7.65 (1H, dd, J=5.9, 2.4 Hz), 7.25 (1H, d, J=8.8 Hz), 4.32-4.29 (2H, m), 3.87 (3H, s), 3.63-3.40 (3H, m), 1.60-1.55 (2H, m).

MS spectrum (ES/APCI$^+$): 428 (M+H), 430 (M+2+H).

(Example 34) 2-[(3S)-7-{[(5-Chloro-2-methoxyphenyl)sulfonyl]amino}-5-oxo-2,3,4,5-tetrahydropyrido[3,2-f][1,4]oxazepin-3-yl]-N,N-dimethylacetamide

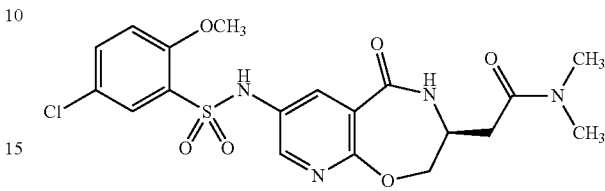

(34a) 2-[(3S)-4-(2,4-Dimethoxybenzyl)-7-nitro-5-oxo-2,3,4,5-tetrahydropyrido[3,2-f][1,4]oxazepin-3-yl]-N,N-dimethylacetamide To a mixture of (3S)-4-(2,4-dimethoxybenzyl)-3-(2-hydroxyethyl)-7-nitro-3,4-dihydropyrido[3,2-f][1,4]oxazepin-5(2H)-one (120 mg, 0.30 mmol) obtained in Example (33b) in acetonitrile (3 mL) and a phosphate buffer solution (pH 6.86) (2 mL), 2-azaadamantane-N-oxyl (45.3 mg, 0.030 mmol) and sodium chlorate (32.3 mg, 0.036 mmol) were added, subsequently an aqueous sodium hypochlorite solution (available chlorine concentration: >5%, 2.35 mL, 0.9 mmol) was added under ice cooling, and the mixture was stirred for 3 hours under ice cooling. The reaction mixture was diluted by addition of a saturated aqueous solution of sodium thiosulfate and a saturated aqueous solution of ammonium chloride, followed by extraction with ethyl acetate. The organic layer was washed with a saturated aqueous solution of sodium chloride and dried over anhydrous sodium sulfate. After filtration, the solvent was distilled off under reduced pressure to obtain a crude product of [(3S)-4-(2,4-dimethoxybenzyl)-7-nitro-5-oxo-2,3,4,5-tetrahydropyrido[3,2-f][1,4]oxazepin-3-yl]acetic acid. To a solution of the crude product of [(3S)-4-(2,4-dimethoxybenzyl)-7-nitro-5-oxo-2,3,4,5-tetrahydropyrido[3,2-f][1,4]oxazepin-3-yl]acetic acid thus obtained in N,N-dimethylformamide (10 mL), dimethylamine hydrochloride (36.3 mg, 0.45 mmol), 1-ethyl-3-(3-dimethylaminopropyl)carbodiimide hydrochloride (114 mg, 0.59 mmol), 1-hydroxybenzotriazole monohydrate (91.0 mg, 0.59 mmol), and triethylamine (0.206 mL, 1.49 mmol) were added, and the mixture was stirred at room temperature for 17 hours. The reaction mixture was diluted by addition of water, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-85/15) to obtain the title compound (108 mg, yield for 2 steps: 82%).

$^1$H NMR spectrum (CDCl$_3$, 400 MHz) δ: 9.62 (1H, d, J=2.7 Hz), 9.21 (1H, dd, J=4.9, 2.7 Hz), 7.44-7.36 (1H, m), 6.52-6.45 (2H, m), 5.00-4.90 (2H, m), 4.70-4.56 (2H, m), 4.28 (1H, d, J=12.5 Hz), 3.82 (3H, s), 3.80 (3H, s), 2.85 (3H, s), 2.82 (3H, s), 2.61 (1H, td, J=16.2, 9.4 Hz), 2.39 (1H, dq, J=16.2, 4.4 Hz).

(34b) 2-[(3S)-7-Amino-4-(2,4-dimethoxybenzyl)-5-oxo-2,3,4,5-tetrahydropyrido[3,2-f][1,4]oxazepin-3-yl]-N,N-dimethylacetamide The title compound (90.0 mg, yield: 89%) was obtained by production according to the method described in Example (3c) using 2-[(3S)-4-(2,4-dimethoxybenzyl)-7-nitro-5-oxo-2,3,4,5-tetrahydropyrido[3,2-f][1,4]oxazepin-3-yl]-N,N-dimethylacetamide (108 mg, 0.24 mmol) obtained in Example (34a).

$^1$H NMR spectrum (CDCl$_3$, 400 MHz) δ: 8.14 (1H, t, J=2.9 Hz), 7.90 (1H, t, J=3.5 Hz), 7.40-7.30 (1H, m), 6.50-6.43 (2H, m), 4.93 (1H, t, J=15.3 Hz), 4.70 (1H, dq, J=12.6, 2.5 Hz), 4.55 (1H, dd, J=14.5, 3.9 Hz), 4.52-4.45 (1H, m), 4.08 (1H, dd, J=12.6, 6.8 Hz), 3.91 (3H, s), 3.79 (3H, s), 2.92 (3H, s), 2.85 (3H, s), 2.76-2.64 (1H, m), 2.37 (1H, td, J=10.6, 5.5 Hz).

(34c) 2-[(3S)-7-{[(5-Chloro-2-methoxyphenyl)sulfonyl]amino}-4-(2,4-dimethoxybenzyl)-5-oxo-2,3,4,5-tetrahydropyrido[3,2-f][1,4]oxazepin-3-yl]-N,N-dimethylacetamide The title compound (40 mg, yield: 30%) was obtained by production according to Example (1d) using 2-[(3S)-7-amino-4-(2,4-dimethoxybenzyl)-5-oxo-2,3,4,5-tetrahydropyrido[3,2-f][1,4]oxazepin-3-yl]-N,N-dimethylacetamide (90.0 mg, 0.22 mmol) obtained in Example (34b) and 5-chloro-2-methoxybenzenesulfonyl chloride (57.6 mg, 0.24 mmol).

$^1$H NMR spectrum (CDCl3, 400 MHz) δ: 8.43 (1H, d, J=2.7 Hz), 8.30 (1H, d, J=2.7 Hz), 7.73 (1H, d, J=2.4 Hz), 7.46 (1H, dd, J=8.9, 2.7 Hz), 7.32-7.24 (1H, m), 7.01 (1H, dd, J=8.9, 2.4 Hz), 6.49-6.42 (2H, m), 4.91 (1H, d, J=14.1 Hz), 4.75 (1H, dd, J=12.7, 5.3 Hz), 4.56-4.46 (2H, m), 4.06 (3H, s), 3.91-3.83 (1H, m), 3.78 (3H, s), 3.78 (3H, s), 2.91 (3H, s), 2.79 (3H, s), 2.58 (1H, dd, J=16.0, 9.4 Hz), 2.31 (1H, dd, J=16.0, 4.7 Hz).

(34d) 2-[(3S)-7-{[(5-Chloro-2-methoxyphenyl)sulfonyl]amino}-5-oxo-2,3,4,5-tetrahydropyrido[3,2-f][1,4]oxazepin-3-yl]-N,N-dimethylacetamide The title compound (12 mg, yield: 40%) was obtained by production according to the method described in Example (9) using 2-[(3S)-7-{[(5-chloro-2-methoxyphenyl)sulfonyl]amino}-4-(2,4-dimethoxybenzyl)-5-oxo-2,3,4,5-tetrahydropyrido[3,2-f][1,4]oxazepin-3-yl]-N,N-dimethylacetamide (40.0 mg, 0.065 mmol) obtained in Example (34c).

$^1$H NMR spectrum (DMSO-d6, 400 MHz) δ: 10.32 (1H, br s), 8.19 (1H, d, J=2.7 Hz), 8.09 (1H, d, J=2.7 Hz), 7.68-7.65 (2H, m), 7.25 (1H, d, J=8.6 Hz), 4.40-4.28 (2H, m), 3.92-3.83 (4H, m), 3.80-3.74 (1H, m), 2.88 (3H, s), 2.82 (3H, s), 2.79-2.64 (2H, m).

MS spectrum (ES/APCI$^+$): 469 (M+H), 471 (M+2+H).

(Example 35) 5-Chloro-2-methoxy-N-(5'-oxo-4',5'-dihydrospiro[cyclopropane-1,3'-pyrido[3,2-f][1,4]oxazepin]-7'-yl)benzenesulfonamide

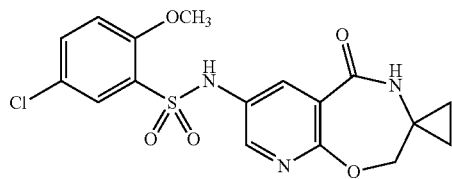 [SMILES: COc1ccc(Cl)cc1S(=O)(=O)Nc1cnc2c(c1)C(=O)NC1(CC1)CO2]

(35a) {1-[(2,4-Dimethoxybenzyl)amino]cyclopropyl}methanol

The title compound (1.90 g, yield: 91%) was obtained by production according to the method described in Example (8a) using (1-aminocyclopropyl)methanol (0.75 g, 0.24 mmol).

$^1$H NMR spectrum (CDCl$_3$, 400 MHz) δ: 7.14 (1H, d, J=8.2 Hz), 6.46-6.42 (2H, m), 3.83 (3H, s), 3.79 (3H, s), 3.74 (2H, s), 3.51 (2H, s), 3.48 (1H, s), 0.70-0.68 (2H, m), 0.52-0.49 (2H, m).

(35b) 2-Chloro-N-(2,4-dimethoxybenzyl)-N-[1-(hydroxymethyl)cyclopropyl]-5-nitropyridine-3-carboxamide To a suspension of 2-chloro-5-nitropyridine-3-carboxylic acid (1.587 g, 7.83 mmol) in methylene chloride (80 mL), oxalyl chloride (0.84 mL, 9.8 mmol) and N,N-dimethylformamide (0.30 mL, 3.92 mmol) were added at room temperature, and the mixture was stirred at the same temperature as above for 2 hours. The reaction mixture was concentrated under reduced pressure to prepare a crude product of 2-chloro-5-nitropyridine-3-carboxylic acid chloride. To a solution of {1-[(2,4-dimethoxybenzyl)amino]cyclopropyl}methanol (1.859 g, 7.83 mmol) obtained in Example (35a) and N,N-diisopropylethylamine (2.73 mL, 15.7 mmol) in tetrahydrofuran (60 mL), a solution of the crude product of 2-chloro-5-nitropyridine-3-carboxylic acid chloride in tetrahydrofuran (20 mL) was added under ice cooling, and the reaction mixture was stirred at room temperature for 30 minutes. The reaction mixture was diluted by addition of water, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-40/60) to obtain the title compound (2.155 g, yield: 65%).

$^1$H NMR spectrum (CDCl$_3$, 400 MHz) δ: 9.25 (0.14H, d, J=2.7 Hz), 9.19 (0.86H, d, J=2.7 Hz), 8.47 (0.14H, d, J=2.7 Hz), 7.06 (1H, br d, J=8.2 Hz), 6.43-6.36 (2H, m), 4.04-3.03 (11H, m), 1.28-1.23 (4H, m).

(35c) 4'-(2,4-Dimethoxybenzyl)-7'-nitrospiro[cyclopropane-1,3'-pyrido[3,2-f][1,4]oxazepin]-5' (4'H)-one To a solution of 2-chloro-N-(2,4-dimethoxybenzyl)-N-[1-(hydroxymethyl)cyclopropyl]-5-nitropyridine-3-carboxamide (400 mg, 0.95 mmol) obtained in Example (35b) in N,N-dimethylformamide (47 mL), potassium carbonate (393 mg, 2.84 mmol) was added, and the mixture was stirred at room temperature for 22 hours and subsequently stirred at 50° C. for 2 hours and at 70° C. for 2 hours. The reaction mixture was cooled, and insoluble matter was filtered off. The residue was washed with ethyl acetate. The filtrate and the washes were combined. The solvent was distilled off under reduced pressure, and the residue was purified in an automatic chromatography apparatus (n-hexane/ethyl acetate=100/0-50/50) to obtain the title compound (238 mg, yield: 65%).

$^1$H NMR spectrum (CDCl$_3$, 400 MHz) δ: 9.23-9.19 (1H, m), 9.11-9.08 (1H, m), 7.22 (1H, d, J=7.8 Hz), 6.49-6.45 (2H, m), 4.27-4.08 (3H, m), 3.92-3.74 (7H, m), 1.32-1.20 (2H, m), 0.97-0.87 (2H, m).

(35d) 7'-Amino-4'-(2,4-dimethoxybenzyl)spiro[cyclopropane-1,3'-pyrido[3,2-f][1,4]oxazepin]-5'(4'H)-one A mixture of 4'-(2,4-dimethoxybenzyl)-7'-nitrospiro[cyclopropane-1,3'-pyrido[3,2-f][1,4]oxazepin]-5'(4'H)-one (238 mg, 0.62 mmol) obtained in Example (35c) and 10% palladium carbon (water content: 54.6%, 100 mg) in tetrahydrofuran (30 mL), and methanol (30 mL) was stirred at room temperature for 3 hours at normal pressure under the hydrogen atmosphere. Hydrogen in the reaction container was replaced with nitrogen, and then, the reaction mixture was filtered through pad of Celite 545(R). The solvent in the filtrate was distilled off under reduced pressure to obtain the title compound (227 mg, yield: quantitative).

$^1$H NMR spectrum (CDCl$_3$, 400 MHz) δ: 7.84 (1H, d, J=2.2 Hz), 7.48 (1H, d, J=2.2 Hz), 7.20 (1H, d, J=8.2 Hz), 6.48-6.43 (2H, m), 4.70 (2H, br s), 3.82 (3H, s), 3.81 (3H, s), 3.69 (2H, s), 3.48 (2H, d, J=3.1 Hz), 0.93 (2H, br s), 0.63 (2H, br s).

(35e) 5-Chloro-2-methoxy-N-(5'-oxo-4',5'-dihydrospiro[cyclopropane-1,3'-pyrido[3,2-f][1,4]oxazepin]-7'-yl)benzenesulfonamide The title compound (80 mg, yield: 56%) was obtained by production according to the method described in Examples (1d) and (9) using 7'-amino-4'-(2,4-dimethoxybenzyl)spiro[cyclopropane-1,3'-pyrido[3,2-f][1,4]oxazepin]-5'(4'H)-one (124 mg, 0.35 mmol) obtained in Example (35d) and 5-chloro-2-methoxybenzenesulfonyl chloride (92.5 mg, 0.38 mmol).

$^1$H NMR spectrum (DMSO-d6, 400 MHz) δ: 10.29 (1H, br s), 8.84 (1H, s), 8.08 (1H, d, J=2.7 Hz), 7.94 (1H, d, J=2.7 Hz), 7.68-7.62 (2H, m), 7.25 (1H, d, J=8.6 Hz), 4.26 (2H, s), 3.87 (3H, s), 0.74 (4H, br s).

MS spectrum (ES/APCI$^+$): 410 (M+H), 412 (M+2+H).

(Example 36) 5-Fluoro-2-methoxy-N-(5'-oxo-4',5'-dihydrospiro[cyclopropane-1,3'-pyrido[3,2-f][1,4]oxazepin]-7'-yl)benzenesulfonamide

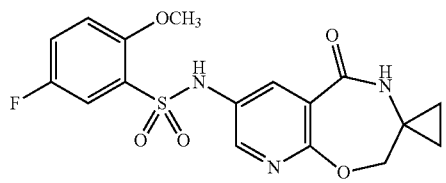

The title compound (81 mg, yield for 2 steps: 71%) was obtained by production according to the method described in Examples (1d) and (9) using 7'-amino-4'-(2,4-dimethoxybenzyl)spiro[cyclopropane-1,3'-pyrido[3,2-f][1,4]oxazepin]-5'(4'H)-one (103 mg, 0.29 mmol) obtained in Example (35d) and 5-fluoro-2-methoxybenzenesulfonyl chloride (71.6 mg, 0.32 mmol).

$^1$H NMR spectrum (DMSO-d6, 400 MHz) δ: 10.27 (1H, br s), 8.83 (1H, s), 8.08 (1H, d, J=3.1 Hz), 7.95 (1H, d, J=3.1 Hz), 7.51-7.46 (2H, m), 7.26-7.22 (1H, m), 4.25 (2H, s), 3.86 (3H, s), 0.74 (4H, br s).

MS spectrum (ES/APCI$^+$): 394 (M+H).

(Example 37) 5-Chloro-2-methoxy-N-(5-oxo-4-phenyl-2,3,4,5-tetrahydropyrido[3,2-f][1,4]oxazepin-7-yl)benzenesulfonamide

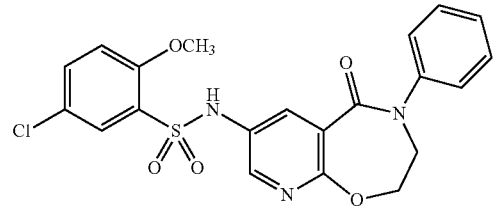 [SMILES: COc1ccc(Cl)cc1S(=O)(=O)Nc1cnc2c(c1)C(=O)N(c1ccccc1)CCO2]

(37a) 7-Nitro-4-phenyl-3,4-dihydropyrido[3,2-f][1,4]oxazepin-5(2H)-one

The title compound (324 mg, yield for 2 steps: 39%) was obtained by production according to the method described in Examples (1a) and (35c) using 2-chloro-5-nitropyridine-3-carboxylic acid (591 mg, 2.92 mmol) and 2-anilinoethanol (400 mg, 2.92 mmol).

$^1$H NMR spectrum (CDCl$_3$, 400 MHz) δ: 9.32 (1H, d, J=3.1 Hz), 9.28 (1H, d, J=3.1 Hz), 7.50-7.46 (2H, m), 7.39-7.35 (1H, m), 7.33-7.30 (2H, m), 4.87-4.85 (2H, m), 4.15-4.13 (2H, m).

(37b) 7-Amino-4-phenyl-3,4-dihydropyrido[3,2-f][1,4]oxazepin-5(2H)-one

The title compound (243 mg, yield: 84%) was obtained by production according to the method described in Example (3b) using 7-nitro-4-phenyl-3,4-dihydropyrido[3,2-f][1,4]oxazepin-5(2H)-one (324 mg, 1.14 mmol) obtained in Example (37a).

$^1$H NMR spectrum (CDCl$_3$, 400 MHz) δ: 7.93 (1H, d, J=3.1 Hz), 7.60 (1H, d, J=3.1 Hz), 7.46 (2H, t, J=7.6 Hz), 7.37-7.31 (3H, m), 4.58 (2H, t, J=5.1 Hz), 3.96 (2H, t, J=5.1 Hz), 3.69 (2H, br s).

(37c) 5-Chloro-2-methoxy-N-(5-oxo-4-phenyl-2,3,4,5-tetrahydropyrido[3,2-f][1,4]oxazepin-7-yl)benzenesulfonamide The title compound (77 mg, yield: 71%) was obtained by production according to Example (1d) using 7-amino-4-phenyl-3,4-dihydropyrido[3,2-f][1,4]oxazepin-5(2H)-one (60 mg, 0.24 mmol) obtained in Example (37b) and 5-chloro-2-methoxybenzenesulfonyl chloride (62 mg, 0.26 mmol).

$^1$H NMR spectrum (DMSO-d6, 400 MHz) δ: 10.39 (1H, br s), 8.16 (1H, d, J=2.4 Hz), 7.98 (1H, d, J=2.4 Hz), 7.69-7.67 (2H, m), 7.44 (2H, t, J=7.3 Hz), 7.36 (2H, d, J=7.3 Hz), 7.32-7.25 (2H, m), 4.56 (2H, t, J=4.6 Hz), 3.95 (2H, t, J=4.6 Hz), 3.88 (3H, s).

MS spectrum (ES/APCI$^+$): 460 (M+H), 462 (M+2+H).

(Example 38) 5-Chloro-2-methoxy-N-[5-oxo-4-(pyridin-2-yl)-2,3,4,5-tetrahydropyrido[3,2-f][1,4]oxazepin-7-yl]benzenesulfonamide

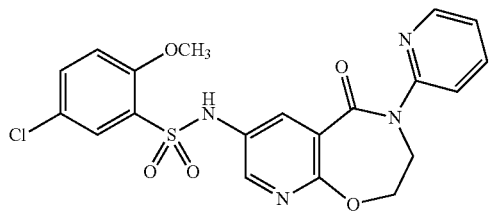 [SMILES: COc1ccc(Cl)cc1S(=O)(=O)Nc1cnc2c(c1)C(=O)N(c1ccccn1)CCO2]

(38a) 7-Nitro-3,4-dihydropyrido[3,2-f][1,4]oxazepin-5(2H)-one

The title compound (1.24 g, yield: quantitative) was obtained by production according to Example (18c) using 4-(2,4-dimethoxybenzyl)-7-nitro-3,4-dihydropyrido[3,2-f][1,4]oxazepin-5(2H)-one (2.00 g, 5.57 mmol) obtained in Example (8c).

$^1$H NMR spectrum (CD$_3$OD, 400 MHz) δ: 9.30 (1H, d, J=2.7 Hz), 9.19 (1H, d, J=2.7 Hz), 4.70-4.69 (2H, m), 3.67-3.65 (2H, m).

(38b) 7-Nitro-4-(pyridin-2-yl)-3,4-dihydropyrido[3,2-f][1,4]oxazepin-5(2H)-one

A mixture of 7-nitro-3,4-dihydropyrido[3,2-f][1,4]oxazepin-5(2H)-one (100 mg, 0.48 mmol) obtained in Example (38a), 2-bromopyridine (90.6 mg, 0.57 mmol), tris(dibenzylideneacetone)dipalladium(0) (87.6 mg, 0.010 mmol), 4,5-bis(diphenylphosphino)-9,9-dimethylxanthene (11.1 mg, 0.019 mmol), and cesium carbonate (0.312 g, 0.96 mmol) in dioxane (10 mL) was heated to reflux for 18 hours in an oil bath. The reaction mixture was cooled. The solvent was distilled off under reduced pressure, and the residue was purified in an automatic chromatography apparatus (n-hexane/ethyl acetate/methanol=100/0/0-0/100/0-0/85/15) to obtain the title compound (41 mg, yield: 30%).

$^1$H NMR spectrum (CDCl$_3$, 400 MHz) δ: 9.30 (1H, d, J=2.7 Hz), 9.25 (1H, d, J=2.7 Hz), 8.46-8.44 (1H, m), 8.06 (1H, d, J=8.2 Hz), 7.83-7.79 (1H, m), 7.22-7.19 (1H, m), 4.90 (2H, t, J=4.3 Hz), 4.57 (2H, t, J=4.3 Hz.

(38c) 5-Chloro-2-methoxy-N-[5-oxo-4-(pyridin-2-yl)-2,3,4,5-tetrahydropyrido[3,2-f][1,4]oxazepin-7-yl]benzenesulfonamide The title compound (58 mg, yield for 2 steps: 88%) was obtained by production according to Examples (3b) and (1d) using 7-nitro-4-(pyridin-2-yl)-3,4-dihydropyrido[3,2-f][1,4]oxazepin-5(2H)-one (41.0 mg, 0.14 mmol) obtained in Example (38b) and 5-chloro-2-methoxybenzenesulfonyl chloride (35.2 mg, 0.15 mmol).

$^1$H NMR spectrum (DMSO-d6, 400 MHz) δ: 10.45 (1H, br s), 8.47 (1H, d, J=3.9 Hz), 8.18 (1H, br s), 7.95-7.86 (3H, m), 7.70-7.67 (2H, m), 7.29-7.25 (2H, m), 4.53 (2H, br s), 4.30 (2H, br s), 3.88 (3H, s).

MS spectrum (ES/APCI$^+$): 461 (M+H), 463 (M+2+H).

(Example 39) 5-Chloro-2-methoxy-N-[5-oxo-4-(pyridin-3-yl)-2,3,4,5-tetrahydropyrido[3,2-f][1,4]oxazepin-7-yl]benzenesulfonamide

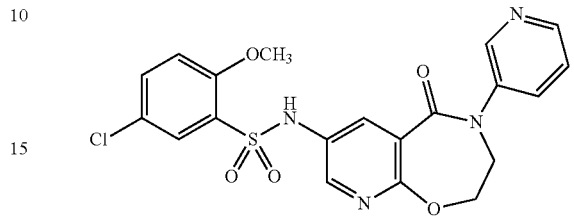

(39a) 7-Nitro-4-(pyridin-3-yl)-3,4-dihydropyrido[3,2-f][1,4]oxazepin-5(2H)-one

The title compound (104 mg, yield: 76%) was obtained by production according to the method described in Example (38b) using 7-nitro-3,4-dihydropyrido[3,2-f][1,4]oxazepin-5(2H)-one (100 mg, 0.48 mmol) obtained in Example (38a) and 3-iodopyridine (118 mg, 0.57 mmol).

$^1$H NMR spectrum (CDCl$_3$, 400 MHz) δ: 9.34-9.30 (2H, m), 8.62-8.61 (2H, m), 7.74-7.71 (1H, m), 7.44 (1H, dd, J=8.0, 4.9 Hz), 4.89 (2H, t, J=4.1 Hz), 4.18 (2H, t, J=4.1 Hz).

(39b) 5-Chloro-2-methoxy-N-[5-oxo-4-(pyridin-3-yl)-2,3,4,5-tetrahydropyrido[3,2-f][1,4]oxazepin-7-yl]benzenesulfonamide The title compound (13 mg, yield for 2 steps: 8%) was obtained by production according to the method described in Examples (3b) and (1d) using 7-nitro-4-(pyridin-3-yl)-3,4-dihydropyrido[3,2-f][1,4]oxazepin-5(2H)-one (104 mg, 0.36 mmol) obtained in Example (39a) and 5-chloro-2-methoxybenzenesulfonyl chloride (21.7 mg, 0.09 mmol).

$^1$H NMR spectrum (DMSO-d6, 400 MHz) δ: 10.40 (1H, br s), 8.62 (1H, d, J=2.4 Hz), 8.50-8.49 (1H, m), 8.18 (1H, d, J=2.9 Hz), 8.01 (1H, d, J=2.9 Hz), 7.84 (1H, br d, J=8.3 Hz), 7.69-7.67 (2H, m), 7.49 (1H, dd, J=8.1, 4.6 Hz), 7.27-7.25 (1H, m), 4.59 (2H, t, J=4.1 Hz), 4.01 (2H, t, J=4.1 Hz), 3.88 (3H, s).

MS spectrum (ES/APCI$^+$): 461 (M+H), 463 (M+2+H).

(Example 40) 5-Chloro-N-(5'-oxo-4',5'-dihydrospiro[cyclopropane-1,3'-pyrido[3,2-f][1,4]oxazepin]-7'-yl)-2-(trifluoromethoxy)benzenesulfonamide

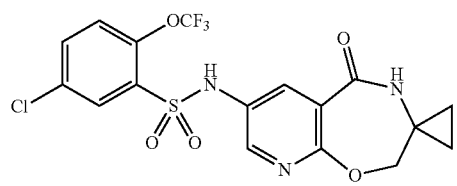 [SMILES: O=C1NC2(CC2)COc2ncc(NS(=O)(=O)c3cc(Cl)ccc3OC(F)(F)F)cc21]

(40a) 5-Chloro-2-(trifluoromethoxy)benzenesulfonyl chloride

To a suspension of 5-chloro-2-(trifluoromethoxy)aniline (5.00 g, 23.6 mmol) and dibenzyl disulfide (4.66 g, 18.9 mmol) in acetonitrile (75 mL), Isoamyl nitrite (3.46 mL, 26.0 mmol) was slowly added at 60° C. in an oil bath, and the mixture was stirred at the same temperature as above for 2 hours. The reaction mixture was cooled and then concentrated under reduced pressure, and the residue was purified in an automatic chromatography apparatus (n-hexane/ethyl acetate=100/0-95/5) to prepare 2-(benzylsulfanyl)-4-chlorophenyl trifluoromethyl ether (3.86 g, yield: 51%). To a mixture of the obtained 2-(benzylsulfanyl)-4-chlorophenyl trifluoromethyl ether (4.84 g, 15.2 mmol), acetic acid (4.5 mL) and water (3 mL) in acetonitrile (120 mL), 1,3-dichloro-5,5-dimethylhydantoin (5.98 g, 30.4 mmol) was added under ice cooling, and the mixture was stirred at the same temperature as above for 3 hours. The mixture was diluted by addition of a saturated aqueous solution of sodium bicarbonate, extracted with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (hexane/ethyl acetate=100/0-85/15) to obtain the title compound (3.64 g, yield: 81%).

$^1$H NMR spectrum (CDCl$_3$, 400 MHz) δ: 8.09 (1H, d, J=2.3 Hz), 7.75 (1H, dd, J=9.0, 2.7 Hz), 7.50-7.47 (1H, m).

(40b) 5-Chloro-N-[4'-(2,4-dimethoxybenzyl)-5'-oxo-4',5'-dihydrospiro[cyclopropane-1,3'-pyrido[3,2-f][1,4]oxazepin]-7'-yl]-2-(trifluoromethoxy)benzenesulfonamide To a mixture of 7'-amino-4'-(2,4-dimethoxybenzyl)spiro[cyclopropane-1,3'-pyrido[3,2-f][1,4]oxazepin]-5'(4'H)-one (95.0 mg, 0.267 mmol) obtained in Example (35d) and pyridine (0.432 mL, 5.35 mmol), 5-chloro-2-(trifluoromethoxy)benzenesulfonyl chloride (86.8 mg, 0.294 mmol) in Example (40a) was added at room temperature, and the mixture was stirred at 80° C. for 2 hours in an oil bath. The reaction mixture was cooled and then concentrated under reduced pressure, and the residue was purified in an automatic chromatography apparatus (ethyl acetate/methanol=100/0-90/10) to obtain the title compound (142 mg, yield: 87%).

$^1$H NMR spectrum (CDCl$_3$, 400 MHz) δ: 8.23 (1H, d, J=2.7 Hz), 7.91 (1H, d, J=2.7 Hz), 7.87 (1H, d, J=2.7 Hz), 7.57 (1H, dd, J=8.8, 2.5 Hz), 7.39-7.35 (1H, m), 7.17 (1H, d, J=8.2 Hz), 6.46-6.44 (2H, m), 4.68 (1H, br s), 3.96 (1H, br s), 3.81 (3H, s), 3.80 (3H, s), 0.93 (2H, br s), 0.69 (2H, br s).

(40c) 5-Chloro-N-(5'-oxo-4',5'-dihydrospiro[cyclopropane-1,3'-pyrido[3,2-f][1,4]oxazepin]-7'-yl)-2-(trifluoromethoxy)benzenesulfonamide To a solution of 5-chloro-N-[4'-(2,4-dimethoxybenzyl)-5'-oxo-4',5'-dihydrospiro[cyclopropane-1,3'-pyrido[3,2-f][1,4]oxazepin]-7'-yl]-2-(trifluoromethoxy)benzenesulfonamide (142 mg, 0.231 mmol) obtained in Example (40b) in chloroform (8 mL), anisole (0.0504 mL, 0.463 mmol), trifluoroacetic acid (4 mL, 52 mmol) and trifluoromethanesulfonic acid (0.0609 mL, 0.694 mmol) were added at room temperature, and the mixture was stirred at room temperature for 2 hours. The reaction mixture was diluted by addition of a saturated aqueous solution of sodium bicarbonate under ice cooling, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-90/10) to obtain the title compound (84 mg, yield: 78%).

$^1$H NMR spectrum (DMSO-d6, 400 MHz) δ: 10.73 (1H, br s), 8.87 (1H, br s), 8.11 (1H, d, J=2.4 Hz), 7.93-7.86 (3H, m), 7.61 (1H, d, J=8.8 Hz), 4.30 (2H, br s), 0.80 (2H, br s), 0.77 (2H, br s).

MS spectrum (ES/APCI$^+$): 464 (M+H), 466 (M+2+H).

(Example 41) 5-Fluoro-N-(5'-oxo-4',5'-dihydrospiro[cyclopropane-1,3'-pyrido[3,2-f][1,4]oxazepin]-7'-yl)-2-(trifluoromethoxy)benzenesulfonamide

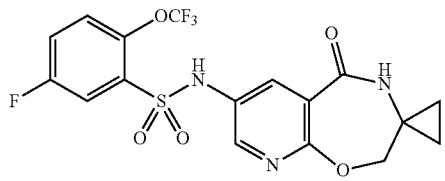 [SMILES: O=C1NC2(CC2)COc2ncc(NS(=O)(=O)c3cc(F)ccc3OC(F)(F)F)cc21]

(41a) 5-Fluoro-2-(trifluoromethoxy)benzenesulfonyl chloride

The title compound (0.82 g, yield for 2 steps: 29%) was obtained by production according to the method described in Example (40a) using 5-fluoro-2-(trifluoromethoxy)aniline (2.00 g, 10.3 mmol).

$^1$H NMR spectrum (CDCl$_3$, 400 MHz) δ: 7.84 (1H, dd, J=6.8, 2.9 Hz), 7.56-7.47 (2H, m).

(41b) N-[4'-(2,4-Dimethoxybenzyl)-5'-oxo-4',5'-dihydrospiro[cyclopropane-1,3'-pyrido[3,2-f][1,4]oxazepin]-7'-yl]-5-fluoro-2-(trifluoromethoxy)benzenesulfonamide To a mixture of 7'-amino-4'-(2,4-dimethoxybenzyl)spiro[cyclopropane-1,3'-pyrido[3,2-f][1,4]oxazepin]-5'(4'H)-one (100 mg, 0.281 mmol) obtained in Example (35d) and pyridine (0.453 mL, 5.63 mmol), 5-fluoro-2-(trifluoromethoxy)benzenesulfonyl chloride (94.1 mg, 0.338 mmol) in Example (41a) was added at room temperature, and the mixture was stirred at 80° C. for 5 hours in an oil bath. The reaction mixture was cooled and then concentrated under reduced pressure, and the residue was purified in an automatic chromatography apparatus (n-hexane/ethyl acetate=100/0-0/100) to obtain the title compound (156 mg, yield: 93%).

$^1$H NMR spectrum (CDCl$_3$, 400 MHz) δ: 8.27 (1H, d, J=2.7 Hz), 7.94 (1H, d, J=2.7 Hz), 7.63 (1H, dd, J=7.4, 3.1 Hz), 7.32-7.28 (2H, m), 7.16 (1H, d, J=8.2 Hz), 6.46-6.43 (2H, m), 4.69 (1H, br s), 3.95 (2H, br s), 3.81 (3H, s), 3.80 (3H, s), 0.92 (2H, br s), 0.69 (2H, br s).

(41c) 5-Fluoro-N-(5'-oxo-4',5'-dihydrospiro[cyclopropane-1,3'-pyrido[3,2-f][1,4]oxazepin]-7'-yl)-2-(trifluoromethoxy)benzenesulfonamide To a suspension of N-[4'-(2,4-dimethoxybenzyl)-5'-oxo-4',5'-dihydrospiro[cyclopropane-1,3'-pyrido[3,2-f][1,4]oxazepin]-7'-yl]-5-fluoro-2-(trifluoromethoxy)benzenesulfonamide (156 mg, 0.261 mmol) obtained in Example (41b) in chloroform (5 mL), anisole (84.7 mg, 0.783 mmol), trifluoroacetic acid (0.40 mL, 5.2 mmol) and trifluoromethanesulfonic acid (0.0687 mL, 0.783 mmol) were added at room temperature, and the mixture was stirred at room temperature for 2 hours. To the mixture, an additional trifluoroacetic acid (2 mL) was added, and the mixture was stirred at room temperature for further 2 hours. The reaction mixture was diluted by addition of a saturated aqueous solution of sodium bicarbonate under ice cooling, followed by extraction with chloroform. The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-95/5) to obtain the title compound (97 mg, yield: 83%).

$^1$H NMR spectrum (DMSO-d6, 400 MHz) δ: 10.75 (1H, br s), 8.88 (1H, br s), 8.11 (1H, d, J=2.7 Hz), 7.92 (1H, d, J=2.7 Hz), 7.75-7.66 (3H, m), 4.30 (2H, br s), 0.82-0.75 (4H, m).

MS spectrum (ES/APCI$^+$): 448 (M+H).

(Example 42) 2-Ethoxy-5-fluoro-N-(5'-oxo-4',5'-dihydrospiro[cyclopropane-1,3'-pyrido[3,2-f][1,4]oxazepin]-7'-yl)benzenesulfonamide

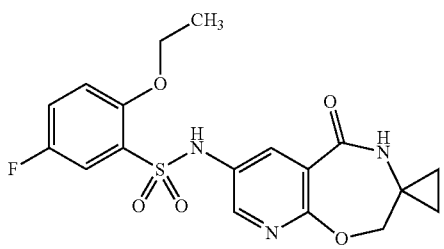 [SMILES: CCOc1ccc(F)cc1S(=O)(=O)Nc1cnc2c(c1)C(=O)NC1(CC1)CO2]

(42a) 5-Fluoro-2-ethoxybenzenesulfonyl chloride

The title compound (3.16 g, yield: 36%) was obtained by production according to the method described in Example (13a) using 1-ethoxy-4-fluorobenzene (5.11 g, 36.5 mmol).

$^1$H NMR spectrum (CDCl$_3$, 400 MHz) δ: 7.70 (1H, dd, J=7.4, 3.1 Hz), 7.41-7.36 (1H, m), 7.07 (1H, dd, J=9.4, 3.9 Hz), 4.26 (2H, q, J=6.8 Hz), 1.55 (3H, t, J=6.8 Hz).

(42b) N-[4'-(2,4-Dimethoxybenzyl)-5'-oxo-4',5'-dihydrospiro[cyclopropane-1,3'-pyrido[3,2-f][1,4]oxazepin]-7'-yl]-2-ethoxy-5-fluorobenzenesulfonamide To a mixture of 7'-amino-4'-(2,4-dimethoxybenzyl)spiro[cyclopropane-1,3'-pyrido[3,2-f][1,4]oxazepin]-5'(4'H)-one (100 mg, 0.281 mmol) obtained in Example (35d) and pyridine (0.453 mL, 5.63 mmol), 5-Fluoro-2-ethoxybenzenesulfonyl chloride (73.9 mg, 0.310 mmol) obtained in Example (42a) was added at room temperature, and the mixture was stirred at 80° C. for 2 hours in an oil bath. The reaction mixture was cooled and then concentrated under reduced pressure, and the residue was purified in an automatic chromatography apparatus (n-hexane/ethyl acetate=100/0-0/100) to obtain the title compound (146 mg, yield: 93%).

$^1$H NMR spectrum (CDCl$_3$, 400 MHz) δ: 8.20 (1H, d, J=2.7 Hz), 7.85 (1H, d, J=2.7 Hz), 7.47 (1H, dd, J=7.4, 3.1 Hz), 7.23-7.14 (2H, m), 7.02-6.95 (2H, m), 6.46-6.43 (2H, m), 4.66 (1H, br s), 4.29 (2H, q, J=7.0 Hz), 3.92 (1H, br s), 3.80 (3H, s), 3.79 (3H, s), 1.58 (3H, t, J=7.0 Hz), 0.87 (2H, br s), 0.63 (2H, br s).

(42c) 2-Ethoxy-5-fluoro-N-(5'-oxo-4',5'-dihydrospiro[cyclopropane-1,3'-pyrido[3,2-f][1,4]oxazepin]-7'-yl)benzenesulfonamide To a suspension of N-[4'-(2,4-dimethoxybenzyl)-5'-oxo-4',5'-dihydrospiro[cyclopropane-1,3'-pyrido[3,2-f][1,4]oxazepin]-7'-yl]-2-ethoxy-5-fluorobenzenesulfonamide (146 mg, 0.262 mmol) obtained in Example (42b) in chloroform (4 mL), anisole (0.0571 mL, 0.524 mmol), trifluoroacetic acid (2 mL, 26.1 mmol) and trifluoromethanesulfonic acid (0.0689 mL, 0.786 mmol) were added at room temperature, and the mixture was stirred at room temperature for 3 hours. The reaction mixture was diluted by addition of a saturated aqueous solution of sodium bicarbonate under ice cooling, followed by extraction with chloroform. The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-90/10) to obtain a crude solid. To a suspension of the crude solid in ethanol (3 mL), a 1 N aqueous sodium hydroxide solution (0.40 mL) was added and the mixture was stirred at room temperature until dissolved. The mixture was concentrated under reduced pressure, diluted by addition of water, and then filtered. A 1 N hydrochloric acid (0.40 mL) was added to the filtrate, the precipitated solid was collected by filtration, washed with water and ethanol, and then dried to obtain the title compound (95 mg, yield: 89%).

$^1$H NMR spectrum (DMSO-d6, 400 MHz) δ: 10.15 (1H, s), 8.83 (1H, s), 8.09 (1H, d, J=2.7 Hz), 7.95 (1H, d, J=2.7 Hz), 7.52-7.44 (2H, m), 7.24 (1H, dd, J=9.0, 4.3 Hz), 4.26 (br 2H, s), 4.16 (2H, q, J=7.0 Hz), 1.26 (3H, t, J=7.0 Hz), 0.77-0.71 (4H, m).

MS spectrum (ES/APCI$^+$): 408 (M+H).

(Example 43) 2,5-Dimethoxy-N-(5'-oxo-4',5'-dihydrospiro[cyclopropane-1,3'-pyrido[3,2-f][1,4]oxazepin]-7'-yl)benzenesulfonamide

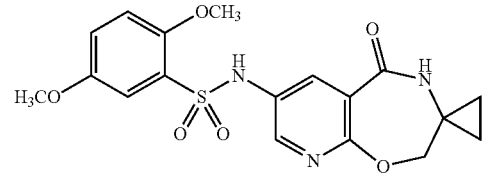 [SMILES: COc1ccc(OC)c(S(=O)(=O)Nc2cnc3c(c2)C(=O)NC2(CC2)CO3)c1]

(43a) N-[4'-(2,4-Dimethoxybenzyl)-5'-oxo-4',5'-dihydrospiro[cyclopropane-1,3'-pyrido[3,2-f][1,4]oxazepin]-7'-yl]-2,5-dimethoxybenzenesulfonamide To a mixture of 7'-amino-4'-(2,4-dimethoxybenzyl)spiro[cyclopropane-1,3'-pyrido[3,2-f][1,4]oxazepin]-5' (4'H)-one (90.0 mg, 0.253 mmol) obtained in Example (35d) and pyridine (0.408 mL, 5.06 mmol), 2,5-dimethoxybenzenesulfonyl chloride (65.9 mg, 0.279 mmol) was added at room temperature, and the mixture was stirred at 80° C. for 3 hours in an oil bath. The reaction mixture was cooled and then concentrated under reduced pressure, and the residue was purified in an automatic chromatography apparatus (n-hexane/ethyl acetate=100/0-0/100) to obtain the title compound (143 mg, yield: quantitative).

$^1$H NMR spectrum (CDCl$_3$, 400 MHz) δ: 8.22 (1H, d, J=2.7 Hz), 7.88 (1H, br d, J=2.7 Hz), 7.37-7.28 (2H, m), 7.15 (1H, br d, J=8.6 Hz), 7.04 (1H, dd, J=9.0, 3.1 Hz), 6.97 (1H, d, J=9.0 Hz), 6.45-6.43 (2H, m), 4.66 (2H, br s), 3.99 (3H, s), 3.91 (2H, br s), 3.80 (3H, s), 3.79 (3H, s), 3.73 (3H, s), 0.86 (2H, br s), 0.61 (2H, br s).

(43b) 2,5-Dimethoxy-N-(5'-oxo-4',5'-dihydrospiro [cyclopropane-1,3'-pyrido[3,2-f][1,4]oxazepin]-7'-yl) benzenesulfonamide To a suspension of N-[4'-(2,4-dimethoxybenzyl)-5'-oxo-4',5'-dihydrospiro[cyclopropane-1,3'-pyrido[3,2-f][1,4]oxazepin]-7'-yl]-2,5-dimethoxybenzenesulfonamide (0.143 mg, 0.257 mmol) obtained in Example (43a) in chloroform (4 mL), anisole (0.0561 mL, 0.515 mmol), trifluoroacetic acid (2 mL, 26 mmol) and trifluoromethanesulfonic acid (0.0678 mL, 0.772 mmol) were added under ice cooling, the mixture was stirred at the same temperature as above for 3 hours and subsequently stirred at room temperature for 2 hours. The reaction mixture was diluted by addition of a saturated aqueous solution of sodium bicarbonate under ice cooling, followed by extraction with chloroform. The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-90/10) to obtain the crude solid. To a suspension of the crude solid in ethanol (3 mL), a 1 N aqueous sodium hydroxide solution (1 mL) was added and the mixture was stirred at room temperature until dissolved. The mixture was concentrated under reduce pressure, diluted by addition of ethyl acetate and water. Most of the organic solvent was distilled off under reduce pressure, and then filtered. A 1 N hydrochloric acid (1 mL) was added the filtrate, the precipitated solid was collected by filtration, washed with water and ethanol, and then dried to obtain the title compound (55 mg, yield: 53%).

$^1$H NMR spectrum (DMSO-d6, 400 MHz) δ: 10.17 (1H, br s), 8.83 (1H, br s), 8.07 (1H, d, J=2.7 Hz), 7.95 (1H, d, J=2.7 Hz), 7.20-7.15 (3H, m), 4.24 (2H, br s), 3.81 (3H, s), 3.71 (3H, s), 0.74 (4H, br s).

MS spectrum (ES/APCI$^+$): 406 (M+H).

(Example 44) 5-Chloro-2-methoxy-N-[5-oxo-3-(pyridin-3-yl)-2,3,4,5-tetrahydropyrido[3,2-f][1,4]oxazepin-7-yl]benzenesulfonamide

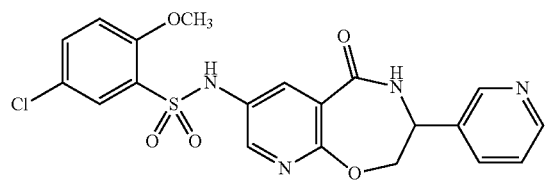 [SMILES: COc1ccc(Cl)cc1S(=O)(=O)Nc1cnc2c(c1)C(=O)NC(c1cccnc1)CO2]

(44a) 2-[(2,4-Dimethoxybenzyl)amino]-2-(pyridin-3-yl)ethanol

The title compound (approximately 77% content, 0.9217 g, yield: 69%) as a mixture containing 2.5-dimethoxybenzylalcohol was obtained by production according to the method of Example (8a) using 2,4-dimethoxybenzaldehyde (627.6 mg, 3.78 mmol) and 2-amino-2-(pyridin-3-yl)ethanol (495.3 mg, 3.59 mmol).

$^1$H NMR spectrum (CDCl$_3$, 400 MHz) δ: 8.54-8.51 (1.32H, m), 7.70-7.68 (0.66H, m), 7.29-7.26 (0.66H, m), 7.17 (0.34H, d, J=8.2 Hz), 7.03-7.01 (0.66H, d, J=7.8 Hz), 6.48-6.40 (2H, m), 4.61 (0.68H, s), 3.85-3.79 (6.66H, m), 3.76-3.70 (1.32H, m), 3.56-3.52 (1.32H, m).

(44b) 4-(2,4-Dimethoxybenzyl)-7-nitro-3-(pyridin-3-yl)-3,4-dihydropyrido[3,2-f][1,4]oxazepin-5(2H)-one The title compound (283.2 mg, yield for 2 steps: 27%) was obtained by production according to the method described in Examples (1a) and (35c) using 2-chloro-5-nitropyridine-3-carboxylic acid (501.1 mg, 2.47 mmol) and 2-[(2,4-dimethoxybenzyl)amino]-2-(pyridin-3-yl)ethanol (approximately 77% content, 0.912 g, 2.44 mmol) obtained in Example (44a).

$^1$H NMR spectrum (CDCl$_3$, 400 MHz) δ: 9.66 (1H, d, J=2.7 Hz), 9.10 (1H, d, J=2.7 Hz), 8.51 (1H, dd, J=4.7, 1.6 Hz), 8.42 (1H, br d, J=2.3 Hz), 7.42 (1H, d, J=8.2 Hz), 7.35-7.32 (1H, m), 7.21-7.17 (1H, m), 6.49 (1H, dd, J=8.2, 2.3 Hz), 6.40 (1H, d, J=2.3 Hz), 5.19 (1H, d, J=5.3 Hz), 5.10 (1H, d, J=14.5 Hz), 5.02 (1H, dd, J=13.1, 5.3 Hz), 4.56 (1H, d, J=13.3 Hz), 4.50 (1H, d, J=14.5 Hz), 3.80 (3H, s), 3.72 (3H, s).

(44c) 7-Amino-4-(2,4-dimethoxybenzyl)-3-(pyridin-3-yl)-3,4-dihydropyrido[3,2-f][1,4]oxazepin-5(2H)-one The title compound (270.0 mg, yield: quantitative) was obtained by production according to the method of Example (8d) using 4-(2,4-dimethoxybenzyl)-7-nitro-3-(pyridin-3-yl)-3,4-dihydropyrido[3,2-f][1,4]oxazepin-5(2H)-one (287.5 mg, 0.659 mmol) obtained in example (44b).

$^1$H NMR spectrum (CDCl$_3$, 400 MHz) δ: 8.48 (1H, dd, J=4.9, 1.6 Hz), 8.40 (1H, d, J=2.3 Hz), 8.20 (1H, d, J=2.7 Hz), 7.81 (1H, d, J=2.7 Hz), 7.39-7.35 (2H, m), 7.17 (1H, dd, J=8.0, 4.9 Hz), 6.47 (1H, dd, J=8.2, 2.3 Hz), 6.39 (1H, d, J=2.3 Hz), 5.10 (1H, d, J=14.5 Hz), 4.97 (1H, d, J=5.3 Hz), 4.75 (1H, dd, J=13.1, 5.3 Hz), 4.38-4.34 (2H, m), 3.80 (3H, s), 3.72 (3H, s), 3.60 (2H, br s).

(44d) 5-Chloro-2-methoxy-N-[5-oxo-3-(pyridin-3-yl)-2,3,4,5-tetrahydropyrido[3,2-f][1,4]oxazepin-7-yl]benzenesulfonamide The title compound (191.0 mg, yield for 2 steps: 64%) was obtained by production according to the method described in Examples (1d) and (9) using 7-amino-4-(2,4-dimethoxybenzyl)-3-(pyridine-3-yl)-3,4-dihydropyrido[3,2-f][1,4]oxazepin-5(2H)-one (267.5 mg, 0.66 mmol) obtained in Example (44c) and 5-chloro-2-methoxybenzenesulfonyl chloride (166.7 mg, 0.69 mmol).

$^1$H NMR spectrum (DMSO-d6, 400 MHz) δ: 10.33 (1H, br s), 8.93 (1H, br d, J=5.5 Hz), 8.48-8.46 (2H, m), 8.35 (1H, d, J=2.7 Hz), 8.04 (1H, d, J=2.7 Hz), 7.70-7.69 (2H, m), 7.60-7.57 (1H, m), 7.33 (1H, dd, J=7.8, 4.7 Hz), 7.26 (1H, d, J=9.0 Hz), 4.93 (1H, t, J=5.5 Hz), 4.78 (1H, dd, J=12.9, 5.5 Hz), 4.51 (1H, br d, J=12.9 Hz).

MS spectrum (ES/APCI$^+$): 461 (M+H), 463 (M+2+H).

(Example 45) 7-{[(5-Chloro-2-methoxyphenyl)sulfonyl]amino}-N,N-dimethyl-5-oxo-2,3,4,5-tetrahydropyrido[3,2-f][1,4]oxazepine-3-carboxamide

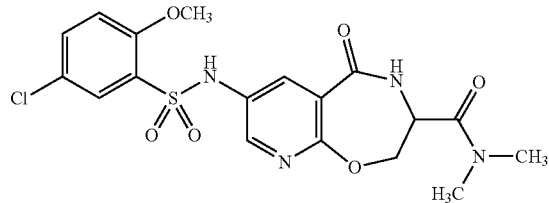 [SMILES: COc1ccc(Cl)cc1S(=O)(=O)Nc1cnc2c(c1)C(=O)NC(C(=O)N(C)C)CO2]

(45a) O-Benzyl-N-[(benzyloxy) carbonyl]serine

To a suspension of O-benzylserine (5.00 g, 25.6 mmol) in 1,4-dioxane (50 mL), a 2 N aqueous sodium hydroxide solution (26.8 mL, 53.8 mmol) was added, and the mixture was stirred at room temperature for 10 minutes. Subsequently, to the mixture, benzyl chloroformate (3.82 mL, 26.9 mmol) was added, and the mixture was stirred at room temperature for 3 hours. The reaction mixture was concentrated under reduce pressure, and diluted by addition of a 5 N hydrochloric acid (10.8 mL, 54.2 mmol), followed by extraction with ethyl acetate. The organic layer was washed with water and a saturated aqueous solution of sodium chloride, and dried over anhydrous magnesium sulfate. After filtration, the solvent was distilled off under reduced pressure. To the residue, n-hexane (20 mL) and ethyl acetate (1 mL) were added, and the precipitated solid was collected by filtration, washed with n-hexane, and then dried to obtain the title compound (7.24 g, yield: 86%).

$^1$H NMR spectrum (CDCl$_3$, 400 MHz) δ: 7.37-7.27 (10H, m), 5.64 (1H, br d, J=8.2 Hz), 5.15 (1H, br d, J=12.1 Hz), 5.11 (1H, br d, J=12.1 Hz), 4.57-4.53 (3H, m), 3.96 (1H, br dd, J=9.4, 3.1 Hz), 3.72 (1H, br dd, J=9.4, 3.3 Hz).

(45b) Benzyl [3-(benzyloxy)-1-(dimethylamino)-1-oxopropan-2-yl]carbamate

To a solution of O-benzyl-N-[(benzyloxy)carbonyl]serine (1.50 g, 4.55 mmol) obtained in example (45a), N-[3-(dimethylamino)propyl]-N'-ethylcarbodiimide hydrochloride (1.06 g, 5.53 mmol) and 1-hydroxybenzotriazole (0.68 g, 5.0 mmol) in methylene chloride (22 mL), dimethylamine in tetrahydrofuran (2.0 mol/L, 5.5 mL, 11 mmol) was added under ice cooling, and the mixture was stirred at the same temperature as above for 10 minutes and subsequently at room temperature for 1 hour. The mixture was diluted by addition of a 1 N hydrochloric acid (50 mL), followed by extraction with ethyl acetate. The organic layer was washed with water, a saturated aqueous solution of sodium bicarbonate and a saturated aqueous solution of sodium chloride, and dried over anhydrous magnesium sulfate. After filtration, the solvent was distilled off under reduced pressure, and the residue was purified by silica gel column chromatography (ethyl acetate/n-hexane=2/1-1/0) to obtain the title compound (1.47 g, yield: 91%)

$^1$H NMR spectrum (CDCl$_3$, 400 MHz) δ: 7.35-7.26 (10H, m), 5.75 (1H, d, J=8.2 Hz), 5.10 (2H, br s), 4.95-4.90 (1H, m), 4.54 (1H, d, J=12.1 Hz), 4.49 (1H, d, J=12.1 Hz), 3.66 (1H, dd, J=9.4, 5.5 Hz), 3.59 (1H, dd, J=9.4, 7.0 Hz), 3.05 (3H, s), 2.97 (3H, s).

(45c) N,N-Dimethylserinamide

A mixture of benzyl [3-(benzyloxy)-1-(dimethylamino)-1-oxopropan-2-yl]carbamate (1.46 g, 4.10 mmol) obtained in Example (45b) and 10% palladium carbon (water content: 54.6%, 0.28 g) in ethanol (41 mL) was stirred at room temperature for 1 hour at normal pressure under the hydrogen atmosphere. Subsequently the mixture was stirred at 50° C. for 24 hours in an oil bath at normal pressure under the hydrogen atmosphere. Hydrogen in the reaction container was replaced with nitrogen, and then, the reaction mixture was filtered through pad of Celite 545(R). The solvent in the filtrate was distilled off under reduced pressure to obtain the title compound (approximately 70% content, 0.60 g, yield: 78%) as a mixture containing O-benzyl-N,N-dimethylserinamide $^1$H NMR spectrum (CDCl$_3$, 400 MHz) δ: 7.36-7.29 (1H, m), 4.53 (0.4H, br s), 3.98 (0.2H, dd, J=7.0, 5.9 Hz), 3.77 (0.8H, dd, J=7.0, 4.7 Hz), 3.66 (0.8H, dd, J=10.9, 4.7 Hz), 3.57 (0.2H, dd, J=9.2, 5.9 Hz), 3.50-3.44 (1H, m), 3.10 (2.4H, s), 3.04 (0.6H, s), 2.98 (2.4H, s), 2.97 (0.6H, s).

(45d) N$^2$-(2,4-Dimethoxybenzyl)-N,N-dimethylserinamide

The title compound (0.76 g, yield: 85%) was obtained by production according to the method of Example (8a) using 2,4-dimethoxybenzaldehyde (0.68 g, 4.1 mmol) and N,N-dimethylserinamide (approximately 70% content, 0.60 g, 3.2 mmol) obtained in Example (45c).

$^1$H NMR spectrum (CDCl$_3$, 400 MHz) δ: 7.14 (1H, d, J=7.8 Hz), 6.44-6.41 (2H, m), 3.82 (3H, s), 3.80 (3H, s), 3.73-3.63 (3H, m) 3.59 (1H, dd, J=7.8, 4.7 Hz), 3.37 (1H, dd, J=10.2, 7.8 Hz), 2.99 (3H, s), 2.89 (3H, s).

(45e) 4-(2,4-Dimethoxybenzyl)-N,N-dimethyl-7-nitro-5-oxo-2,3,4,5-tetrahydropyrido[3,2-f][1,4]oxazepine-3-carboxamide The title compound (0.55 g, yield for 2 steps: 46%) was obtained by production according to the method described in Examples (1a) and (35c) using 2-chloro-5-nitropyridine-3-carboxylic acid (0.55 g, 2.7 mmol) and N$^2$-(2,4-dimethoxybenzyl)-N,N-dimethylserinamide (0.76 g, 2.7 mmol) obtained in example (45d).

$^1$H NMR spectrum (CDCl$_3$, 400 MHz) δ: 9.73 (1H, d, J=2.7 Hz), 9.12 (1H, d, J=2.7 Hz), 7.37 (1H, d, J=8.2 Hz), 6.51-6.47 (2H, m), 5.04 (1H, d, J=14.5 Hz), 4.95-4.89 (2H, m), 4.43 (1H, d, J=14.5 Hz), 4.34 (1H, d, J=12.1 Hz), 3.83 (3H, s), 3.81 (3H, s), 3.04 (3H, s), 2.88 (3H, s).

(45f) 7-Amino-4-(2,4-dimethoxybenzyl)-N,N-dimethyl-5-oxo-2,3,4,5-tetrahydropyrido[3,2-f][1,4]oxazepine-3-carboxamide The title compound (342.7 mg, yield: 67%) was obtained by production according to the method of Example (8d) using 4-(2,4-dimethoxybenzyl)-N,N-dimethyl-7-nitro-5-oxo-2,3,4,5-tetrahydropyrido[3,2-f][1,4]oxazepine-3-carboxamide (552.0 mg, 1.24 mmol) obtained in Example (45e).

$^1$H NMR spectrum (CDCl$_3$, 400 MHz) δ: 8.19 (1H, d, J=2.7 Hz), 7.79 (1H, d, J=2.7 Hz), 7.35 (1H, d, J=8.2 Hz), 6.49-6.45 (2H, m), 5.09 (1H, d, J=14.5 Hz), 4.79-4.73 (2H, m), 4.31 (1H, d, J=14.5 Hz), 4.18-4.13 (1H, m), 3.81 (3H, s), 3.81 (3H, s), 3.55 (1H, br d, J=9.4 Hz), 3.00 (3H, s), 2.90 (3H, s).

(45g) 7-{[(5-Chloro-2-methoxyphenyl) sulfonyl]amino}-N,N-dimethyl-5-oxo-2,3,4,5-tetrahydropyrido[3,2-f][1,4]oxazepine-3-carboxamide The title compound (261.1 mg, yield for 2 steps: 69%) was obtained by production according to the method described in Examples (1d) and (9) using 7-amino-4-(2,4-dimethoxybenzyl)-N,N-dimethyl-5-oxo-2,3,4,5-tetrahydropyrido[3,2-f][1,4]oxazepine-3-carboxamide (340.2 mg, 0.82 mmol) obtained in Example (45f) and 5-Chloro-2-methoxybenzenesulfonyl chloride (207.3 mg, 0.86 mmol).

$^1$H NMR spectrum (CDCl$_3$, 400 MHz) δ: 8.40 (1H, d, J=2.7 Hz), 8.14 (1H, d, J=2.7 Hz), 7.74 (1H, d, J=2.7 Hz), 7.48 (1H, dd, J=9.0, 2.7 Hz), 7.34 (1H, br s), 7.12 (1H, br s), 7.01 (1H, d, J=9.0 Hz), 4.72 (1H, br d, J=12.5 Hz), 4.56 (1H, br dd, J=6.6, 3.5 Hz), 4.27 (1H, dd, J=12.5, 6.6 Hz), 4.08 (3H, s), 3.11 (3H, s), 3.05 (3H, s).

MS spectrum (ES/APCI$^+$): 455 (M+H), 457 (M+2+H).

Example 46

5-chloro-2-methoxy-N-[3-(morpholin-4-ylcarbonyl)-5-oxo-2,3,4,5-tetrahydropyrido[3,2-f][1,4]oxazepin-7-yl]benzenesulfonamide

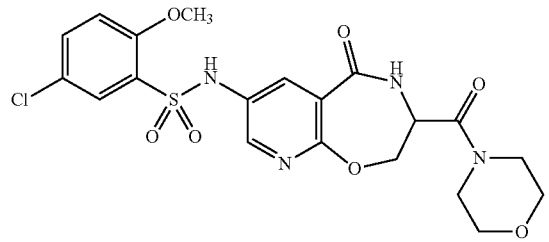 [SMILES: COc1ccc(Cl)cc1S(=O)(=O)Nc1cnc2c(c1)C(=O)NC(C(=O)N1CCOCC1)CO2]

(46a) 2-[(2,4-Dimethoxybenzyl)amino]-3-hydroxy-1-(morpholin-4-yl)propan-1-one

The title compound (1.39 g, yield for 3 steps: 88%) was obtained by production according to the method described in Examples (45b), (45c) and (8a) using O-benzyl-N-[(benzyloxy)carbonyl]serine (1.50 g, 4.55 mmol) obtained in example (45a), morpholine (0.96 mL, 11 mmol) and 2,4-dimethoxybenzaldehyde (0.71 g, 4.3 mmol).

$^1$H NMR spectrum (CDCl$_3$, 400 MHz) δ: 7.11 (1H, d, J=8.2 Hz), 6.44-6.41 (2H, m), 3.82 (3H, s), 3.80 (3H, s), 3.75 (1H, d, J=12.9 Hz), 3.68-3.51 (9H, m), 3.44-3.39 (3H, m).

(46b) 4-(2,4-Dimethoxybenzyl)-3-(morpholin-4-ylcarbonyl)-7-nitro-3,4-dihydropyrido[3,2-f][1,4]oxazepin-5(2H)-one The title compound (0.87 g, yield for 2 steps: 45%) was obtained by production according to the method described in Examples (1a) and (35c) using 2-chloro-5-nitropyridine-3-carboxylic acid (0.85 g, 4.2 mmol) and 2-[(2,4-dimethoxybenzyl)amino]-3-hydroxy-1-(morpholin-4-yl)propan-1-one (1.40 g, 4.3 mmol) obtained in Example (46a).

$^1$H NMR spectrum (CDCl$_3$, 400 MHz) δ: 9.75 (1H, d, J=2.7 Hz), 9.13 (1H, d, J=2.7 Hz), 7.33 (1H, d, J=8.2 Hz), 6.51-6.47 (2H, m), 4.99 (1H, d, J=14.1 Hz), 4.86-4.79 (2H, m), 4.53 (1H, d, J=14.1 Hz), 4.36 (1H, d, J=12.9 Hz), 3.83 (3H, s), 3.81 (3H, s), 3.74-3.29 (8H, m).

(46c) 5-Chloro-2-methoxy-N-[3-(morpholin-4-ylcarbonyl)-5-oxo-2,3,4,5-tetrahydropyrido[3,2-f][1,4]oxazepin-7-yl]benzenesulfonamide The title compound (255.5 mg, yield for 3 steps: 28%) was obtained by production according to the method described in Examples (8d), (1d) and (9) using 4-(2,4-dimethoxybenzyl)-3-(morpholin-4-ylcarbonyl)-7-nitro-3,4-dihydropyrido[3,2-f][1,4]oxazepin-5(2H)-one (0.87 g, 1.8 mmol) obtained in Example (46b) and 5-chloro-2-methoxybenzenesulfonyl chloride (0.32 g, 1.3 mmol).

$^1$H NMR spectrum (CDCl$_3$, 400 MHz) δ: 10.28 (1H, br s), 8.36 (1H, br d, J=5.5 Hz), 8.32 (1H, d, J=2.7 Hz), 8.03 (1H, d, J=2.7 Hz), 7.68-7.65 (2H, m), 7.26 (1H, d, J=8.6 Hz), 4.76 (1H, t, J=5.5 Hz), 4.62 (1H, dd, J=12.9, 5.5 Hz), 4.33 (1H, d, J=12.5 Hz), 3.88 (3H, s), 3.60-3.37 (8H, m).

MS spectrum (ES/APCI$^+$): 497 (M+H), 499 (M+2+H).

(Example 47) Potassium [[(5-chloro-2-methoxyphenyl) sulfonyl](5-oxo-2,3,4,5-tetrahydropyrido[3,2-f][1,4]oxazepin-7-yl)azanide (potassium salt of Example 9)

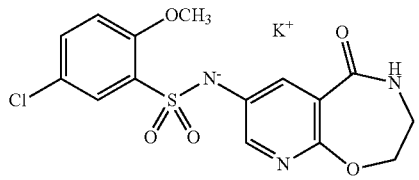 [SMILES: COc1ccc(Cl)cc1S(=O)(=O)[N-]c1cnc2c(c1)C(=O)NCCO2 ; [K+]]

(47a) 5-Chloro-N-[4-(2,4-dimethoxybenzyl)-5-oxo-2,3,4,5-tetrahydropyrido[3,2-f][1,4]oxazepin-7-yl]-2-methoxybenzenesulfonamide To a mixture of 7-amino-4-(2,4-dimethoxybenzyl)-3,4-dihydropyrido[3,2-f][1,4]oxazepin-5(2H)-one (1.31 g, 3.98 mmol) obtained in Example (8d) and pyridine (20 mL, 249 mmol), 5-chloro-2-methoxybenzenesulfonyl chloride (1.035 g, 4.29 mmol) was added at room temperature, and the mixture was stirred at 80° C. for 2.5 hours in an oil bath. The reaction mixture was cooled and then concentrated under reduced pressure, and the residue was purified in an automatic chromatography apparatus (ethyl acetate/methanol=100/0-85/15) to obtain the title compound (2.17 g, yield: quantitative).

$^1$H NMR spectrum (CDCl$_3$, 400 MHz) δ: 8.24 (1H, d, J=3.0 Hz), 8.07 (1H, d, J=3.0 Hz), 7.74 (1H, d, J=2.4 Hz), 7.48 (1H, dd, J=8.8, 2.7 Hz), 7.30-7.22 (2H, m), 7.01 (1H, d, J=9.1 Hz), 6.49-6.46 (2H, m), 4.70 (2H, s), 4.32 (2H, t, J=4.6 Hz), 4.09 (3H, s), 3.81-3.80 (6H, m), 3.60 (2H, t, J=4.6 Hz).

(47b) 5-Chloro-2-methoxy-N-(5-oxo-2,3,4,5-tetrahydropyrido[3,2-f][1,4]oxazepin-7-yl)benzenesulfonamide To a suspension of 5-chloro-N-[4-(2,4-dimethoxybenzyl)-5-oxo-2,3,4,5-tetrahydropyrido[3,2-f][1,4]oxazepin-7-yl]-2-methoxybenzenesulfonamide (2.17 g, 4.06 mmol) obtained in Example (47a) in chloroform (30 mL), anisole (0.88 mL, 8.1 mmol), trifluoroacetic acid (15 mL, 195 mmol) and trifluoromethanesulfonic acid (0.73 mL, 8.3 mmol) were added at room temperature, and the mixture was stirred at room temperature for 1 hour. The reaction mixture was concentrated under reduced pressure, and the concentrated mixture was diluted by addition of chloroform and a saturated aqueous solution of sodium bicarbonate. The precipitated solid was collected by filtration. An organic layer of the filtrate was separated, and dried over anhydrous sodium sulfate. After filtration, the solvent was distilled off under reduced pressure. The residue was combined with the above precipitated solid, diisopropyl ether was added thereto, and the suspension was stirred at room temperature for 1 hour. The precipitated solid was collected by filtration, and then dried to obtain the title compound (1.2921 g, yield: 83%).

$^1$H NMR spectrum (DMSO-d6, 400 MHz) δ: 10.29 (1H, br s), 8.53 (1H, br t, J=5.2 Hz), 8.11-8.08 (2H, m), 7.69-7.64 (2H, m), 7.26 (1H, d, J=8.5 Hz), 4.37-4.35 (2H, m), 3.88 (3H, s), 3.38-3.34 (2H, m).

(47c) Potassium [(5-chloro-2-methoxyphenyl)sulfonyl](5-oxo-2,3,4,5-tetrahydropyrido[3,2-f][1,4]oxazepin-7-yl)azanide To a suspension of 5-chloro-2-methoxy-N-(5-oxo-2,3,4,5-tetrahydropyrido[3,2-f][1,4]oxazepin-7-yl)benzenesulfonamide (1.0921 g, 2.845 mmol) obtained in Example (47b) in ethanol (12 mL), a solution of 0.5 N potassium hydroxide in ethanol (5.68 mL, 2.85 mmol) was added at room temperature, and the mixture was stirred at room temperature for 1 hour. The precipitated solid was collected by filtration, washed with ethanol and then dried to obtain the title compound (1.1065 g, yield: 92%).

$^1$H NMR spectrum (DMSO-d6, 400 MHz) δ: 8.19 (1H, br t, J=5.2 Hz), 7.70 (1H, br t, J=2.4 Hz), 7.65-7.61 (2H, m), 7.35-7.32 (1H, m), 6.99 (1H, d, J=9.1 Hz), 4.18 (2H, t, J=5.2 Hz), 3.70-3.62 (3H, m), 3.22 (2H, q, J=5.2 Hz).

(Example 48) Potassium [(5-fluoro-2-methoxyphenyl) sulfonyl](5-oxo-2,3,4,5-tetrahydropyrido[3,2-f][1,4]oxazepin-7-yl)azanide (potassium salt of Example 10)

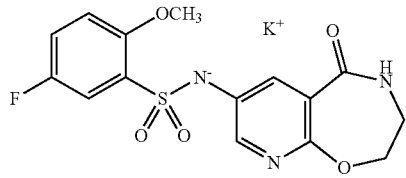 [SMILES: COc1ccc(F)cc1S(=O)(=O)[N-]c1cnc2c(c1)C(=O)NCCO2 ; [K+]]

(48a) N-[4-(2,4-Dimethoxybenzyl)-5-oxo-2,3,4,5-tetrahydropyrido[3,2-f][1,4]oxazepin-7-yl]-5-fluoro-2-methoxybenzenesulfonamide To a mixture of 7-amino-4-(2,4-dimethoxybenzyl)-3,4-dihydropyrido[3,2-f][1,4]oxazepin-5(2H)-one (3.83 g, 11.2 mmol) obtained in Example (8d) and pyridine (18.1 mL, 223 mmol), 5-fluoro-2-methoxybenzenesulfonyl chloride (2.76 g, 12.3 mmol) was added at room temperature, and the mixture was stirred at 80° C. for 1 hour in an oil bath. The reaction mixture was cooled to room temperature, diluted with water (90 mL) to precipitate a solid, and the suspension was stirred at room temperature for 1 hour. The precipitated solid was collected by filtration, and washed with water to obtain the crude solid. A suspension of the crude solid in ethanol (60 mL) was stirred at 80° C. for 1 hour in an oil bath. After cooling, the suspension was stirred in an ice water bath for 30 minutes. The precipitated solid was collected by filtration, washed with cold ethanol, and then dried to obtain the title compound (4.87 g, yield: 84%).

$^1$H NMR spectrum (DMSO-d6, 400 MHz) δ: 10.34 (1H, br s), 8.09 (1H, d, J=2.7 Hz), 7.97 (1H, t, J=2.7 Hz), 7.52-7.47 (2H, m), 7.26-7.23 (1H, m), 7.09 (1H, d, J=8.2 Hz), 6.58 (1H, d, J=2.7 Hz), 6.49 (1H, dd, J=8.2, 2.7 Hz), 4.57 (2H, s), 4.28 (2H, br t, J=4.7 Hz), 3.86 (3H, s), 3.77 (3H, s), 3.75 (3H, s), 3.53 (2H, br t, J=4.7 Hz).

(48b) 5-Fluoro-2-methoxy-N-(5-oxo-2,3,4,5-tetrahydropyrido[3,2-f][1,4]oxazepin-7-yl)benzenesulfonamide To a suspension of N-[4-(2,4-dimethoxybenzyl)-5-oxo-2,3,4,5-tetrahydropyrido[3,2-f][1,4]oxazepin-7-yl]-5-fluoro-2-methoxybenzenesulfonamide (4.86 g, 9.39 mmol) obtained in Example (48a) and anisole (2.04 mL, 18.8 mmol) in chloroform (45 mL), trifluoroacetic acid (14.4 mL, 188 mmol) and trifluoromethanesulfonic acid (1.65 mL, 18.8 mmol) were added at room temperature, and the mixture was stirred at room temperature for 30 minutes. The reaction mixture was carefully poured into a suspension of sodium bicarbonate (17.4 g, 207 mmol) in water (90 mL) at room temperature, and the mixture was stirred at room temperature for 10 minutes. Most of the organic solvents were distilled off under reduced pressure, the concentrated mixture was diluted by addition of ethyl acetate (90 mL), a precipitated solid was collected by filtration, and washed with water and ethyl acetate to obtain the crude solid. To a suspension of the crude solid in ethanol (50 mL), a 1 N aqueous solution of potassium hydroxide (10.3 mL, 10.3 mmol) was added at room temperature, and the mixture was stirred at room temperature for 10 minutes. The reaction mixture was filtered, and the residue on the filter paper was washed with water and ethanol. The filtrate and washings were combined, a 1 N hydrochloric acid (10.3 mL, 10.3 mmol) was added thereto, and the suspension was stirred in an ice water bath for 20 minutes. The precipitated solid was collected by filtration, washed with cold ethanol, and then dried to obtain the slightly crude solid. To a suspension of the slightly crude solid in ethanol (50 mL), a 1 N aqueous solution of potassium hydroxide (8.8 mL, 8.8 mmol) was added at room temperature, and the mixture was stirred at room temperature for 30 minutes. A 1 N hydrochloric acid (8.8 mL, 8.8 mmol) was added thereto, and the suspension was stirred at room temperature for 30 minutes. The precipitated solid was collected by filtration, washed with water and ethanol, and then dried to obtain the title compound (2.16 g, yield: 63%).

$^1$H NMR spectrum (DMSO-d6, 400 MHz) δ: 10.28 (1H, br s), 8.52 (1H, br t, J=4.9 Hz), 8.11-8.08 (2H, m), 7.51-7.46 (2H, m), 7.26-7.23 (1H, m), 4.36 (2H, t, J=4.3 Hz), 3.86 (3H, s), 3.40-3.35 (2H, m).

(48c) Potassium [(5-fluoro-2-methoxyphenyl)sulfonyl](5-oxo-2,3,4,5-tetrahydropyrido[3,2-f][1,4]oxazepin-7-yl)azanide To a suspension of 5-Fluoro-2-methoxy-N-(5-oxo-2,3,4,5-tetrahydropyrido[3,2-f][1,4]oxazepin-7-yl)benzenesulfonamide (1.950 g, 5.308 mmol) obtained in example (48b) in a mixed solvent of ethanol (53.5 mL) and water (0.478 mL), a solution of 0.5 N potassium hydroxide in ethanol (11.15 mL, 5.574 mmol) was added at room temperature, and the mixture was stirred at room temperature for 2 hours. The precipitated solid was collected by filtration, washed with ethanol and then dried to obtain the title compound (2.200 g, yield: quantitative).

¹H NMR spectrum (DMSO-d6, 400 MHz) δ: 8.19 (1H, br t, J=5.2 Hz), 7.72 (1H, d, J=2.7 Hz), 7.63 (1H, d, J=2.7 Hz), 7.41 (1H, dd, J=9.0, 3.1 Hz), 7.16-7.11 (1H, m), 6.98 (1H, dd, J=9.0, 4.3 Hz), 4.18 (2H, t, J=5.2 Hz), 3.65 (3H, s), 3.23 (2H, q, J=5.2 Hz).

(Example 49) Sodium [(5-fluoro-2-methoxyphenyl)sulfonyl](5-oxo-2,3,4,5-tetrahydropyrido[3,2-f][1,4]oxazepin-7-yl)azanide (sodium salt of Example 10)

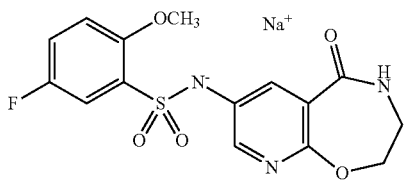 [SMILES: COc1ccc(F)cc1S(=O)(=O)[N-]c1cnc2c(c1)C(=O)NCCO2 ; [Na+]]

To a suspension of 5-Fluoro-2-methoxy-N-(5-oxo-2,3,4,5-tetrahydropyrido[3,2-f][1,4]oxazepin-7-yl)benzenesulfonamide (101.9 mg, 0.277 mmol) obtained in example (48b) in ethanol (2.7 mL), a 2 N aqueous solution of sodium hydroxide (0.138 mL, 0.277 mmol) was added at room temperature, and the mixture was stirred at room temperature for 30 minutes. The precipitated solid was collected by filtration, washed with ethanol and then dried to obtain the title compound (98.4 mg, yield: 91%).

¹H NMR spectrum (DMSO-d6, 400 MHz) δ: 8.20 (1H, br t, J=5.1 Hz), 7.71 (1H, d, J=2.7 Hz), 7.62 (1H, d, J=2.7 Hz), 7.41 (1H, dd, J=9.0, 3.1 Hz), 7.16-7.11 (1H, m), 6.97 (1H, dd, J=9.0, 4.3 Hz), 4.17 (2H, t, J=5.1 Hz), 3.66 (3H, s), 3.22 (2H, q, J=5.1 Hz).

(Example 50) Potassium {[5-chloro-2-(trifluoromethoxy)phenyl]sulfonyl}(5-oxo-2,3,4,5-tetrahydropyrido[3,2-f][1,4]oxazepin-7-yl)azanide (potassium salt of Example 13)

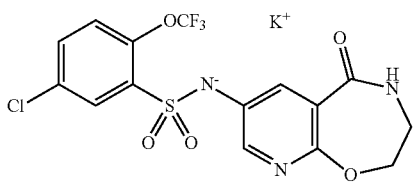 [SMILES: O=C1NCCOc2ncc([N-]S(=O)(=O)c3cc(Cl)ccc3OC(F)(F)F)cc21 ; [K+]]

The title compound (85.2 mg, yield: 78%) was obtained by production according to the method described in Example (47c) using 5-chloro-N-(5-oxo-2,3,4,5-tetrahydropyrido[3,2-f][1,4]oxazepin-7-yl)-2-(trifluoromethoxy)benzenesulfonamide (100 mg, 0.228 mmol) obtained in example (13c) and a solution of 0.5 N potassium hydroxide in ethanol (0.478 mL, 0.240 mmol).

¹H NMR spectrum (DMSO-d6, 400 MHz) δ: 8.22 (1H, br t, J=5.2 Hz), 7.78-7.73 (2H, m), 7.63-7.62 (1H, m), 7.53-7.51 (1H, m), 7.36-7.33 (1H, m), 4.19 (2H, t, J=5.2 Hz), 3.23 (2H, q, J=5.2 Hz).

(Example 51) Potassium [(5-chloro-2-methoxyphenyl)sulfonyl][(3S)-3-(hydroxymethyl)-5-oxo-2,3,4,5-tetrahydropyrido[3,2-f][1,4]oxazepin-7-yl]azanide (potassium salt of Example 27)

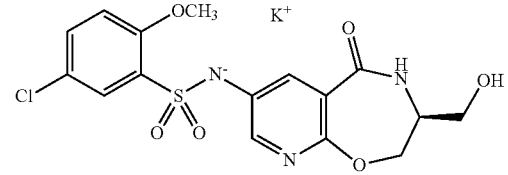 [SMILES: COc1ccc(Cl)cc1S(=O)(=O)[N-]c1cnc2c(c1)C(=O)N[C@@H](CO)CO2 ; [K+]]

The title compound (124.1 mg, yield: 94%) was obtained by production according to the method described in Example (47c) using 5-chloro-N-[(3S)-3-(hydroxymethyl)-5-oxo-2,3,4,5-tetrahydropyrido[3,2-f][1,4]oxazepin-7-yl]-2-methoxybenzenesulfonamide (121.3 mg, 0.293 mmol) obtained in Example (27f) and a solution of 0.5 N potassium hydroxide in ethanol (0.962 mL, 0.482 mmol).

¹H NMR spectrum (DMSO-d6, 400 MHz) δ: 7.93 (1H, br s), 7.77 (1H, d, J=2.7 Hz), 7.70 (1H, d, J=2.7 Hz), 7.64 (1H, d, J=2.7 Hz), 7.34 (1H, dd, J=8.6, 2.7 Hz), 6.99 (1H, d, J=8.6 Hz), 4.92 (1H, br t, J=5.7 Hz), 4.20-4.12 (2H, m), 3.66 (3H, s), 3.46-3.41 (3H, m).

(Example 52) Potassium [(5-fluoro-2-methoxyphenyl)sulfonyl][(3S)-3-(hydroxymethyl)-5-oxo-2,3,4,5-tetrahydropyrido[3,2-f][1,4]oxazepin-7-yl]azanide (potassium salt of Example 28)

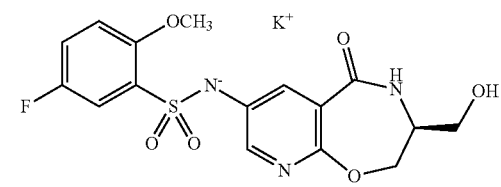 [SMILES: COc1ccc(F)cc1S(=O)(=O)[N-]c1cnc2c(c1)C(=O)N[C@@H](CO)CO2 ; [K+]]

The title compound (78.7 mg, yield: 84%) was obtained by production according to the method described in Examples (47c) using 5-fluoro-N-[(3S)-3-(hydroxymethyl)-5-oxo-2,3,4,5-tetrahydropyrido[3,2-f][1,4] oxazepin-7-yl]-2-methoxybenzenesulfonamide (75.5 mg, 0.190 mmol) obtained in Example (28b) and a solution of 0.5 N potassium hydroxide in ethanol (0.386 mL, 0.194 mmol).

¹H NMR spectrum (DMSO-d6, 400 MHz) δ: 7.92 (1H, br s), 7.77 (1H, br s), 7.71 (1H, d, J=2.7 Hz), 7.41 (1H, dd, J=9.0, 3.1 Hz), 7.16-7.11 (1H, m), 6.97 (1H, dd, J=9.0, 4.3 Hz), 4.91 (1H, t, J=5.5 Hz), 4.20-4.12 (2H, m), 3.65 (3H, s), 3.46-3.40 (3H, m).

(Example 53) Potassium [(5-bromo-2-methoxyphenyl)sulfonyl][(3S)-3-(hydroxymethyl)-5-oxo-2,3,4,5-tetrahydropyrido[3,2-f][1,4]oxazepin-7-yl]azanide (potassium salt of Example 29)

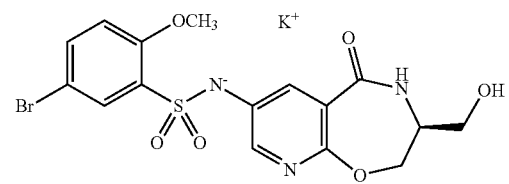 [SMILES: O=C1N[C@@H](CO)COc2ncc([N-]S(=O)(=O)c3cc(Cl)ccc3OC(F)(F)F)cc21 ; [K+]]

The title compound (92.7 mg, yield: 82%) was obtained by production according to the method described in Example (47c) using 5-bromo-N-[(3S)-3-(hydroxymethyl)-5-oxo-2,3,4,5-tetrahydropyrido[3,2-f][1,4]oxazepin-7-yl]-2-methoxybenzenesulfonamide (104.4 mg, 0.228 mmol) obtained in Example (29b) and a solution of 0.5 N potassium hydroxide in ethanol (0.451 mL, 0.228 mmol).

$^1$H NMR spectrum (DMSO-d6, 400 MHz) δ: 7.93 (1H, br d, J=3.5 Hz), 7.78-7.75 (2H, m), 7.68 (1H, d, J=2.7 Hz), 7.44 (1H, dd, J=9.0, 2.7 Hz), 6.93 (1H, d, J=9.0 Hz), 4.92 (1H, t, J=5.5 Hz), 4.20-4.14 (2H, m), 3.63 (3H, s), 3.46-3.41 (3H, m).

(Example 54) Potassium {[5-chloro-2-(trifluoromethoxy)phenyl]sulfonyl}[(3S)-3-(hydroxymethyl)-5-oxo-2,3,4,5-tetrahydropyrido[3,2-f][1,4]oxazepin-7-yl]azanide (potassium salt of Example 31)

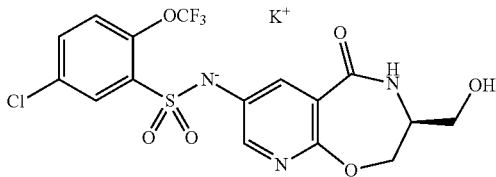

The title compound (44 mg, yield: 58%) was obtained by production according to the method described in Example (47c) using 5-chloro-N-[(3S)-3-(hydroxymethyl)-5-oxo-2,3,4,5-tetrahydropyrido[3,2-f][1,4]oxazepin-7-yl]-2-(trifluoromethoxy)benzenesulfonamide (70 mg, 0.15 mmol) obtained in Example (31b) and a solution of 0.5 N potassium hydroxide in ethanol (0.31 mL, 0.16 mmol).

$^1$H NMR spectrum (DMSO-d6, 400 MHz) δ: 7.96 (1H, br d, J=3.5 Hz), 7.78 (1H, d, J=2.7 Hz), 7.77 (1H, d, J=2.7 Hz), 7.72 (1H, d, J=2.7 Hz), 7.51 (1H, dd, J=8.6, 2.7 Hz), 7.34-7.32 (1H, m), 4.95-4.92 (1H, m), 4.21-4.14 (2H, m), 3.43-3.39 (3H, m).

(Example 55) Potassium [(5-chloro-2-methoxyphenyl) sulfonyl](5'-oxo-4',5'-dihydrospiro[cyclopropane-1,3'-pyrido[3,2-f][1,4]oxazepin]-7'-yl)azanide (potassium salt of Example 35)

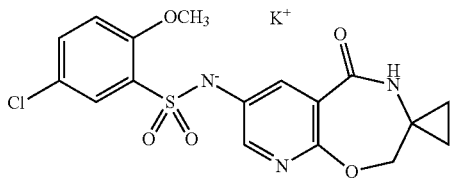 [SMILES: COc1ccc(Cl)cc1S(=O)(=O)[N-]c1cnc2c(c1)C(=O)NC1(CC1)CO2 ; [K+]]

(55a) 5-Chloro-N-[4'-(2,4-dimethoxybenzyl)-5'-oxo-4',5'-dihydrospiro[cyclopropane-1,3'-pyrido[3,2-f][1,4]oxazepin]-7'-yl]-2-methoxybenzenesulfonamide To a mixture of 7'-amino-4'-(2,4-dimethoxybenzyl)spiro[cyclopropane-1,3'-pyrido[3,2-f][1,4]oxazepin]-5'(4'H)-one (0.9040 g, 2.54 mmol) obtained in Example (35d) and pyridine (4.1 mL, 51 mmol), 5-chloro-2-methoxybenzenesulfonyl chloride (0.6450 g, 2.68 mmol) was added at room temperature, and the mixture was stirred at 80° C. for 20 minutes in an oil bath. The reaction mixture was cooled and then concentrated under reduced pressure, and the residue was diluted with water, followed by extraction with ethyl acetate. The organic layer was washed with water and a saturated aqueous solution of sodium chloride, and anhydrous magnesium sulfate and charcoal were added thereto. After filtration through pad of Celite 545 (R), the solvent was distilled off under reduced pressure. To the residue, diisopropyl ether (7 mL) and ethyl acetate (7 mL) were added to precipitate a solid. The suspension was stirred at room temperature for 30 minutes. The precipitated solid was collected by filtration, washed with diisopropyl ether, and then dried to obtain the title compound (1.3007 g, yield: 92%).

$^1$H NMR spectrum (CDCl$_3$, 400 MHz) δ: 8.20 (1H, d, J=2.7 Hz), 7.84 (1H, d, J=2.7 Hz), 7.73 (1H, d, J=2.7 Hz), 7.47 (1H, dd, J=9.0, 2.7 Hz), 7.16-7.14 (1H, m), 7.02-6.99 (2H, m), 6.46-6.43 (2H, m), 4.66 (2H, br s), 4.06 (3H, s), 3.93 (2H, br s), 3.81 (3H, s), 3.79 (3H, s), 0.88 (2H, br s), 0.64 (2H, br s).

(55b) 5-Chloro-2-methoxy-N-(5'-oxo-4',5'-dihydrospiro[cyclopropane-1,3'-pyrido[3,2-f][1,4]oxazepin]-7'-yl)benzenesulfonamide To a mixture of 5-chloro-N-[4'-(2,4-dimethoxybenzyl)-5'-oxo-4',5'-dihydrospiro[cyclopropane-1,3'-pyrido[3,2-f][1,4]oxazepin]-7'-yl]-2-methoxybenzenesulfonamide (1.2938 g, 2.31 mmol) obtained in Example (55a) and anisole (0.51 mL, 4.7 mmol) in chloroform (11.5 mL), trifluoroacetic acid (3.60 mL, 47.0 mmol) and trifluoromethanesulfonic acid (0.41 mL, 4.7 mmol) were added under ice cooling, and the mixture was stirred at the same temperature as above for 3 hours and subsequently stirred at room temperature for 5 hours. The reaction mixture was carefully poured into a suspension of sodium bicarbonate (3.88 g, 46.2 mmol) in water (11.5 mL) at room temperature, and the mixture was stirred at room temperature for 1 hour. Most of the organic solvents were distilled off under reduced pressure, the concentrated mixture was diluted by addition of water (30 mL) and ethyl acetate (30 mL), a precipitated solid was collected by filtration, and washed with water and ethyl acetate to obtain the crude solid. To a suspension of the crude solid in a mixed solvent of ethanol (11.5 mL) and water (11.5 mL), a 1 N aqueous solution of potassium hydroxide (3.45 mL, 3.48 mmol) was added at room temperature, and the mixture was stirred at room temperature for 10 minutes. After filtration, a 2 N hydrochloric acid (1.74 mL, 3.49 mmol) was added to the filtrate, and the precipitated solid was collected by filtration, washed with water and ethanol, and then dried to obtain the title compound (0.6970 g, yield: 74%).

$^1$H NMR spectrum (DMSO-d6, 400 MHz) δ: 10.29 (1H, br s), 8.84 (1H, br s), 8.08 (1H, d, J=3.1 Hz), 7.95 (1H, d, J=3.1 Hz), 7.67 (1H, dd, J=9.0, 2.7 Hz), 7.63 (1H, d, J=2.7 Hz), 7.25 (1H, d, J=9.0 Hz), 4.26 (2H, s), 3.88 (3H, s), 0.75-0.73 (4H, m).

(55c) Potassium [(5-chloro-2-methoxyphenyl)sulfonyl](5'-oxo-4',5'-dihydrospiro[cyclopropane-1,3'-pyrido[3,2-f][1,4]oxazepin]-7'-yl)azanide To a suspension of 5-chloro-2-methoxy-N-(5'-oxo-4',5'-dihydrospiro[cyclopropane-1,3'-pyrido[3,2-f][1,4]oxazepin]-7'-yl)benzenesulfonamide (40.0 mg, 0.098 mmol) obtained in Example (55b) in ethanol (2 mL), a solution of 0.5 N potassium hydroxide in ethanol (0.195 mL, 0.098 mmol) was added at room temperature, and the mixture was stirred at room temperature for 2 hours. The mixture was concentrated under reduced pressure, acetone (1 mL) was added thereto, the precipitated solid was collected by filtration, washed with acetone, and then dried to obtain the title compound (42 mg, yield: 96%).

$^1$H NMR spectrum (DMSO-d6, 400 MHz) δ: 8.48 (1H, br s), 7.68 (1H, d, J=2.7 Hz), 7.61 (1H, d, J=2.7 Hz), 7.54 (1H, d, J=2.7 Hz), 7.32 (1H, dd, J=8.6, 2.7 Hz), 6.98 (1H, d, J=8.6 Hz), 4.07 (2H, s), 3.65 (3H, s), 0.68-0.60 (4H, m).

(Example 56) Sodium [(5-chloro-2-methoxyphenyl)sulfonyl](5'-oxo-4',5'-dihydrospiro[cyclopropane-1,3'-pyrido[3,2-f][1,4]oxazepin]-7'-yl)azanide (sodium salt of Example 35)

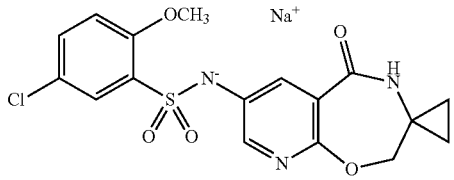 [SMILES: COc1ccc(Cl)cc1S(=O)(=O)[N-]c1cnc2c(c1)C(=O)NC1(CC1)CO2 ; [Na+]]

To a suspension of 5-chloro-2-methoxy-N-(5'-oxo-4',5'-dihydrospiro[cyclopropane-1,3'-pyrido[3,2-f][1,4]oxazepin]-7'-yl)benzenesulfonamide (95.2 mg, 0.232 mmol) obtained in Example (55b) in ethanol (2.3 mL), a 2 N aqueous solution of sodium hydroxide (0.116 mL, 0.233 mmol) was added at room temperature, and the mixture was stirred at room temperature for 15 minutes. The mixture was concentrated under reduced pressure, acetone (2.3 mL) was added thereto, the precipitated solid was collected by filtration, washed with acetone, and then dried to obtain the title compound (106.2 mg, yield: quantitative).

$^1$H NMR spectrum (DMSO-d6, 400 MHz) δ: 8.49 (1H, br s), 7.69 (1H, d, J=2.7 Hz), 7.62 (1H, d, J=2.7 Hz), 7.55 (1H, d, J=2.7 Hz), 7.33 (1H, dd, J=8.6, 2.7 Hz), 6.99 (1H, d, J=8.6 Hz), 4.07 (2H, s), 3.67 (3H, s), 0.67-0.60 (4H, m).

(Example 57) Potassium [(5-fluoro-2-methoxyphenyl) sulfonyl](5'-oxo-4',5'-dihydrospiro[cyclopropane-1,3'-pyrido[3,2-f][1,4]oxazepin]-7'-yl)azanide (potassium salt of Example 36)

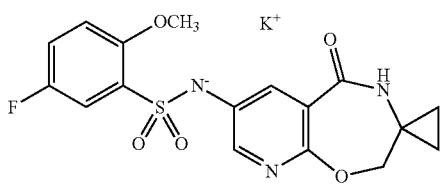

The title compound (41 mg, yield: 94%) was obtained by production according to the method described in Example (47c) using 5-fluoro-2-methoxy-N-(5'-oxo-4',5'-dihydrospiro[cyclopropane-1,3'-pyrido[3,2-f][1,4]oxazepin]-7'-yl)benzenesulfonamide (40.0 mg, 0.102 mmol) obtained in Example 36 and a solution of 0.5 N potassium hydroxide in ethanol (0.203 mL, 0.102 mmol).

$^1$H NMR spectrum (DMSO-d6, 400 MHz) δ: 8.48 (1H, br s), 7.68 (1H, d, J=2.7 Hz), 7.55 (1H, d, J=2.7 Hz), 7.39 (1H, dd, J=9.0, 3.1 Hz), 7.15-7.10 (1H, m), 6.96 (1H, dd, J=9.0, 4.3 Hz), 4.06 (2H, br s), 3.64 (3H, br s), 0.66-0.61 (4H, m).

(Example 58) Potassium {[5-chloro-2-(trifluoromethoxy)phenyl]sulfonyl}(5'-oxo-4',5'-dihydrospiro[cyclopropane-1,3'-pyrido[3,2-f][1,4]oxazepin]-7'-yl)azanide (potassium salt of Example 40)

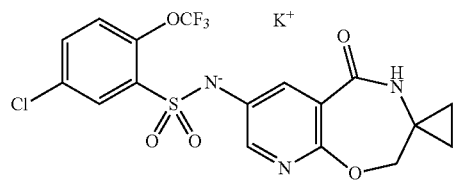 [SMILES: O=C1NC2(CC2)COc2ncc([N-]S(=O)(=O)c3cc(Cl)ccc3OC(F)(F)F)cc21 ; [K+]]

The title compound (63 mg, yield: 94%) was obtained by production according to the method described in Example (47c) using 5-chloro-N-(5'-oxo-4',5'-dihydrospiro[cyclopropane-1,3'-pyrido[3,2-f][1,4]oxazepin]-7'-yl)-2-(trifluoromethoxy)benzenesulfonamide (62.0 mg, 0.134 mmol) obtained in Example (40c) and a solution of 0.5 N potassium hydroxide in ethanol (0.267 mL, 0.134 mmol).

$^1$H NMR spectrum (DMSO-d6, 400 MHz) δ: 8.51 (1H, br s), 7.76-7.72 (2H, m), 7.56-7.51 (2H, m), 7.35 (1H, d, J=9.0 Hz), 4.08 (2H, br s), 0.65-0.63 (4H, m).

(Example 59) Potassium (2-ethoxy-5-fluorophenyl) sulfonyl](5'-oxo-4',5'-dihydrospiro[cyclopropane-1,3'-pyrido[3,2-f][1,4]oxazepin]-7'-yl)azanide (potassium salt of Example 42)

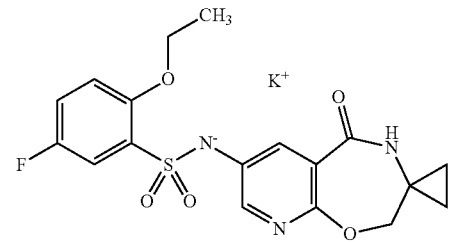 [SMILES: CCOc1ccc(F)cc1S(=O)(=O)[N-]c1cnc2c(c1)C(=O)NC1(CC1)CO2 ; [K+]]

(59a) N-[4'-(2,4-Dimethoxybenzyl)-5'-oxo-4',5'-dihydrospiro[cyclopropane-1,3'-pyrido[3,2-f][1,4]oxazepin]-7'-yl]-2-ethoxy-5-fluorobenzenesulfonamide To a mixture of 7'-amino-4'-(2,4-dimethoxybenzyl)spiro [cyclopropane-1,3'-pyrido[3,2-f][1,4]oxazepin]-5'(4'H)-one (0.9073 g, 2.55 mmol) obtained in Example (35d) and pyridine (4.1 mL, 51 mmol), 5-fluoro-2-ethoxybenzenesulfonyl chloride (0.6401 g, 2.68 mmol) obtained in Example (42a) was added at room temperature, and the mixture was stirred at 80° C. for 20 minutes in an oil bath. The reaction mixture was cooled and then concentrated under reduced pressure, and the residue was diluted with water (50 mL) and ethyl acetate (50 mL), the aqueous layer was separated off, the organic layer was diluted with tetrahydrofuran (150 mL), and anhydrous magnesium sulfate and charcoal were added thereto. After filtration through pad of Celite 545 (R), the solvent was distilled off under reduced pressure. To the residue, ethyl acetate (14 mL) was added to precipitate a solid, and the suspension was stirred at room temperature for 1 hour. The precipitated solid was collected by filtration, washed with ethyl acetate, and then dried to obtain the title compound (1.2525 g, yield: 88%).

$^1$H NMR spectrum (CDCl$_3$, 400 MHz) δ: 8.20 (1H, d, J=2.7 Hz), 7.85 (1H, d, J=2.7 Hz), 7.47 (1H, dd, J=7.4, 3.1 Hz), 7.23-7.14 (2H, m), 7.02-6.95 (2H, m), 6.46-6.43 (2H, m), 4.66 (2H, br s), 4.29 (2H, q, J=7.0 Hz), 3.92 (2H, br s), 3.80 (3H, s), 3.79 (3H, s), 1.58 (3H, t, J=7.0 Hz), 0.87 (2H, br s), 0.63 (2H, br s).

(59b) 2-Ethoxy-5-fluoro-N-(5'-oxo-4',5'-dihydrospiro[cyclopropane-1,3'-pyrido[3,2-f][1,4]oxazepin]-7'-yl)benzenesulfonamide To a mixture of N-[4'-(2,4-dimethoxybenzyl)-5'-oxo-4',5'-dihydrospiro[cyclopropane-1,3'-pyrido[3,2-f][1,4]oxazepin]-7'-yl]-2-ethoxy-5-fluorobenzenesulfonamide (1.2658 g, 2.27 mmol) obtained in Example (59a) and anisole (0.50 mL, 4.6 mmol) in chloroform (11.5 mL), trifluoroacetic acid (3.45 mL, 45.1 mmol) and trifluoromethanesulfonic acid (0.40 mL, 4.0 mmol) were added under ice cooling, and the mixture was stirred at the same temperature as above for 30 minutes and subsequently stirred at room temperature for 5 hours. The reaction mixture was carefully poured into a suspension of sodium bicarbonate (3.82 g, 45.5 mmol) in water (11.5 mL) at room temperature, isopropyl alcohol (5 mL) was added thereto, and the mixture was stirred at room temperature for 20 minutes. Most of the organic solvents were distilled off under reduced pressure, the concentrated mixture was diluted by addition of water (50 mL) followed by extraction with a mixed solvent of ethyl acetate (100 mL) and tetrahydrofuran (50 mL). The organic layer was washed with a saturated aqueous solution of sodium chloride, and anhydrous magnesium sulfate and charcoal were added thereto. After filtration through pad of Celite 545 (R), the solvent was distilled off under reduced pressure. To the residue, ethyl acetate (12 mL) was added to precipitate a solid, and the suspension was stirred at room temperature for 30 minutes. The precipitated solid was collected by filtration, washed with ethyl acetate, and then dried to obtain the title compound (0.7940 g, yield: 86%).

$^1$H NMR spectrum (DMSO-d6, 400 MHz) δ: 10.15 (1H, s), 8.83 (1H, s), 8.09 (1H, d, J=2.7 Hz), 7.95 (1H, d, J=2.7 Hz), 7.52-7.44 (2H, m), 7.24 (1H, dd, J=9.0, 4.3 Hz), 4.26 (br 2H, s), 4.16 (2H, q, J=7.0 Hz), 1.26 (3H, t, J=7.0 Hz), 0.77-0.71 (4H, m).

(59c) Potassium [(2-ethoxy-5-fluorophenyl)sulfonyl](5'-oxo-4',5'-dihydrospiro[cyclopropane-1,3'-pyrido[3,2-f][1,4]oxazepin]-7'-yl)azanide To a suspension of 2-ethoxy-5-fluoro-N-(5'-oxo-4',5'-dihydrospiro[cyclopropane-1,3'-pyrido[3,2-f][1,4]oxazepin]-7'-yl)benzenesulfonamide (70.0 mg, 0.172 mmol) obtained in example (59b) in ethanol (5 mL), a solution of 0.5 N potassium hydroxide in ethanol (0.343 mL, 0.172 mmol) was added at room temperature, and the mixture was stirred at room temperature for 3 hours. The solvent was distillated off under reduce pressure to obtain the title compound (77 mg, yield: quantitative).

$^1$H NMR spectrum (DMSO-d6, 400 MHz) δ: 8.45 (1H, br s), 7.70 (1H, d, J=2.7 Hz), 7.54 (1H, d, J=2.7 Hz), 7.41 (1H, dd, J=9.0, 3.1 Hz), 7.11-7.06 (1H, m), 6.95 (1H, dd, J=9.0, 4.3 Hz), 4.06 (2H, s), 3.93 (2H, q, J=6.9 Hz), 1.12 (3H, t, J=6.9 Hz), 0.67-0.59 (4H, m).

(Example 60) Sodium [(2-ethoxy-5-fluorophenyl)sulfonyl](5'-oxo-4',5'-dihydrospiro[cyclopropane-1,3'-pyrido[3,2-f][1,4]oxazepin]-7'-yl)azanide (sodium salt of Example 42)

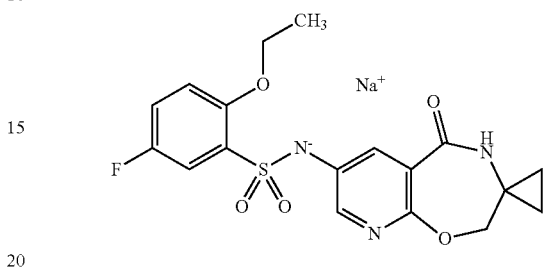

To a suspension of 2-ethoxy-5-fluoro-N-(5'-oxo-4',5'-dihydrospiro[cyclopropane-1,3'-pyrido[3,2-f][1,4]oxazepin]-7'-yl)benzenesulfonamide (97.3 mg, 0.239 mmol) obtained in example (59b) in ethanol (2.4 mL), a 2 N aqueous solution of sodium hydroxide (0.119 mL, 0.239 mmol) was added at room temperature, and the mixture was stirred at room temperature for 15 minutes. The mixture was concentrated under reduced pressure, acetone (2.4 mL) was added thereto, the precipitated solid was collected by filtration, washed with acetone, and then dried to obtain the title compound (104.1 mg, yield: quantitative).

$^1$H NMR spectrum (DMSO-d6, 400 MHz) δ: 8.47 (1H, br s), 7.71 (1H, d, J=2.7 Hz), 7.55 (1H, d, J=2.7 Hz), 7.41 (1H, dd, J=9.0, 3.1 Hz), 7.13-7.07 (1H, m), 6.96 (1H, dd, J=9.0, 4.3 Hz), 4.06 (2H, s), 3.94 (2H, q, J=7.0 Hz), 1.13 (3H, t, J=7.0 Hz), 0.66-0.59 (4H, m).

(Example 61) Potassium [(2,5-dimethoxyphenyl)sulfonyl](5'-oxo-4',5'-dihydrospiro[cyclopropane-1,3'-pyrido[3,2-f][1,4]oxazepin]-7'-yl)azanide (potassium salt of Example 43)

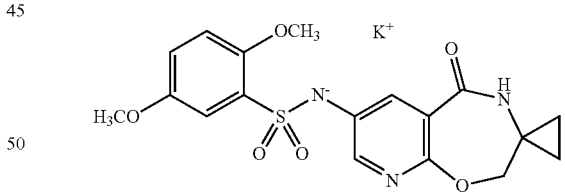

To a suspension of 2,5-dimethoxy-N-(5'-oxo-4',5'-dihydrospiro[cyclopropane-1,3'-pyrido[3,2-f][1,4]oxazepin]-7'-yl)benzenesulfonamide (43.0 mg, 0.106 mmol) obtained in Example (43b) in ethanol (5 mL), a solution of 0.5 N potassium hydroxide in ethanol (0.211 mL, 0.106 mmol) was added at room temperature, and the mixture was stirred at room temperature for 2 hours. The solvent was distilled off under reduce pressure to obtain the title compound (51 mg, yield: quantitative).

$^1$H NMR spectrum (DMSO-d6, 400 MHz) δ: 8.47 (1H, br s), 7.68 (1H, d, J=2.7 Hz), 7.55 (1H, d, J=2.7 Hz), 7.29 (1H, d, J=3.1 Hz), 6.89 (1H, d, J=8.6 Hz), 6.84 (1H, dd, J=8.6, 3.1 Hz), 4.05 (2H, br s), 3.66 (3H, s), 3.63 (3H, s), 0.67-0.57 (4H, m).

TEST EXAMPLES (Test Example 1) Inhibitory Test of TNAP Activity

COS1 cells (DS Pharma Biomedical Co., Ltd.) were transfected with human TNAP (OriGene Technologies, Inc.) using Lipofectamine LTX & Plus reagent (Invitrogen Corp.). On the next day, the medium was replaced with a fresh medium, and the cells were cultured in an incubator for 3 days. After 3 days, the culture supernatant was collected and concentrated by centrifugation at 5000 G for 30 minutes using Amicon 14, $10^4$ cut (Merck Millipore). The concentrated culture supernatant was dialyzed against 5 L of 50 mM Tris/200 mM NaCl/1 mM $MgCl_2$/20 µM $ZnCl_2$ twice and used as an enzyme source (enzyme solution). The substrate pNPP (ProteoChem Inc.) was adjusted to 3.1 mM with Milli-Q water, and a solution of each test compound dissolved in dimethyl sulfoxide (DMSO; Wako Pure Chemical Industries, Ltd.) by 6 serial dilutions at a 5-fold common ratio from 100 µM, or DMSO was added thereto at a final concentration of 1% by volume. The enzyme solution adjusted to 2 µg/mL with an assay buffer (200 mM Tris/2 mM $MgCl_2$/0.04 mM $ZnCl_2$/0.01% Tween 20) was added in the same amount of the substrate solution and incubated at room temperature for 60 minutes. Then, the absorbance (ABS: 405 nm) was measured using a microplate reader (model plus 384, Molecular Devices, LLC), and the concentration of produced p-nitrophenol was calculated. The inhibition of human TNAP activity by the test compound was evaluated on the basis of the concentration $IC_{50}$ at which each test compound suppressed 50% of p-nitrophenol production.

The results are shown in Table 1. [Table 1]

TABLE 1

| Example compound No. | $IC_{50}$ (nM) |
| --- | --- |
| 1 | 6.3 |
| 2 | 12.7 |
| 3 | 12.8 |
| 4 | 22.9 |
| 5 | 71.3 |
| 6 | 6.1 |
| 7 | 10.7 |
| 8 | 9.1 |
| 9 | 1.4 |
| 10 | 4.0 |
| 11 | 4.8 |
| 12 | 13.4 |
| 13 | 3.4 |
| 14 | 36.2 |
| 15 | 95.7 |
| 16 | 6.2 |
| 17 | 12.6 |
| 18 | 3.9 |
| 19 | 6.4 |
| 20 | 27.1 |
| 21 | 46.0 |
| 22 | 1.7 |
| 23 | 3.5 |
| 24 | 7.2 |
| 25 | 1.7 |
| 26 | 8.7 |
| 27 | 1.5 |
| 28 | 3.6 |
| 29 | 1.2 |
| 30 | 3.8 |
| 31 | 1.6 |
| 32 | 4.1 |
| 33 | 1.9 |
| 34 | 6.7 |
| 35 | 1.1 |

TABLE 1-continued

| Example compound No. | $IC_{50}$ (nM) |
| --- | --- |
| 36 | 2.2 |
| 37 | 43.4 |
| 38 | 24.4 |
| 39 | 13.2 |
| 40 | 1.9 |
| 41 | 2.7 |
| 42 | 0.6 |
| 43 | 1.0 |
| 44 | 1.4 |
| 45 | 14.6 |
| 46 | 25.2 |

The compound of the present invention exhibits the excellent inhibition of human TNAP activity and is useful as a pharmaceutical agent for the treatment or prophylaxis of ectopic calcification.

(Test Example 2) Specific Inhibitory Test of TNAP Activity

COS1 cells (DS Pharma Biomedical Co., Ltd.) were transfected with human IAP (small-intestinal alkaline phosphatase, purchased from OriGene Technologies, Inc.) or human PLAP (placental alkaline phosphatase, purchased from OriGene Technologies, Inc.) using Lipofectamine LTX & Plus reagent (Invitrogen Corp.). On the next day, the medium was replaced with a fresh medium, and the cells were cultured in an incubator for 3 days. After 3 days, the culture supernatant was collected and concentrated by centrifugation at 5000 G for 30 minutes using Amicon 14, $10^4$ cut (Merck Millipore). The concentrated culture supernatant was dialyzed against 5 L of 50 mM Tris/200 mM NaCl/1 mM $MgCl_2$/20 µM $ZnCl_2$ twice and used as an enzyme source (enzyme solution). The substrate pNPP (ProteoChem Inc.) was adjusted to 3.1 mM with Milli-Q water, and a solution of each test compound dissolved in dimethyl sulfoxide (DMSO; Wako Pure Chemical Industries, Ltd.) by 6 serial dilutions at a 5-fold common ratio from 100 µM, or DMSO was added thereto at a final concentration of 1% by volume. The enzyme solution of human IAP or human PLAP adjusted to 2 µg/mL with an assay buffer (200 mM Tris/2 mM $MgCl_2$/0.04 mM $ZnCl_2$/0.01% Tween 20) was added in the same amount of the substrate solution and incubated at room temperature for 60 minutes. Then, the absorbance (ABS: 405 nm) was measured using a microplate reader (model plus 384, Molecular Devices, LLC), and the concentration of produced p-nitrophenol was calculated. The inhibition of human IAP or PLAP activity by the test compound was evaluated on the basis of the concentration $IC_{50}$ at which each test compound suppressed 50% of p-nitrophenol production.

The compound of the present invention exhibits the excellent specific inhibition of TNAP activity and is useful as a pharmaceutical drug for the treatment or prevention of ectopic calcification.

(Test Example 3) Inhibitory Test of Plasma TNAP Activity in B6 Mouse (Charles River Laboratories Japan, Inc.)

After blood sampling from the tail vein using a heparin-treated hematocrit capillary tube (EM Meister Hematocrit Capillary Tube, AS ONE Corp.) (as the sample before compound administration), each test compound suspended in a 0.5% methylcellulose solution (powder purchased from Wako Pure Chemical Industries, Ltd. was adjusted to 0.5% with Otsuka distilled water) was administered orally to the mouse. 1, 2, 4, 6, and 24 hours after the administration, blood was collected from the tail vein using a heparin-treated hematocrit capillary tube to obtain a plasma sample. The plasma sample was added to an assay buffer (1 M Tris, 1 M $MgCl_2$, 20 mM $ZnCl_2$, and water, pH 7.5), and the mixture was left standing for 5 minutes. Then, the absorbance at 405 nm was measured and used as a blank. The substrate pNPP was added to the plasma sample and incubated at room temperature for 180 minutes. Then, the absorbance (ABS: 405 nm) was measured using a microplate reader (model plus 384, Molecular Devices, LLC), and the concentration of produced p-nitrophenol was calculated. The blank was subtracted from all measurement values to calculate TNAP activity at each time point with the TNAP activity of the sample before compound administration defined as 100%. The pharmaceutical effect of the test compound was evaluated by the average inhibition of plasma ALP (80-90% containing TNAP) activity for 6 hours from 0 hour to 6 hours after the administration of the test compound. It was calculated according to the following expression: 100−((plasma ALP activity at 0 hr+plasma ALP activity at 1 hr)*½+(plasma ALP activity at 1 hr+plasma ALP activity at 2 hr)*½+(plasma ALP activity at 2 hr+plasma ALP activity at 4 hr)*2/2+(plasma ALP activity at 4 hr+plasma ALP activity at 6 hr)*2/2)/6.

The results are shown in Table 2.

TABLE 2

| Example compound No. | Plasma ALP inhibition (6h ave. inhibition %) |
|---|---|
| 47 | 54.7 |
| 48 | 61.6 |
| 50 | 56.0 |
| 51 | 63.7 |
| 52 | 61.3 |
| 53 | 59.2 |
| 54 | 74.8 |
| 55 | 58.9 |
| 57 | 53.5 |
| 58 | 50.3 |
| 59 | 66.2 |
| 61 | 67.5 |

The compound of the present invention exhibits an excellent in vivo TNAP inhibitory effect and is useful as a pharmaceutical agent for the treatment or prophylaxis of ectopic calcification.

(Test Example 4) In Vivo Anti-Calcification Test in Vitamin D-Induced Calcification Model A DBA/2 mouse (male, 6 weeks old when used, Charles River Laboratories Japan, Inc.) was given powder feed (FR-2 powder feed, Funabashi Farm Co., Ltd.) containing each test compound. 3.75 mg/kg cholecalciferol (Sigma-Aldrich Corp.) was intraperitoneally administered for 3 days from the next day. Seven days after the final cholecalciferol administration, the animal was sacrificed, and the thoracic aorta and the kidney were sampled. The tissue samples were freeze-dried (FREEZE DRYER, FRD-50M, Iwaki Asahi Techno Glass Corp.). Then, 10% formic acid (undiluted solution purchased from Kishida Chemical Co., Ltd. was adjusted to 10% with Milli-Q water) was added to each tissue sample, which was then homogenized using QIAGEN Retsch MM300 TissueLyser (Qiagen N.V.). The homogenate was centrifuged, and the supernatant was used as a sample. The calcium concentration in the sample was measured as absorbance (ABS 612 nm, Microplate reader, model plus 384, Molecular Devices, LLC) using Calcium assay kit (Wako Pure Chemical Industries, Ltd.) to calculate the amount of calcium in the tissue.

The compound of the present invention exhibits an excellent anti-calcification effect and is useful as a therapeutic agent for the treatment or prevention of ectopic calcification.

(Test Example 5) In Vivo Anti-Calcification Test in Nephrectomized Mouse

A 5/6 nephrectomized DBA/2 mouse (male, 8 weeks old) was purchased from CLEA Japan, Inc. This mouse was loaded with 1.2% high-phosphorus diet (Oriental Yeast Co., Ltd.). Each test compound suspended in a 0.5% methylcellulose solution (powder purchased from Wako Pure Chemical Industries, Ltd. was adjusted to 0.5% with Otsuka distilled water) was administered orally twice daily for three months. After three months, the animal was sacrificed, and the kidney was sampled. The tissue sample was freeze-dried (FREEZE DRYER, FRD-50M, Iwaki Asahi Techno Glass Corp.). Then, 10% formic acid (undiluted solution purchased from Kishida Chemical Co., Ltd. was adjusted to 10% with Milli-Q water) was added to the tissue sample, which was then homogenized using QIAGEN Retsch MM300 TissueLyser (Qiagen N.V.). The homogenate was centrifuged, and the supernatant was used as a sample. The calcium concentration in the sample was measured as absorbance (ABS 612 nm, Microplate reader, model plus 384, Molecular Devices, LLC) using Calcium assay kit (Wako Pure Chemical Industries, Ltd.) to calculate the amount of calcium in the tissue.

The compound of the present invention exhibits an excellent anti-calcification effect and is useful as a pharmaceutical drug for the treatment or prophylaxis of ectopic calcification.

(Test Example 6) Pharmacokinetic Test

The pharmacokinetic test can be conducted according to a method well-known in the field of pharmacodynamics.

Each test compound was suspended in a 0.5% aqueous methylcellulose solution. The obtained suspension was orally administered at a dose in an appropriate range (e.g., 0.01 mg/kg to 10 mg/kg) to an animal (e.g., a mouse, a rat, a dog, or a cynomolgus monkey) generally used in the pharmacokinetic test. Also, the test compound was dissolved in saline. The obtained solution was intravenously (e.g., through the tail vein, the cephalic vein, or the saphenous vein) administered at a dose in an appropriate range (e.g., 0.1 mg/kg to 10 mg/kg) to an animal (e.g., a mouse, a rat, a dog, or a cynomolgus monkey) generally used in the pharmacokinetic test. After given times (e.g., 0.08, 0.25, 0.5, 1, 2, 4, 6, 8, and 24 hours) from the administration, blood was collected from an appropriate blood collection site (e.g., the jugular vein, the cephalic vein, or the saphenous vein). The obtained blood was centrifuged to prepare a plasma sample. The concentration of the test compound contained in the plasma sample was measured by quantitative analysis using a liquid chromatography-mass spectrometer (LC-MS/MS).

The pharmacokinetics of the test compound were evaluated on the basis of maximum plasma concentration (Cmax), area under the plasma drug concentration-time curve (AUC), total clearance (CL), and bioavailability and analyzed using software (Phoenix, etc.). Cmax represents the maximum plasma concentration of the orally administered test compound. AUC was calculated according to the trapezium rule from the plasma concentrations of the test compound from the time when the test compound was administered up to the final time when the test compound was quantifiable. The bioavailability was calculated according to the following expression:

[(AUC after oral administration/Dose of the oral administration)/(AUC after intravenous administration/Dose of the intravenous administration)].

The compound of the present invention exhibits excellent pharmacokinetics (Cmax, AUC, CL, or bioavailability) and is useful as a pharmaceutical (particularly, a pharmaceutical for the treatment or prevention of ectopic calcification).

PREPARATION EXAMPLES (Preparation Example 1) Capsule

| | |
|---|---|
| Compound of Example 1 | 50 mg |
| Lactose | 128 mg |
| Corn starch | 70 mg |
| Magnesium stearate | 2 mg |
| | 250 mg |

A powder having the formulation mentioned above is mixed and sifted through a 60-mesh sieve. Then, this powder is put in a gelatin capsule shell to prepare a capsule.

(Preparation Example 2) Tablet

| | |
|---|---|
| Compound of Example 1 | 50 mg |
| Lactose | 126 mg |
| Corn starch | 23 mg |
| Magnesium stearate | 1 mg |
| | 200 mg |

A powder having the formulation mentioned above is mixed, granulated using corn starch paste, and dried, followed by compression in a tableting machine to prepare tablets (200 mg each). This tablet can be coated, if necessary.

The novel pyridine compound represented by the general formula (I) of the present invention or the pharmacologically acceptable salt thereof has an excellent TNAP inhibitory effect and is useful as a pharmaceutical.

What is claimed is:
1. A compound represented by the following formula

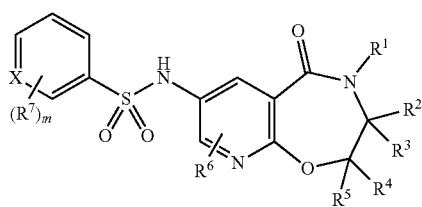

(I)

wherein
$R^1$ represents
a hydrogen atom,
a C1-6 alkyl group (wherein the alkyl group is optionally substituted by one to three groups, which may be the same or different, selected from the following substituents:
a hydroxy group, a C1-6 alkoxy group optionally substituted by one to three groups, which may be the same or different halogeno groups, an amino group optionally substituted by one or two groups, which may be the same or different C1-6 alkyl groups, a C6-10 aryl group optionally substituted by one or two groups selected from substituent group $A^B$, a 3- to 10-membered heterocyclyl group containing one to four heteroatoms, which may be the same or different, selected from nitrogen, oxygen, and sulfur and optionally substituted by one or two groups selected from substituent group $A^B$, a carboxyl group, a C1-6 alkylcarbonyl group, a C1-6 alkoxycarbonyl group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur),
a C3-8 cycloalkyl group (wherein the cycloalkyl group is optionally substituted by one to three groups, which may be the same or different, selected from the following substituents:
a hydroxy group, a C1-6 alkoxy group optionally substituted by one to three groups, which may be the same or different halogeno groups, a C3-8 cycloalkyl group optionally substituted by one to three groups, which may be the same or different halogeno groups, a C6-10 aryl group optionally substituted by one or two groups, which may be the same or different halogeno groups, a 3- to 10-membered heterocyclyl group containing one to four heteroatoms, which may be the same or different, selected from nitrogen, oxygen, and sulfur and optionally substituted by one or two groups, which may be the same or different halogeno groups,
a carboxyl group, a C1-6 alkylcarbonyl group, a C1-6 alkoxycarbonyl group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, a halogeno group, and a cyano group),
a C6-10 aryl group (wherein the aryl group is optionally substituted by one or two groups, which may be the same or different, selected from the following substituents:
a hydroxy group, a C1-6 alkyl group optionally substituted by one to three groups, which may be the same or different halogeno groups, a C3-8 cycloalkyl group optionally substituted by one to three groups, which may be the same or different halogeno groups, a C1-6 alkoxy group optionally substituted by one to three groups, which may be the same or different halogeno groups, a C6-10 aryl group optionally substituted by one group selected from substituent group $A^B$, a 3- to 10-membered heterocyclyl group containing one to four heteroatoms, which may be the same or different, selected from nitrogen, oxygen, and sulfur and optionally substituted by one group selected from substituent group $A^B$, a carboxyl group, an amino group optionally substituted by one or two groups, which may be the same or different C1-6 alkyl groups, a C1-6 alkoxycarbonyl group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, a halogeno group, and a cyano group), or a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different groups selected from the following substituents:

a hydroxy group, a C1-6 alkyl group optionally substituted by one to three groups, which may be the same or different halogeno groups, a C3-8 cycloalkyl group optionally substituted by one to three groups, which may be the same or different halogeno groups, a C1-6 alkoxy group optionally substituted by one to three groups, which may be the same or different halogeno groups, a C6-10 aryl group, a 3- to 10-membered heterocyclyl group containing one to four heteroatoms, which may be the same or different, selected from nitrogen, oxygen, and sulfur, a carboxyl group, an amino group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, a halogeno group, and a cyano group), $R^2$ and $R^3$ are the same or different and each represent a hydrogen atom, a C1-6 alkyl group (wherein the alkyl group is optionally substituted by one to three groups, which may be the same or different, selected from the following substituents:

a hydroxy group, a C1-6 alkoxy group optionally substituted by one group selected from substituent group $A^C$, a C3-8 cycloalkyl group optionally substituted by one group selected from substituent group $A^B$, a C6-10 aryl group optionally substituted by one or two groups selected from substituent group $A^B$, a 3- to 10-membered heterocyclyl group containing one to four heteroatoms, which may be the same or different, selected from nitrogen, oxygen, and sulfur and optionally substituted by one or two groups selected from substituent group $A^B$, a carboxyl group, a C1-6 alkylcarbonyl group, a C1-6 alkoxycarbonyl group, an amino group optionally substituted by one or two groups, which may be the same or different C1-6 alkyl groups, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, a halogeno group, and a cyano group), a C6-10 aryl group (wherein the aryl group is optionally substituted by one or two groups, which may be the same or different, selected from the following substituents:

a hydroxy group, a C1-6 alkoxy group optionally substituted by one to three groups, which may be the same or different halogeno groups, a C1-6 alkyl group optionally substituted by one group selected from substituent group $A^D$, a C3-8 cycloalkyl group optionally substituted by one group selected from substituent group $A^D$, a C6-10 aryl group optionally substituted by one group selected from substituent group $A^D$, a 3- to 10-membered heterocyclyl group containing one to four heteroatoms, which may be the same or different, selected from nitrogen, oxygen, and sulfur and optionally substituted by one group selected from substituent group $A^D$, an amino group optionally substituted by one or two groups, which may be the same or different C1-6 alkyl groups, a carboxyl group, a C1-6 alkylcarbonyl group, a C1-6 alkoxycarbonyl group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, a halogeno group, and a cyano group), a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from the following substituents:

a hydroxy group, a C1-6 alkoxy group optionally substituted by one to three groups, which may be the same or different halogeno groups, a C1-6 alkyl group optionally substituted by one group selected from substituent group $A^D$, a C3-8 cycloalkyl group optionally substituted by one group selected from substituent group $A^D$, a C6-10 aryl group optionally substituted by one group selected from substituent group $A^D$, a 3- to 10-membered heterocyclyl group containing one to four heteroatoms, which may be the same or different, selected from nitrogen, oxygen, and sulfur and optionally substituted by one group selected from substituent group $A^D$, an amino group optionally substituted by one or two groups, which may be the same or different C1-6 alkyl groups, a carboxyl group, a C1-6 alkylcarbonyl group, a C1-6 alkoxycarbonyl group, an aminocarbonyl group optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, a halogeno group, and a cyano group), a C1-6 alkylcarbonyl group (wherein the alkylcarbonyl group is optionally substituted by one to three groups, which may be the same or different, selected from substituent group $A^E$), a C6-10 arylcarbonyl group (wherein the arylcarbonyl group is optionally substituted by one or two groups, which may be the same or different, selected from substituent group $A^E$ and a C1-6 halogenoalkyl group), a 3- to 10-membered heterocyclylcarbonyl group containing one to four heteroatoms, which may be the same or different, selected from nitrogen, oxygen, and sulfur (wherein the heterocyclylcarbonyl group is optionally substituted by one or two groups, which may be the same or different, selected from substituent group $A^E$ and a C1-6 halogenoalkyl group), a carboxyl group, a C1-6 alkoxycarbonyl group (wherein the alkoxycarbonyl group is optionally substituted by one to three groups, which may be the same or different, selected from substituent group $A^F$), an aminocarbonyl group (wherein the aminocarbonyl group is optionally substituted by one or two groups, which may be the same or different C1-6 alkyl groups each optionally substituted by one to three groups, which may be the same or different, selected from substituent group $A^F$), a C6-10 arylaminocarbonyl group (wherein the arylaminocarbonyl group is optionally substituted by one or two groups, which may be the same or different, selected from substituent group $A^E$ and a C1-6 halogenoalkyl group), a 4- to 7-membered saturated heterocyclylcarbonyl group containing one or two heteroatoms, which may be the same or different, selected from nitrogen, oxygen, and sulfur (wherein the heterocyclylcarbonyl group is optionally substituted by one to three groups, which may be the same or different, selected from substituent group $A^F$), or a 3- to 10-membered heterocyclylaminocarbonyl group containing one to four heteroatoms, which may be the same or different, selected from nitrogen, oxygen, and sulfur (wherein the heterocyclylaminocarbonyl group is optionally substituted by one or two groups, which may be the same or different, selected from substituent group $A^E$ and a C1-6 halogenoalkyl group), or the C1-6 alkyl groups of $R^2$ and $R^3$ are optionally bonded to each other to form a 3- to 6-membered saturated carbocyclic ring or to form a 4- to 6-membered saturated heterocyclic ring via one nitrogen or oxygen atom (wherein one nitrogen atom in the 4- to 6-membered saturated heterocyclic ring is optionally replaced with a hydrogen atom, a C1-6 alkyl group, a C1-6 alkylcarbonyl group, a C1-6 alkoxycarbonyl group), $R^4$ and $R^5$ are the same or different and each represent a hydrogen atom, a C1-6 alkyl group (wherein the alkyl group is optionally substituted by one to three groups, which may be the same or different, selected from substituent group $A^G$), a C6-10 aryl group (wherein the aryl group is optionally substituted by one or two groups, which may be the same or different, selected from substituent group $A^G$), or a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group $A^G$), $R^6$ represents a hydrogen atom, hydroxyl group or a C1-6 alkyl group ($R^6$ is a carbon substituent of the pyridinyl ring, not a nitrogen substituent), each substituent $R^7$ may be the same or different and may each represent a C1-6 alkyl group (wherein the alkyl group is optionally substituted by one to three groups, which may be the same or different, selected from substituent group $A^H$), a C1-6 alkoxy group (wherein the alkoxy group is optionally substituted by one to three groups, which may be the same or different, selected from substituent group $A^H$), a halogeno group, a C6-10 aryl group (wherein the aryl group is optionally substituted by one or two groups, which may be the same or different, selected from substituent group $A^G$), a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group $A^G$), a hydroxy group, an amino group (wherein the amino group is optionally substituted by one or two groups, which may be the same or different C1-6 alkyl groups each optionally substituted by one to three groups, which may be the same or different, selected from substituent group $A^J$), a carboxyl group, a C1-6 alkoxycarbonyl group (wherein the alkoxycarbonyl group is optionally substituted by one to three groups, which may be the same or different, selected from substituent group $A^J$),
an aminocarbonyl group (wherein the aminocarbonyl group is optionally substituted by one or two groups, which may be the same or different C1-6 alkyl groups each optionally substituted by one to three groups, which may be the same or different, selected from substituent group $A^J$), or
a cyano group,
X represents —CH=, —C(—$R^7$)=, or —N=,
m represents an integer selected from 1 to 4, and
the substituent groups represent
$A^B$: a hydroxy group, a C1-6 alkyl group (wherein the alkyl group is optionally substituted by one to three halogeno groups), a C1-6 alkoxy group (wherein the alkoxy group is optionally substituted by one to three halogeno groups), a halogeno group, an amino group, and a cyano group;
$A^C$: a C6-10 aryl group, a 3- to 10-membered heterocyclyl group containing one to four heteroatoms, which may be the same or different, selected from nitrogen, oxygen, and sulfur, and a halogeno group;
$A^D$: a hydroxy group, a C1-6 alkoxy group, an amino group, a halogeno group, and a cyano group;
$A^E$: a hydroxy group, a C1-6 alkoxy group, a C3-8 cycloalkyl group, a C6-10 aryl group, a 3- to 10-membered heterocyclyl group containing one to four heteroatoms, which may be the same or different, selected from nitrogen, oxygen, and sulfur, an amino group (wherein the amino group is optionally substituted by one or two groups, which may be the same or different C1-6 alkyl groups), a halogeno group, and a cyano group;
$A^F$: a C1-6 alkoxy group, a C3-8 cycloalkyl group, a C6-10 aryl group, a 3- to 10-membered heterocyclyl group containing one to four heteroatoms, which may be the same or different, selected from nitrogen, oxygen, and sulfur, a halogeno group, and a cyano group;
$A^G$: a hydroxy group, a C1-6 alkoxy group, an amino group (wherein the amino group is optionally substituted by one or two groups, which may be the same or different C1-6 alkyl groups), a halogeno group, and a cyano group;
$A^H$: a hydroxy group, a C1-6 alkoxy group, a C3-8 cycloalkyl group, a C6-10 aryl group, a 3- to 10-membered heterocyclyl group containing one to four heteroatoms, which may be the same or different, selected from nitrogen, oxygen, and sulfur, a carboxyl group, a C1-6 alkoxycarbonyl group, an aminocarbonyl group (wherein the aminocarbonyl group is optionally substituted by one or two groups, which may be the same or different C1-6 alkyl groups), an amino group (wherein the amino group is optionally substituted by one or two groups, which may be the same or different C1-6 alkyl groups), a halogeno group, and a cyano group; and
$A^J$: a C1-6 alkoxy group, a C3-8 cycloalkyl group, a C6-10 aryl group, a 3- to 10-membered heterocyclyl group containing one to four heteroatoms, which may be the same or different, selected from nitrogen, oxygen, and sulfur, a carboxyl group, a C1-6 alkoxycarbonyl group, an aminocarbonyl group (wherein the aminocarbonyl group is optionally substituted by one or two groups, which may be the same or different C1-6 alkyl groups), a halogeno group, and a cyano group,
or a pharmacologically acceptable salt thereof.

2. A compound represented by formula (Ia):

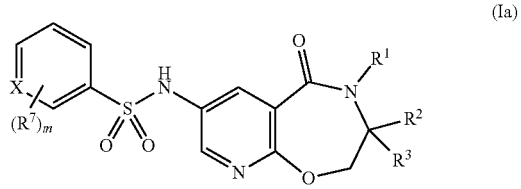

(Ia)

wherein
$R^1$ represents a hydrogen atom, a C1-6 alkyl group (wherein the alkyl group is optionally substituted by one hydroxy group or C1-6 alkoxy group), a C6-10 aryl group, or a 3- to 10-membered heterocyclyl group containing one to four heteroatoms, which may be the same or different, selected from nitrogen, oxygen, and sulfur,
$R^2$ and $R^3$ are the same or different and each represent a hydrogen atom or a C1-6 alkyl group (wherein the alkyl group is optionally substituted by one hydroxy group), or
the C1-6 alkyl groups of $R^2$ and $R^3$ are optionally bonded to each other to form a 3- to 6-membered saturated carbocyclic ring,
each substituent $R^7$ may be the same or different and may represent a C1-6 alkoxy group (wherein the alkoxy group is optionally substituted by one to three halogeno groups) or a halogeno group,
X represents —CH=, —C(—$R^7$)=, or —N=, and
m represents an integer of 1 or 2,
or a pharmacologically acceptable salt thereof.

3. The compound according to claim 2, wherein $R^1$ is hydrogen atom.

4. The compound according to claim 2, wherein $R^2$ and $R^3$ are the same or different and each represent a hydrogen atom or the C1-6 alkyl groups of $R^2$ and $R^3$ are optionally bonded to each other to form a 3- to 6-membered saturated carbocyclic ring.

5. The compound according to claim 2, wherein each substituent $R^7$ may be the same or different and may represent a methoxy group, ethoxy group, trifluoromethoxy group, fluoro or chloro.

6. A compound according to claim 1, wherein the pharmacologically acceptable salt is sodium salt.

7. A compound according to claim 1, wherein the pharmacologically acceptable salt is potassium salt.

8. A pharmaceutical composition comprising a compound according to claim 1 or a pharmacologically acceptable salt thereof, as an active ingredient, and a pharmacologically acceptable carrier.

9. A compound according to claim 2, wherein the pharmacologically acceptable salt is sodium salt.

10. A compound according to claim 2, wherein the pharmacologically acceptable salt is sodium salt.

11. A compound according to claim 2, wherein the pharmacologically acceptable salt is potassium salt.

* * * * *